(12) United States Patent
Milne et al.

(10) Patent No.: US 9,922,429 B2
(45) Date of Patent: Mar. 20, 2018

(54) METHODS AND APPARATI FOR NONDESTRUCTIVE DETECTION OF UNDISSOLVED PARTICLES IN A FLUID

(71) Applicant: Amgen Inc., Thousand Oaks, CA (US)

(72) Inventors: Graham F. Milne, Thousand Oaks, CA (US); Erwin Freund, Camarillo, CA (US); Ryan L. Smith, San Francisco, CA (US)

(73) Assignee: AMGEN INC., Thousand Oaks, CA (US)

( * ) Notice: Subject to any disclaimer, the term of this patent is extended or adjusted under 35 U.S.C. 154(b) by 61 days.

(21) Appl. No.: 15/193,720

(22) Filed: Jun. 27, 2016

(65) Prior Publication Data

US 2016/0379378 A1    Dec. 29, 2016

Related U.S. Application Data

(62) Division of application No. 14/241,861, filed as application No. PCT/US2012/052914 on Aug. 29, 2012, now Pat. No. 9,418,416.

(Continued)

(51) Int. Cl.
*G01N 15/10* (2006.01)
*G06T 7/60* (2017.01)
(Continued)

(52) U.S. Cl.
CPC ........... *G06T 7/60* (2013.01); *G01N 15/1429* (2013.01); *G01N 15/1475* (2013.01); *G01N 21/31* (2013.01); *G01N 21/51* (2013.01); *G01N 21/8851* (2013.01); *G01N 21/9027* (2013.01); *G06T 7/0012* (2013.01); *G06T 7/246* (2017.01); *G01N 15/1427* (2013.01); *G01N 2015/1075* (2013.01); *G01N 2015/1087* (2013.01);
(Continued)

(58) Field of Classification Search
CPC ................ G06T 7/246; G01N 15/1475; G01N 2015/1497; G01N 2015/1493; G01N 2015/1087
See application file for complete search history.

(56) References Cited

U.S. PATENT DOCUMENTS

| | | |
|---|---|---|
| 4,136,930 A | 1/1979 | Gomm et al. |
| 5,015,094 A | 5/1991 | Oka et al. |

(Continued)

FOREIGN PATENT DOCUMENTS

| | | |
|---|---|---|
| CN | 1464288 A | 12/2003 |
| CN | 101061382 A | 10/2007 |

(Continued)

OTHER PUBLICATIONS

Australian patent application No. 2012302036, Examination Report No. 1, dated Feb. 6, 2015.

(Continued)

*Primary Examiner* — Siamak Harandi
(74) *Attorney, Agent, or Firm* — Marshall, Gerstein & Borun LLP

(57) ABSTRACT

The apparati, methods, and computer program products disclosed herein can be used to nondestructively detect undissolved particles, such as glass flakes and/or protein aggregates, in a fluid in a vessel, such as, but not limited to, a fluid that contains a drug.

14 Claims, 54 Drawing Sheets

Related U.S. Application Data

(60) Provisional application No. 61/528,589, filed on Aug. 29, 2011, provisional application No. 61/542,058, filed on Sep. 30, 2011, provisional application No. 61/691,211, filed on Aug. 20, 2012.

(51) Int. Cl.
| | |
|---|---|
| *G01N 21/90* | (2006.01) |
| *G01N 21/31* | (2006.01) |
| *G01N 21/51* | (2006.01) |
| *G06T 7/00* | (2017.01) |
| *G06T 7/246* | (2017.01) |
| *G01N 21/88* | (2006.01) |
| *G01N 15/14* | (2006.01) |

(52) U.S. Cl.
CPC ............... *G01N 2015/144* (2013.01); *G01N 2015/1445* (2013.01); *G01N 2015/1452* (2013.01); *G01N 2015/1472* (2013.01); *G01N 2015/1477* (2013.01); *G01N 2015/1493* (2013.01); *G01N 2015/1497* (2013.01); *G06T 2207/10004* (2013.01); *G06T 2207/10016* (2013.01); *G06T 2207/30004* (2013.01); *G06T 2207/30241* (2013.01); *G06T 2207/30242* (2013.01)

(56) References Cited

U.S. PATENT DOCUMENTS

| | | | |
|---|---|---|---|
| 5,905,568 A * | 5/1999 | McDowell | G01N 15/0227 348/135 |
| 6,082,205 A | 7/2000 | Zborowski et al. | |
| 6,097,428 A | 8/2000 | Wu et al. | |
| 6,154,285 A | 11/2000 | Teng et al. | |
| 6,252,235 B1 | 6/2001 | Niino et al. | |
| 6,275,603 B1 | 8/2001 | Cronshaw et al. | |
| 6,362,887 B1 | 3/2002 | Meisberger | |
| 6,504,606 B2 | 1/2003 | Yagita | |
| 6,986,993 B1 | 1/2006 | Ghosh et al. | |
| 7,430,047 B2 | 9/2008 | Budd et al. | |
| 7,560,720 B2 | 7/2009 | Voigt et al. | |
| 7,688,427 B2 | 3/2010 | Cox et al. | |
| 7,982,868 B2 | 7/2011 | Akkerman et al. | |
| 8,270,668 B2 | 9/2012 | Reinholt et al. | |
| 9,418,416 B2 | 8/2016 | Milne et al. | |
| 9,704,239 B1 | 7/2017 | Milne et al. | |
| 2002/0005946 A1 | 1/2002 | Oomori et al. | |
| 2003/0086608 A1 | 5/2003 | Frost et al. | |
| 2004/0146917 A1 | 7/2004 | Cork et al. | |
| 2005/0068999 A1 | 3/2005 | Momiuchi et al. | |
| 2005/0099687 A1 | 5/2005 | Watanabe | |
| 2005/0248765 A1 | 11/2005 | Budd et al. | |
| 2006/0072111 A1 | 4/2006 | Budd et al. | |
| 2006/0132711 A1 | 6/2006 | Iwanaga | |
| 2006/0244964 A1 | 11/2006 | Cox et al. | |
| 2008/0001104 A1 | 1/2008 | Voigt et al. | |
| 2008/0226126 A1 | 9/2008 | Ohno | |
| 2008/0291438 A1 | 11/2008 | Akkerman et al. | |
| 2009/0323040 A1 | 12/2009 | Cornell et al. | |
| 2010/0205139 A1 | 8/2010 | Xia et al. | |
| 2010/0315410 A1 | 12/2010 | Zhang et al. | |
| 2013/0010283 A1 | 1/2013 | Villger | |
| 2014/0177932 A1 | 6/2014 | Milne et al. | |
| 2015/0160118 A1 | 6/2015 | Regelman | |
| 2015/0253240 A1 | 9/2015 | Rowe et al. | |
| 2016/0260513 A1 | 9/2016 | Pan et al. | |
| 2016/0379376 A1 | 12/2016 | Milne et al. | |
| 2016/0379377 A1 | 12/2016 | Milne et al. | |
| 2016/0379378 A1 | 12/2016 | Milne et al. | |
| 2017/0059471 A1 | 3/2017 | Wachemig et al. | |

FOREIGN PATENT DOCUMENTS

| | | |
|---|---|---|
| CN | 101126698 A | 2/2008 |
| CN | 101354241 A | 1/2009 |
| CN | 101435764 A | 5/2009 |
| CN | 101438143 A | 5/2009 |
| CN | 101561403 A | 10/2009 |
| EP | 1847961 A1 | 10/2007 |
| EP | 2122326 A1 | 11/2009 |
| JP | 47-026198 | 10/1972 |
| JP | 5510916 | 1/1980 |
| JP | 63-088431 A | 4/1988 |
| JP | H07160847 A | 6/1995 |
| JP | H08136476 A | 5/1996 |
| JP | H08305852 A | 11/1996 |
| JP | H09325122 A | 12/1997 |
| JP | H11183382 A | 7/1999 |
| JP | H11326008 A | 11/1999 |
| JP | H11513799 A | 11/1999 |
| JP | 2001116703 A | 4/2001 |
| JP | 2002107307 A | 4/2002 |
| JP | 2002267612 A | 9/2002 |
| JP | 2002340808 A | 11/2002 |
| JP | 2003270240 A | 9/2003 |
| JP | 2004028930 A | 1/2004 |
| JP | 2005121592 A | 5/2005 |
| JP | 2008508513 A | 3/2008 |
| SU | 922596 | 4/1982 |
| WO | WO-2006/080355 A1 | 8/2006 |
| WO | WO-2007/138818 A1 | 12/2007 |
| WO | WO-2013/072806 A1 | 5/2013 |
| WO | WO-2015/034505 A1 | 3/2015 |

OTHER PUBLICATIONS

Australian patent application No. 2012302036, Examination Report No. 2, dated May 30, 2015.
Australian patent application No. 2012302036, Examination Report No. 3, dated Aug. 31, 2015.
Australian patent application No. 2016100220, Innovation Patent Examination Report No. 1, dated Jun. 24, 2016.
Canadian Patent Application No. 2,843,016, Examination Report, dated Jun. 27, 2017.
Chinese patent application No. 201280039677.5, Notification of First Office Action, dated Dec. 11, 2015.
Chinese patent application No. 201510481648.X, Notification of the First Office Action, dated May 4, 2017.
Eurasian patent application No. 201490169/31, Examination Report No. 2, dated Jul. 27, 2016.
Eurasian patent application No. 201490169/31, Examination Report, dated Nov. 19, 2015.
Eurasian patent application No. 201490169/31, Notice of Allowance, dated Jan. 31, 2017.
International Application No. PCT/US2017/017302, International Search Report and Written Opinion, dated Oct. 11, 2017.
Japanese Patent Application No. 2014-528560, Notice of Reasons for Rejection, dated May 31, 2016.
Japanese patent application No. 2016-165450, Notice of Reasons for Rejection, dated Jun. 29, 2017.
Japanese patent application No. 2016-165451, Notice of Reasons for Rejection, dated Jun. 29, 2017.
Mu et al., Three-dimensional particle image measurement technique based on spheroid particle-liquid two-phase flows inside round tube, Chinese J. Science Instrument, 30(5):1068-107 (2009).
Singapore Patent Application No. 2014004691, Examination Report, dated Aug. 19, 2015.
Singapore Patent Application No. 2014004691, Written Opinion, dated Jan. 30, 2015.
Taiwan Patent Application No. 101131282, Office Action, dated May 16, 2016.
Taiwan Patent Application No. 101131282, Search Report, dated May 11, 2016.
U.S. Appl. No. 15/192,920, Corrected Notice of Allowability, dated Nov. 8, 2017.

(56) References Cited

OTHER PUBLICATIONS

U.S. Appl. No. 15/192,920, Nonfinal Office Action, dated Jun. 7, 2017.
U.S. Appl. No. 15/192,920, Notice of Allowance, dated Aug. 28, 2017.
U.S. Appl. No. 15/193,704, Nonfinal Office Action, dated Aug. 23, 2017.
U.S. Appl. No. 15/193,704, Notice of Allowance, dated Nov. 22, 2017.
U.S. Appl. No. 15/193,720, Restriction Requirement, dated Nov. 15, 2017.
U.S. Appl. No. 15/256,429, Milne et al., filed Sep. 2, 2016.
U.S. Appl. No. 15/256,429, Nonfinal Office Action, dated Nov. 23, 2016.
U.S. Appl. No. 15/256,429, Notice of Allowance, dated Mar. 6, 2017.
U.S. Appl. No. 15/429,458, Final Office Action, dated Oct. 6, 2017.
U.S. Appl. No. 15/429,458, Fradkin et al., filed Feb. 10, 2017.
U.S. Appl. No. 15/429,458, Nonfinal Office Action, dated May 12, 2017.
Wu et al., Defect recognition technique based on edge detection automatic position compensation, Modern Manufacturing Engineering, No. 5:74-6 (2004).
International Search Report (ISA/EPO) for International Application No. PCT/US2012/052914, dated Jan. 4, 2013, 3 pages.
Non-Final Office Action for U.S. Appl. No. 14/241,861 dated Dec. 23, 2015.
Notice of Allowance for U.S. Appl. No. 14/241,861 dated Apr. 26, 2016.
Restriction Requirement for U.S. Appl. No. 14/241,861 dated Oct. 15, 2015.

\* cited by examiner

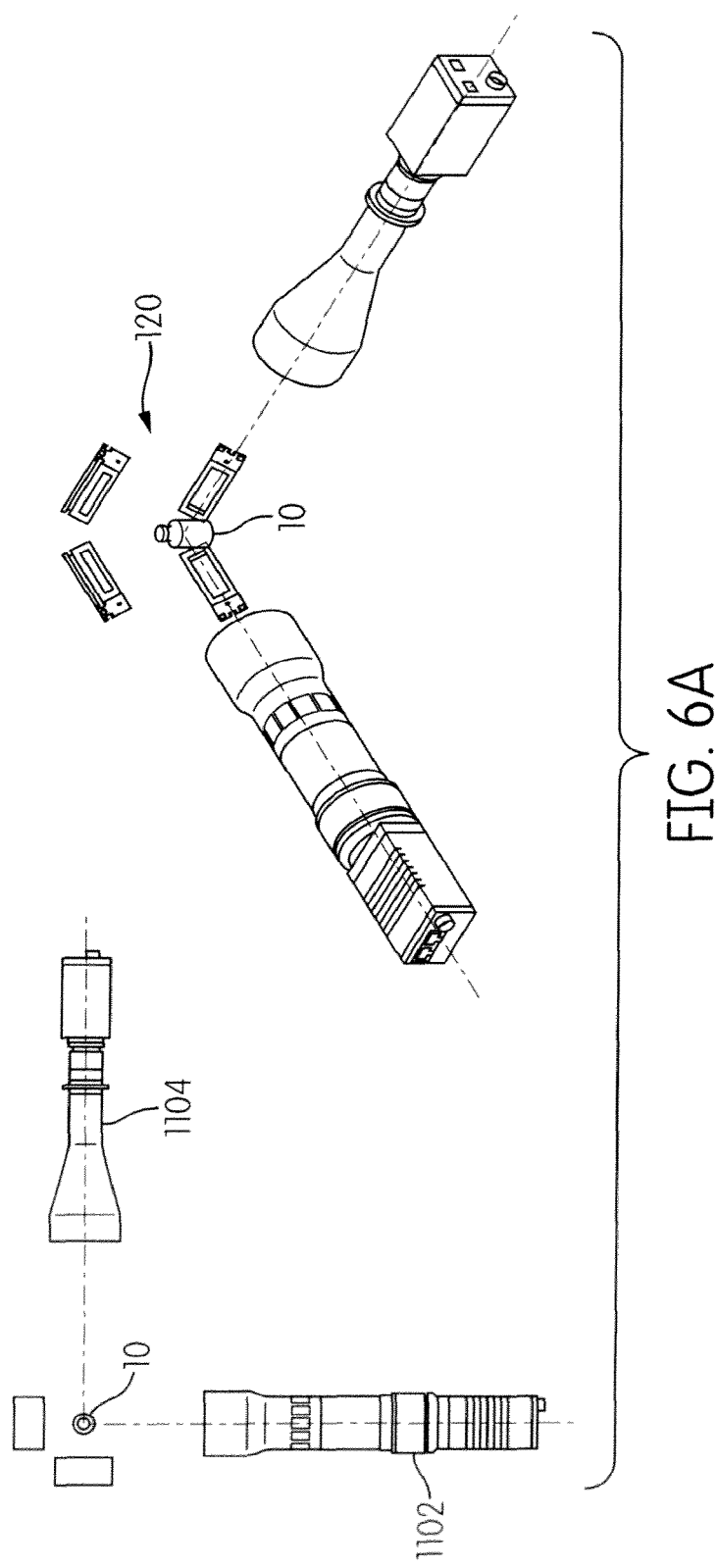

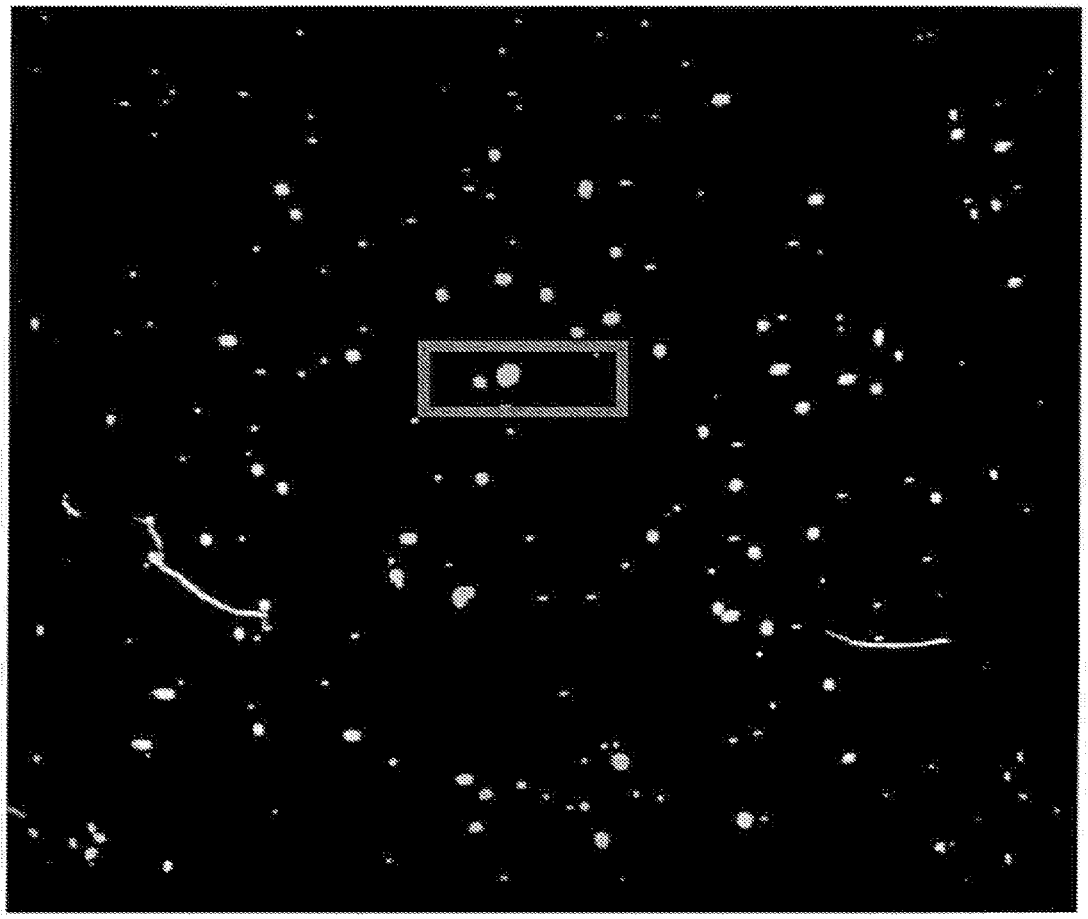
FIG. 20A
      
FIG. 20B        FIG. 20C        FIG. 20D        FIG. 20E

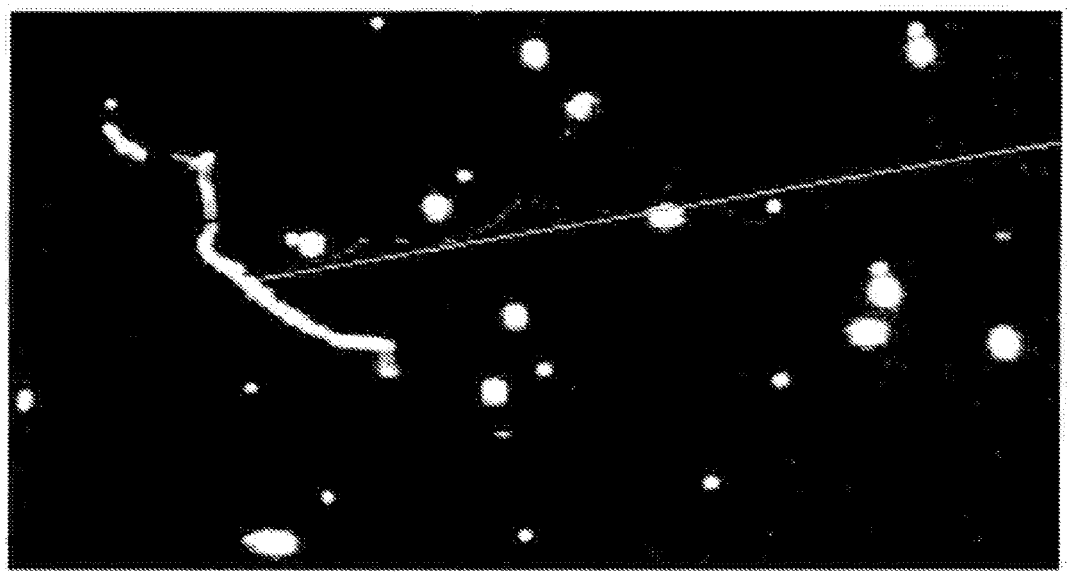
FIG. 22A
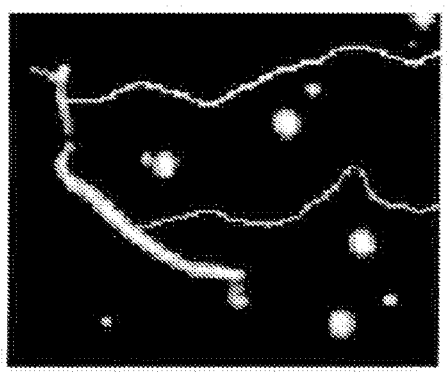 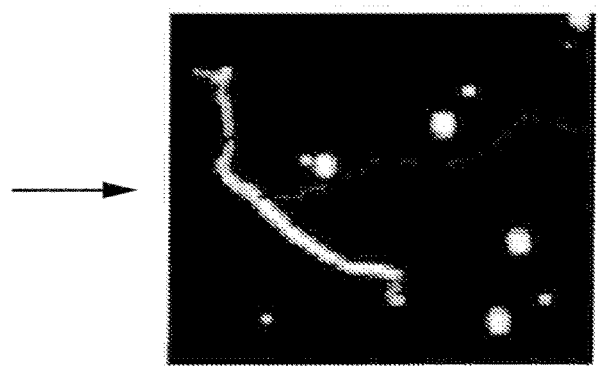
FIG. 22B          FIG. 22C

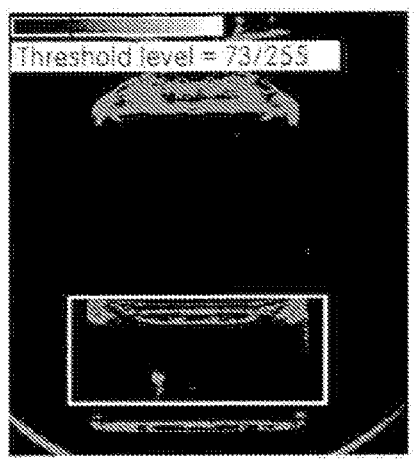 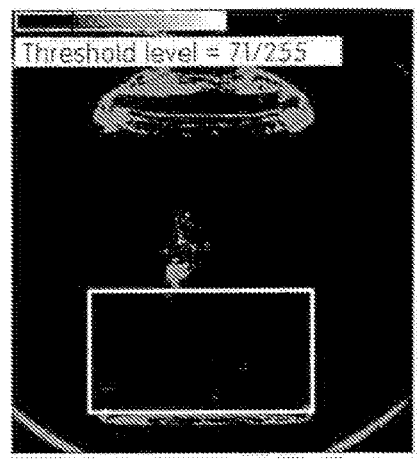
FIG. 29A    FIG. 29B
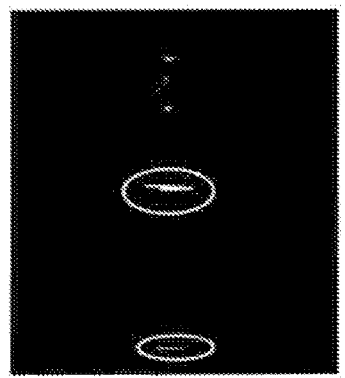 
AFTER    BEFORE
FIG. 29C
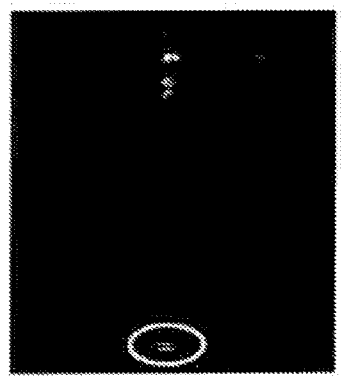 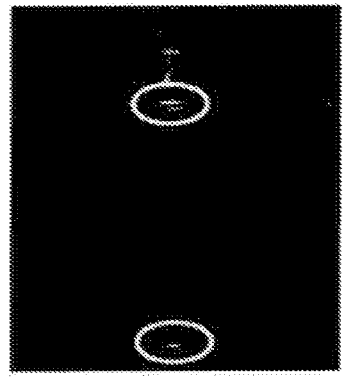
EMPTY VIAL    FULL VIAL
FIG. 29D

| Size (µm) | R^2 |
|---|---|
| 15 | 0.995 |
| 50 | 0.993 |
| 100 | 0.995 |
| 140 | 0.957 |
| 200 | 0.985 |

METHODS AND APPARATI FOR NONDESTRUCTIVE DETECTION OF UNDISSOLVED PARTICLES IN A FLUID

CROSS-REFERENCE TO RELATED APPLICATIONS

This application is a divisional of U.S. patent application Ser. No. 14/241,861, filed Feb. 28, 2014, which is a national stage application under 35 U.S.C. § 371 of International Application No. PCT/US2012/052914, filed Aug. 29, 2012, which in turn claims the benefit under 35 U.S.C. § 119(e) to U.S. Provisional Application Nos. 61/691,211, 61/542,058 and 61/528,589, filed Aug. 20, 2012, Sep. 30, 2011 and Aug. 29, 2011, respectively, the content of each of which is incorporated by reference in its entirety into the present disclosure.

BACKGROUND

Differentiation between various types of particles is important in order to characterize the quality of a given formulation of drug product. For instance, low specificity in differentiation has the potential to confuse objects, such as glass lamellae, for proteinaceous particulate matter. High specificity of the differentiation system is needed in order to provide accurate decisions when making decisions on formulations. Without information about the type(s) of particles in a particular drug product, it may be difficult to formulate the drug product properly.

Unfortunately, conventional particle detection techniques are unsuitable for detecting protein aggregates and other small and/or delicate particles. Human inspectors usually cannot detect particles that are smaller than about 100 microns. Automated inspection techniques are typically destructive; that is, they involve removing the fluid being inspected from its container, which usually renders the fluid unsuitable for therapeutic use. In addition, conventional nondestructive inspection systems use only a single snapshot of the container to determine whether or not particles are present, which often leads to imprecise particle size measurements and/or particle counts. Conventional inspection techniques may also involve destruction of more delicate particles, such as protein aggregates. For example, spinning a vial filled fluid at high speed (e.g., 2000 rpm or more for several seconds) may rip apart protein aggregates in the fluid.

SUMMARY

One embodiment of the technology disclosed herein relates to an apparatus for nondestructive detection of a particle (i.e., an undissolved particle) in a vessel that is at least partially filled with a fluid, such as an aqueous fluid, an emulsion, an oil, an organic solvent. As used herein, the term "detection", or "detecting", is to be understood to include detecting, characterizing, differentiating, distinguishing, or identifying, the presence, number, location, identity, size, shape (e.g., elongation or circularity), color, fluorescence, contrast, absorbance, reflectance, or other characteristic, or a combination of two, three, four, five, six, seven, eight, nine, ten, eleven, twelve or more of these characteristics, of the particle. In illustrative embodiments, the apparatus includes an imager to acquire time-series data representing a trajectory of the particle in the fluid. A memory operably coupled to the imager stores the time-series data, and a processor operably coupled to the memory detects and/or identifies the particle. More specifically, the processor reverses a time ordering of the time-series data to form reversed time-series data, estimates the trajectory of the particle from the reversed time-series data, and determines a presence or type of the particle based on the trajectory. As defined herein reversed time-series data includes frames of times-series data that have been arranged in reverse chronological order, such that the last-occurring event appears first (and vice versa).

Further embodiments include a method and corresponding computer program product for nondestructive detection of an undissolved particle in a vessel that is at least partially filled with a fluid. Implementing the method involves reversing a time ordering of time-series data representing a trajectory of the particle in the fluid to form reversed time-series data, e.g., with a processor that executes instructions encoded in a nonvolatile memory of the computer program product. The method further includes estimating the trajectory of the particle from the reversed time-series data, then detecting and/or identifying the particle based on the trajectory.

Another embodiment is an apparatus for nondestructive detection of an undissolved particle in a vessel that is at least partially filled with a fluid, the apparatus which involves:
  (a) at least two imagers positioned to image the particle from different perspectives, each imager configured to acquire one or more two dimensional images of the particle in the fluid;
  (b) a memory operably coupled to the imager and configured to store the time-series; and
  (c) a processor operably coupled to the memory and configured to detect the particle by:
    (i) combining the two dimensional images from the at least three imagers to determine three dimensional data indicative of the position of the particle in the vessel; and
    (ii) detecting the particle based at least in part on the three dimensional data.

Also encompassed is a method for nondestructive detection of an undissolved particle in a vessel that is at least partially filled with a fluid, the method comprising:
  (a) using at least two imagers to image the particle from different perspectives to each acquire a respective one or more two dimensional images of the particle in the fluid;
  (b) combining the two dimensional images from the at least two imagers to determine three dimensional data indicative of the position of the particle in the vessel; and
  (c) detecting the particle based at least in part on the three dimensional data.

Other embodiments of the present invention include an apparatus, method, and computer program product for nondestructive detection of (one or more) transparent or reflective objects (e.g., glass lamellae) in a vessel that is at least partially filled with a fluid. An imager acquires data that represent light reflected from a plurality of spatial locations in the vessel as a function of time and stores the data in a memory operably coupled to the imager. A processor operably coupled to the memory detects the objects (e.g., glass lamellae), possibly in response to instructions encoded in the computer program product, based on the data by identifying a respective maximum amount of reflected light for each location in the plurality of locations represented by the data. The processor then determines a presence or absence of the objects (e.g., glass lamellae) in the vessel based on the number of spatial locations whose respective maximum amount of reflected light exceeds a predetermined value.

Another embodiment of the invention is a method of nondestructive counting and sizing of undissolved particles in a vessel that is at least partially filled with a fluid. The method involves:
(a) receiving at least one image of the particles in the vessel obtained under specified imaging conditions;
(b) based on the at least one image, detecting the particles and determining information indicative of the apparent size of the detected particles in the image;
(c) determining apparent particle size population information indicative of an apparent particle size distribution of the detected particles; and
(d) determining actual particle size population information indicative of the actual particle size distribution of the detected particles based on
  (i) the apparent particle size population information and
  (ii) calibration population information indicative of the apparent size distribution of one or more sets of standard sized particles imaged under conditions corresponding to the specified imaging conditions.

Another embodiment of the invention is an apparatus for counting and sizing undissolved particles in a vessel that is at least partially filled with a fluid, the apparatus including at least one processor configured to:
(a) receive at least one image of the particles in the vessel obtained under specified imaging conditions;
(b) based on the at least one image, detect the particles and determine information indicative of the apparent size of the detected particles in the image;
(c) determine apparent particle size population information indicative of an apparent particle size distribution of the detected particles; and
(d) determine actual particle size population information indicative of the actual particle size distribution of the detected particles based on
  (i) the apparent particle size population information and
  (ii) calibration population information indicative of the apparent size distribution of one or more sets of standard sized particles imaged under conditions corresponding to the specified imaging conditions.

A further embodiment of the invention is a computer program product for nondestructive counting and sizing of undissolved particles in a vessel that is at least partially filled with a fluid, the computer program product comprising nonvolatile, machine-readable instructions, which, when executed by a processor, cause the processor to
(a) receive at least one image of the particles in the vessel obtained under specified imaging conditions;
(b) based on the at least one image, detect the particles and determine information indicative of the apparent size of the detected particles in the image
(c) determine apparent particle size population information indicative of an apparent particle size distribution of the detected particles; and
(d) determine actual particle size population information indicative of the actual particle size distribution of the detected particles based on
  (i) the apparent particle size population information and
  (ii) calibration population information indicative of the apparent size distribution of one or more sets of standard sized particles imaged under conditions corresponding to the specified imaging conditions.

A further embodiment of the invention is a method for nondestructive detection of an undissolved particle in a vessel that is at least partially filled with a fluid, the method including:
(a) using at least one imager to image the particle;
(b) processing the image to determine position data indicative of the position of the particle in the vessel;
(c) detecting the particle based at least in part on the position data, where detecting the particle based at least in part on position data includes identifying the presence of the particle in a sub-region of the vessel;
(d) using a sensor to determine a characteristic of the particle when the particle is located in the sub-region of the vessel,
(e) generating particle characteristic data indicative of the determined characteristic; and
associating the particle characteristic data with data identifying the particle.

A further embodiment of the invention is an apparatus for nondestructive detection of an undissolved particle in a vessel that is at least partially filled with a fluid, the apparatus including:
(a) at least one imager positioned image the particle;
(b) at least one sensor configured to determine a characteristic of the particle when the particle is located in the sub-region of the vessel;
(b) at least one processor operably couple to the each least one imager and the sensor and configured to:
  process the image to determine position data indicative of the position of the particle in the vessel;
  detect the particle based at least in part on the position data and identify the presence of the particle in a sub-region of the vessel;
  use a signal from the sensor to determine a characteristic of the particle when the particle is located in the sub-region of the vessel,
generate particle characteristic data indicative of the determined characteristic; and
associate the particle characteristic data with data identifying the particle.

Another embodiment of the invention is an apparatus for nondestructive detection of an undissolved particle in a vessel that is at least partially filled with a fluid, where the vessel includes a transparent tubular vessel wall disposed about a longitudinal axis, the apparatus including: an imager configured to acquire one or more images of the particle in the fluid, the imager including a at least one imaging optical element positioned to image the particle onto the sensor; an illumination source positioned at least partially within a plane passing through the vessel and substantially orthogonal to the longitudinal axis of the vessel, the illumination source arranged to substantially eliminate the presence of light rays emitted from the source that reflect or refract from a surface of the vessel wall and are imaged by the at least one optical element onto the sensor.

Another embodiment of the invention is a method for nondestructive detection of an undissolved particle in a vessel that is at least partially filled with a fluid, wherein the vessel comprises a transparent tubular vessel wall disposed about a longitudinal axis, the method comprising: using an imager to acquire one or more images of the particle in the fluid, the imager comprising at least one imaging optical element positioned to image the particle onto the sensor; and illuminating the vessel with an illumination source positioned at least partially within an plane passing through the vessel and substantially orthogonal to the longitudinal axis of the vessel, the illumination source arranged to substantially eliminate the presence of light rays emitted from the source that reflect or refract from a surface of the vessel wall and are imaged by the at least one optical element onto the sensor.

Unlike other particle detection systems and techniques, the inventive systems and techniques operate nondestructively—there is no need to remove the fluid from the vessel to detect, count, and identify the particles in the vessel. As a result, inventive systems and techniques can be used to study changes in and interactions among the particles, the fluid, and the vessel over long time spans, e.g., minutes, hours, days, months, or years. In addition, inventive systems and techniques do not necessarily involve or result in the destruction of even more delicate particles, such as small protein aggregates, in the vessel. They also capture time-series data, i.e., data representing the trajectories of the particles in the moving fluid. Because the inventive systems use time-series data instead of single-frame snapshots of the vessel, they can estimate more precisely the number of particles in the vessel and the particle sizes. They can also derive more information about each particle, such as particle morphology and particle composition, from the particle's motion. For example, falling particles tend to be denser than rising particles.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the disclosed technology and together with the description serve to explain principles of the disclosed technology.

FIGS. 6A-6D show particle tracking systems with multiple imagers to capture time-series data of the moving particles from many angles (FIGS. 6A and 6B), at higher frame rates from the same angle (FIG. 6C), and at different spatial resolutions from the same angle (FIG. 6D).

FIG. 20A shows a frame of time-series data with a pair or particles next to each other inside a highlighted region.

FIGS. 20B-20E are successive frames of time-series data showing particle occlusion apparent as the particles in the highlighted region of FIG. 20A propagate past each other.

FIGS. 22A-22C illustrate location of the center of mass of an irregularly-shaped particles using reversed time-series data (FIGS. 22B and 22C) and use of the center-of-mass location to determine particle trajectory (FIG. 22A).

FIG. 23A shows changes in the shape of the meniscus. FIGS. 23B and 23C illustrate vortex formation inside a fluid-filled vessel, and FIG. 23D shows particle trajectories in an illustrative vortex.

FIG. 27A shows an original image (frame of time-series data) that is subject to edge detection (FIG. 27B), grayscale thresholding (FIG. 27C), identification of the meniscus and vial-base (FIG. 27D), determination of a region of interest (bounded by dotted lines in FIG. 27E), and cropping (FIG. 27F) to yield an image of the fluid visible in the container.

FIG. 28A shows a raw image of the vial. FIG. 28B shows a region of interest (bounded by the dotted lines) determined using thresholding and edge detection. Defects on the surface of the vial (shown in FIG. 28C) may hamper fill volume detection.

FIGS. 29A-29D illustrate fill volume detection of a vial illuminate from underneath. FIGS. 29A and 29B are false-color images of a partially full vessel (FIG. 29A) and an empty vessel (FIG. 29B). FIGS. 29C and 29D illustrate automatic meniscus detection of partially full, empty, and partially filled vessels.

DETAILED DESCRIPTION

Figure 1A:
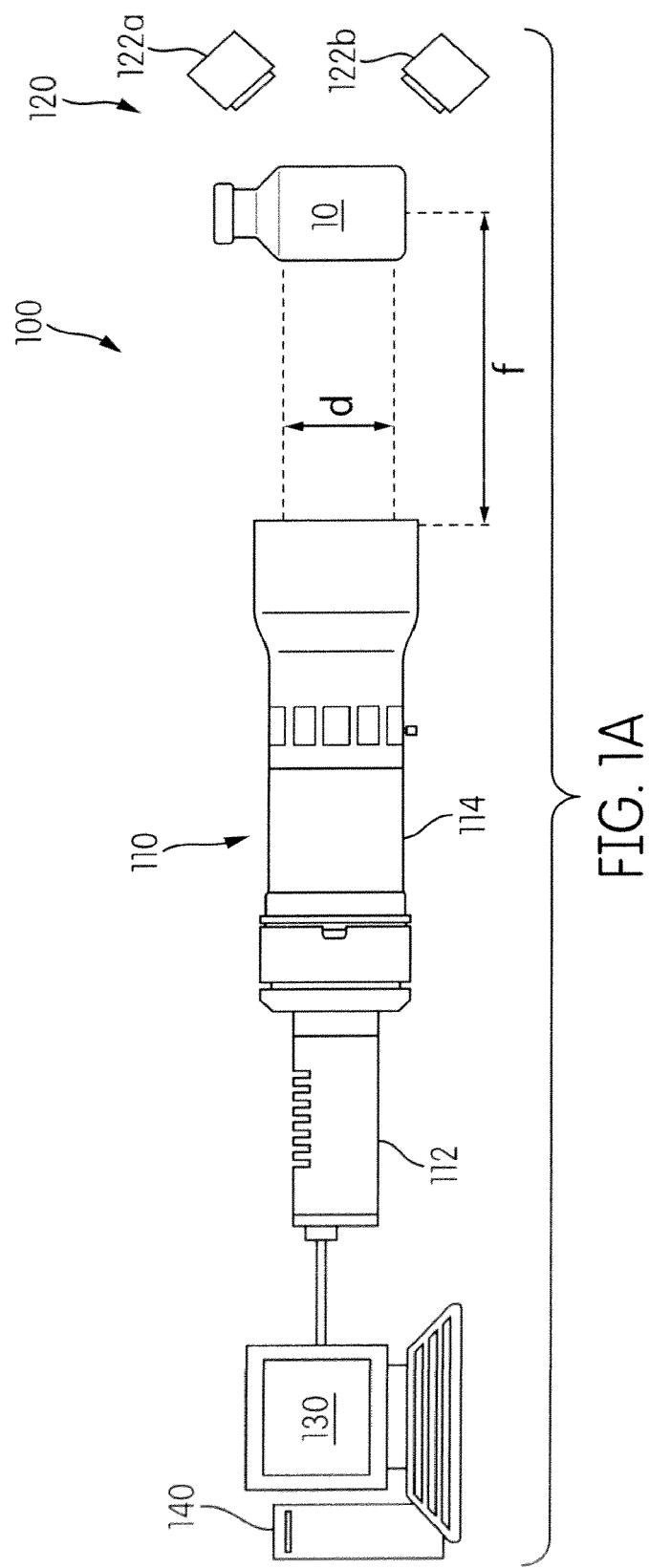
FIGS. 1A-1C show a visual inspection unit, a visual inspection imaging module, and a visual inspection platform, respectively, that can each be used to detect and identify particles in a container that is at least partially filled with a fluid.

FIG. 1A shows an exemplary automated visual inspection unit 100 configured to non-destructively detect and/or identify particles in a transparent container 10 that is at least partially filled with fluid, such as a protein-containing pharmaceutical composition, drugs, biotechnology products, drinks, and other translucent fluids regulated by the U.S. Food and Drug Administration.

Although detection of the presence or absence of a particle can be accomplished by viewing portions of the container in which the exterior is non-uniform (e.g. the heel), in typical embodiments, for particle characterization measurements such as counting and sizing, it may be necessary to look at the particles through the substantially uniform vertical wall of the container in order to mitigate distortions. This has implications on minimum fill volume, as the apparent two dimensional cross section of the fluid in the container 10 visible to the unit 100 must be of an appropriate area to provide usable statistics. The required fill volume is dependent on the circular diameter of the container (smaller containers, less fill volume required). In various embodiments, the interior volume of the container may be at least 1%, at least 5%, at least 10%, at least 20%, at least 30%, at least 40%, at least 50%, at least 60%, at least 70%, at least 80%, at least 90%, or at least 100% filled with fluid.

In various embodiments, the particle detection techniques described herein are optical in nature. Accordingly, in some embodiments, the walls of container 10 are sufficiently transparent at the illuminating wavelength to allow visualization of the liquid contained within. For example, in some embodiments, the container 10 may be made from clear borosilicate glass, although other suitable materials may be used. The turbidity of the fluid contained within the vessel is also of importance, and should be sufficiently low to allow for the desired level of visualization. In some embodiments, embodiments, the fluid has turbidity in the range 0-100 NTU (Nephelometric Turbidity Units), preferably 0-20 NTU, and more preferably 0-10 NTU. Standard practices for turbidity measurement may be found, e.g., EPA Guidance Manual, Turbity Provisions, Chapter 3 (April, 1999).

Illustrative systems can detect and identify transparent and/or translucent particles that refract and/or scatter light (e.g., protein aggregates, glass flakes or lamellae, and blobs of oil), particles that reflect light (e.g., metal flakes), and/or particles that absorb light (e.g., black carbon and plastic particles) based on their different optical characteristics. Some inventive visual inspection units 100 can detect all three classes of particle by using illumination sequences such as those described below. Inventive visual inspection units 100 may also be specially configured to detect, identify, and/or track proteins, which may appear as densely bound aggregates, loosely bound cotton wool substances with high water content, (reflective) crystals, gelatinous substances, and/or amorphous aggregates.

The term "protein," which may be used interchangeably with the term "polypeptide," refers in its broadest sense to a compound of two or more subunit amino acids, amino acid analogs or peptidomimetics. The subunits may be linked by peptide bonds. In another embodiment, the subunits may be linked by other bonds, e.g., ester, ether, etc. As used herein the term "amino acid" refers to natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment" as used herein, also refers to a peptide chain.

The container 10 may be a rectangular or cylindrical vessel made of glass or plastic (e.g., a cuvette, vial, ampoule, cartridge, test tube, or syringe); it can also have another shape and/or be made of different material, so long as it provides visualization of the container contents at the imaging wavelength. Although particular embodiments provide clear and unperturbed visualization of the container contents, other embodiments may time image acquisition to coincide with periods when the container is unperturbed and/or employ postprocessing to compensate for distortion of the recorded data.

The unit 100 includes an imager 110 with collection optics that project images of the container contents onto a sensor. In this case, the collection optics include a telecentric lens 114, and the sensor is a charge-coupled device (CCD) 112. Memory 140 coupled to the CCD 112 records and stores a stream of images representing the container contents, and a processor 130 coupled to the memory 140 analyzes the recorded image sequence as described below to detect and identify the particles in the container 10. As understood by those of skill in the art, the processor 130 may be implemented with a suitably configured general-purpose computer (e.g., one using an Intel® Core™ i5 or Advanced Micro Devices Athlon™ processor), field-programmable gate array (e.g., an Altera® Stratix® or Xilinx® Spartan®-6 FPGA), or application-specific integrated circuit. The memory 140 may be implemented in solid-state memory (e.g., flash memory), optical disc (e.g., CD or DVD), or magnetic media, and can be selected to be any appropriate size (e.g., 1 GB, 10 GB, 100 GB, or more).

Figure 1B:
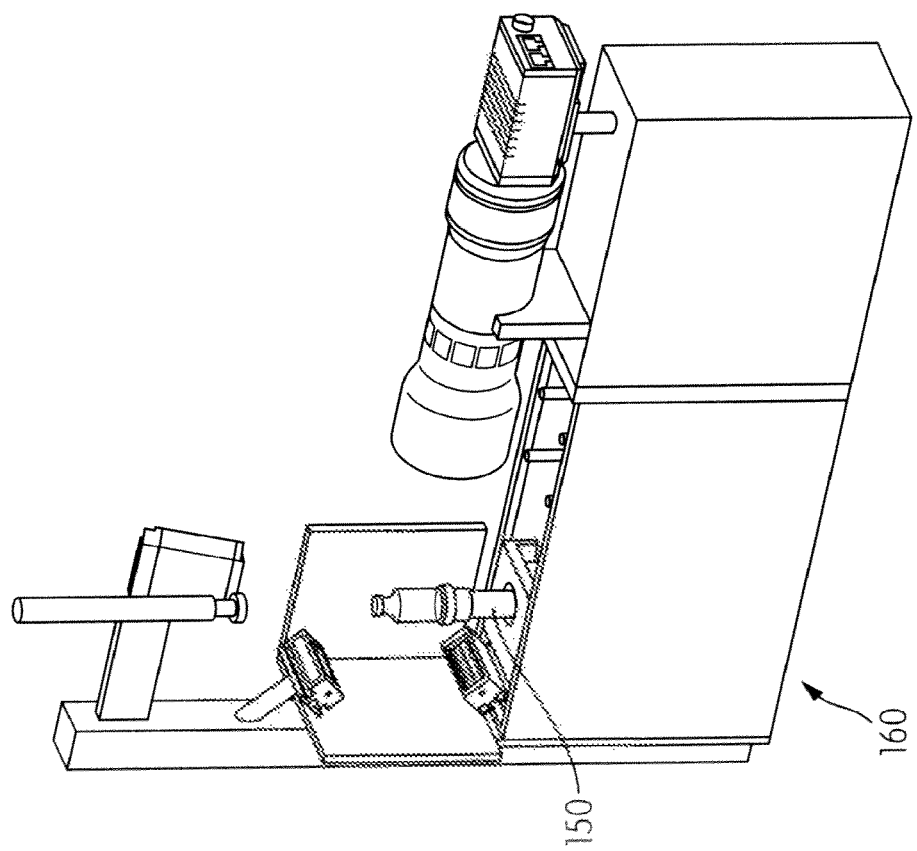

An illumination system 120, which includes one or more light sources 122a and 122b disposed around the container 10, illuminates the container 10 and its contents during image acquisition. The visual inspection unit 100 can be integrated into an inspection module 160 that also includes a spindle 150, shaker, ultrasonic vibrator, or other agitator to spin, shake, or otherwise agitate the container contents prior to imaging and to hold the container 10 during imaging, as in FIG. 1(b).

Figure 1C:
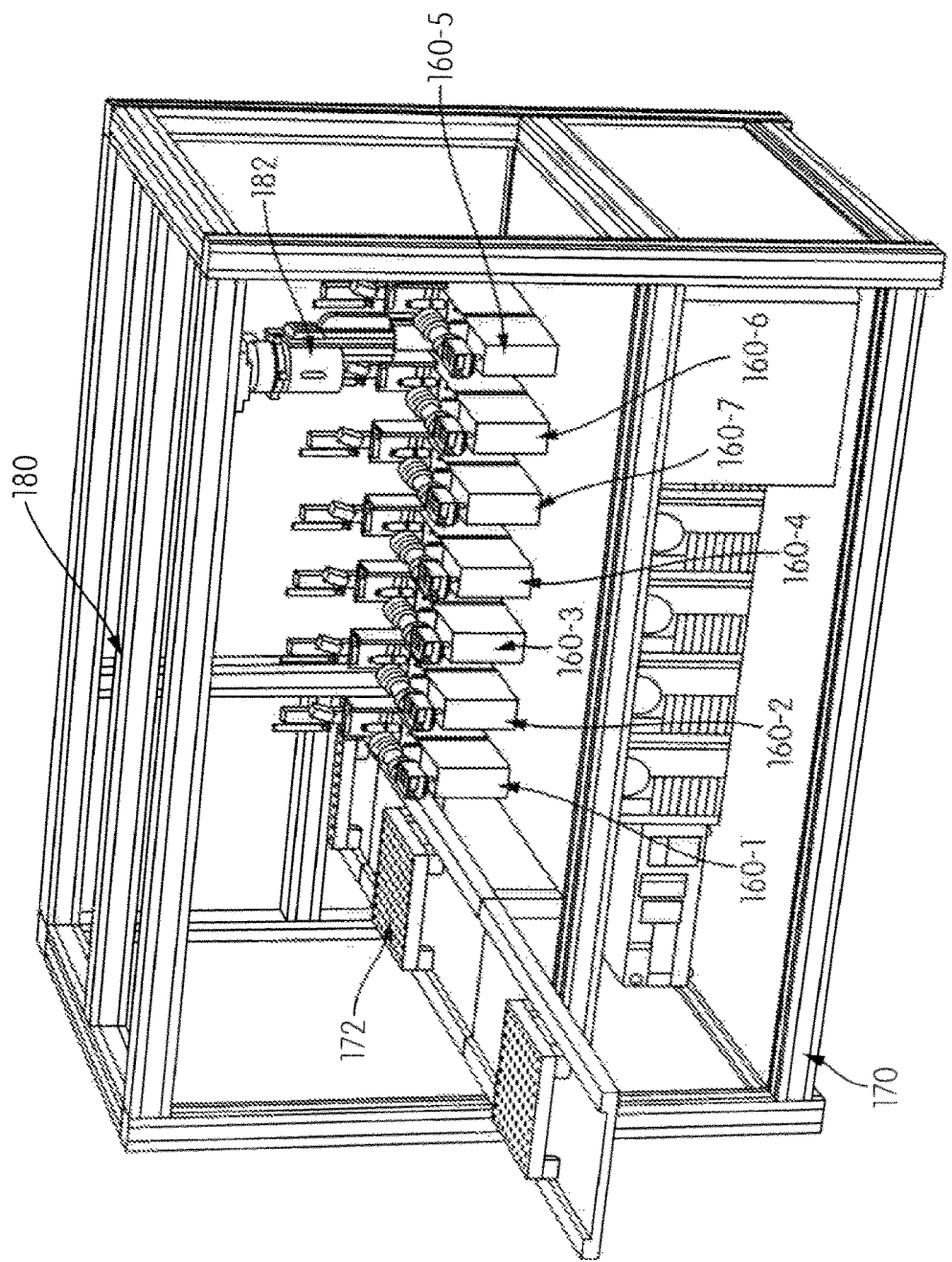

FIG. 1(c) shows a medium-to-high throughput visual inspection platform 170 that includes one or more inspection modules 160-1 through 160-5 (generally, inspection modules 160), a robot 180, and a vial tray 172, which holds uninspected and/or inspected containers 10 in individual container wells. Upon instructions from a user or automatic controller (not shown), the robot 180 moves a container 10 from the vial tray 172 to an inspection module 160, which captures and records time-series data of particles moving the container 10. The robot 180 then returns the container 10 to the vial tray 172.

In some examples, the top layer of the vial tray 172 and/or rims of the container wells are made of Delrin® acetal resin or another similar material, and the interior edges of the container wells are beveled to prevent the containers 10 from becoming scratched as they are inserted into and removed from the container wells. The vial tray 172 may include a base layer made of aluminum or another similar material that does not easily warp or crack. The walls of the container wells are typically thick to hold the vials securely as the tray 172 is carried (e.g., by a person) to and from the visual inspection platform 170. Depending on its construction, the vial tray 170 may hold the containers 10 in predefined positions to within micron-scale tolerances to facilitate container retrieval and insertion by the robot 180, which may operate with micron-scale precision.

The robot 180 is a "pick-and-place" system that plucks vials from the tray 172, moves each container 10 along a rail 182 that extends from above the tray 172 to above the spindles 160, and places the container 10 on a particular spindle 160. Some robots may also be configured to spin the container 10 before placing the container 10, obviating the need for a spindle 160. Alternatively, the robot 180 may include a six-axis robotic arm that can spin, vibrate, and/or shake (e.g., perform the "back-and-forth" needle shaking described below) the container 10, which also obviates the need for spindles 160. Those of skill in will readily appreciate that other loading and agitation mechanisms and sequences can be used with the inventive visual inspection systems and processes.

Figure 2A:
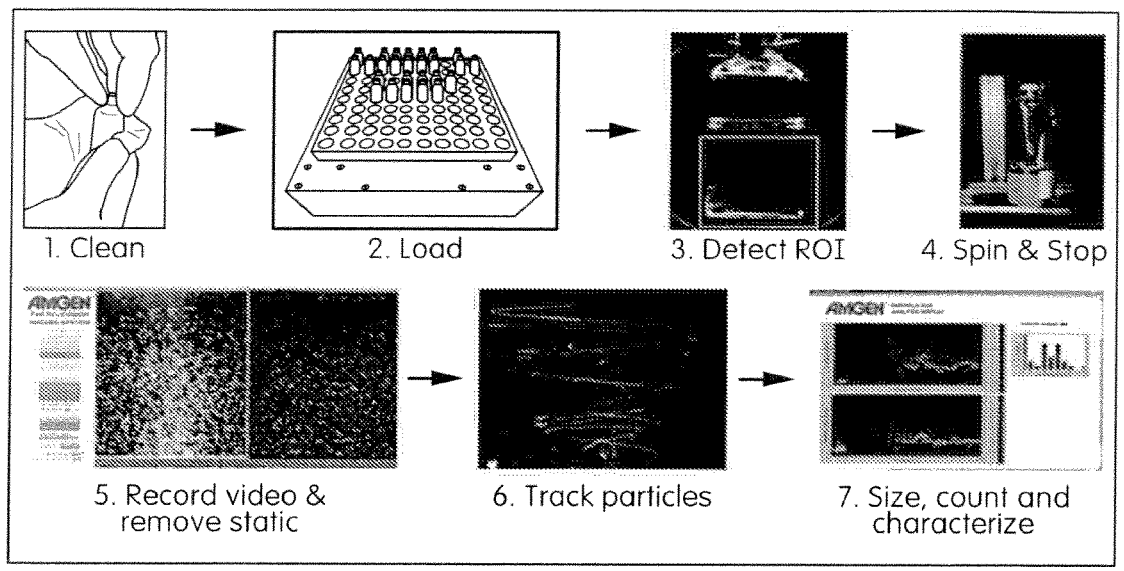
FIG. 2A illustrates sample preparation, loading, and operation of the visual inspection systems shown in FIGS. 1A-1C.
Figure 2B:
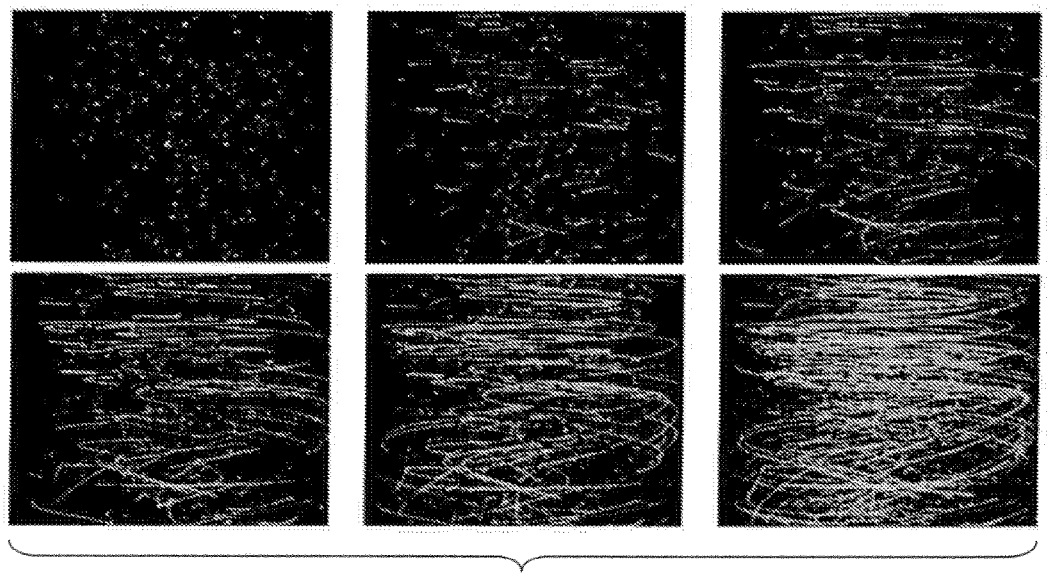
FIG. 2B shows processed images, captured by an illustrative visual inspection system, of particles and their trajectories in moving fluid in a vessel.

The visual inspection platform 170 operates as shown in FIG. 2(a). In step 202, the containers 10 to be inspected are cleaned (e.g., by hand using appropriate solvents), then loaded into the tray 172 in step 204. The robot 180 extracts a container 10 from the tray 172 and places it on the spindle 160. Next, in step 206, the processor 130 determines the size and location of the meniscus and/or region of interest (ROI), (e.g., the portion of the container 10 filled with fluid), from an image of the static container 10 acquired by the imager 110. Alternatively, the user can specify the location of the meniscus and/or the region of interest if the fill volume and container shape and volume are known with sufficient certainty. Once the processor 130 has located the ROI, the spindle 160 spins and stops the container 10 in step 208, which causes the fluid to move and particles in the container 10 to become suspended in the moving fluid. In step 210, the imager 110 records times-series data in memory 140 in the form of a sequence of static images (called "frames") representing snapshots of the ROI, taken at regularly spaced time intervals.

After the imager 110 has acquired enough time-series data, the processor 130 subtracts background data, which may represent dirt and/or scratches on one or more of the surfaces of the container. It may also filter noise from the time-series data as understood by those of skill in the art and perform intensity thresholding as described below. The processor 130 also reverses the ordering of the time-series data. That is, if each frame in the time-series data has an index 1, 2, ..., n−1, n that indicates the order in which it was acquired, the frames in the reversed time-series data are arranged with indices ordered n, n−1, ..., 2, 1. If necessary, the processor 130 also selects start and end points of the data to be analyzed as described below. (Those of skill in the art will readily appreciate that the processor 130 may perform background subtraction, noise filtering, intensity thresholding, time-series data reversal, and start/end point determination in any order.) The processor 130 tracks particles moving in or with the fluid in step 212, then sizes, counts, and/or otherwise characterizes the particles based on their trajectories in step 214.

Each inspection module 160 may perform the same type of inspection, allowing for parallel processing of the containers 10; the number of modules 160 can be adjusted depending on the desired throughput. In other embodiments, each module 160 may be configured to perform different types of inspections. For example, each module 160 may inspect particles at a different illumination wavelength: module 160-1 may look for particles that respond to visible light (i.e., radiation at a wavelength of about 390 nm to about 760 nm), module 160-2 may inspect containers using near infrared illumination (760-1400 nm), module 160-2 may inspect containers using short-wavelength infrared illumination (1.4-3.0 μm), module 160-4 may inspect particles at ultraviolet wavelengths (10-390 nm), and module 160-5 may inspect particles a X-ray wavelengths (under 10 nm). Alternatively, one or more modules 160 may look for polarization effects and/or particle fluorescence.

In embodiments with different types of modules 160, the first module 160-1 may perform preliminary inspections, with subsequent inspections contingent upon results of the preliminary inspections. For instance, the first module 160-1 may perform a visible-light inspection that suggests that a particular container contains polarization-sensitive particles. The processor 130 may then instruct module 160-2, which is configured to perform polarization-based measurements, to inspect the container in order confirm (or disprove) the presence of polarization-sensitive particles. Visible-light time-series data acquired by module 160-1 may indicate the presence of several particles in a particular container 10, but not the particle type, which may lead the processor 130 to order, e.g., infrared inspection at module 160-3.

Container Agitation to Induce Particle Movement

As described above, mechanically agitating the container 10 causes particles at the bottom of the container 10 or on the sides of the container's inner walls to become suspended in the fluid within the container. In particular embodiments, the user and/or visual inspection system selects and performs an agitation sequence that causes the fluid in the container to enter a laminar flow regime, which is regime in which the fluid flows in parallel layers, with no eddies, swirls, or disruptions between the layers. In fluid dynamics, laminar flow is a flow regime characterized by high momentum diffusion and low momentum convection—in other words, laminar flow is the opposite of rough, turbulent flow. Agitation also causes the particles to become suspended in the moving fluid. Eventually, friction causes the fluid to stop moving, at which point the particles may stick to the walls of the container or settle to the bottom of the container.

Compared to turbulent flow, laminar flow yields smoother particle motion, which makes it easier to estimate particle trajectories. (Of course, the processor may also be configured to estimate particle trajectories in certain turbulent flow regimes as well, provided that the sensor frame rate is fast enough to capture "smooth" sections of the particle trajectories.) If desired, the container can be agitated in manner that produces substantially laminar flow. For example, a spindle may rotate the container at a specific velocity (or velocity profile) for a specific time as determined from measurements of fluid behavior for different container sizes and shapes and/or different fluid levels and viscosities.

Figure 3A:
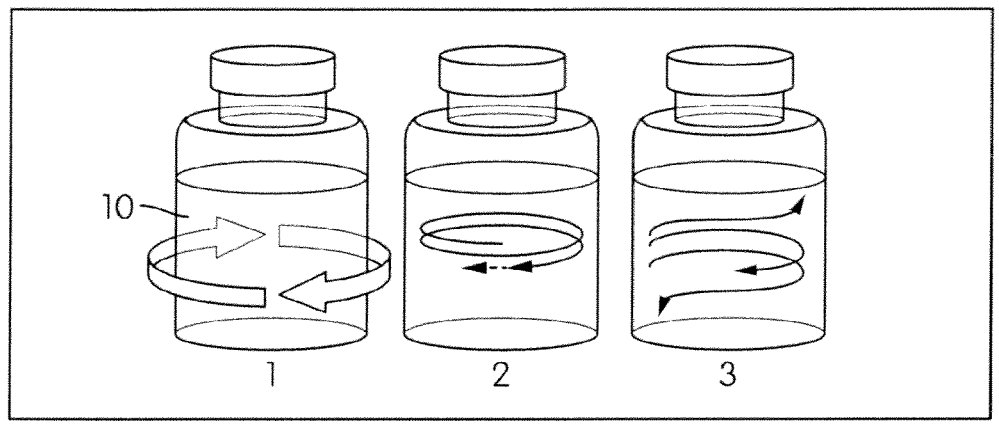
FIGS. 3A-3C illustrate three types of vessel agitation containing fluid and one or more particles in preparation from particle detection and identification: rotation of a cylindrical vessel (FIG. 3A), inversion and rotation of a syringe (FIG. 3B), and rocking of a syringe (FIG. 3C).
Figure 3B:
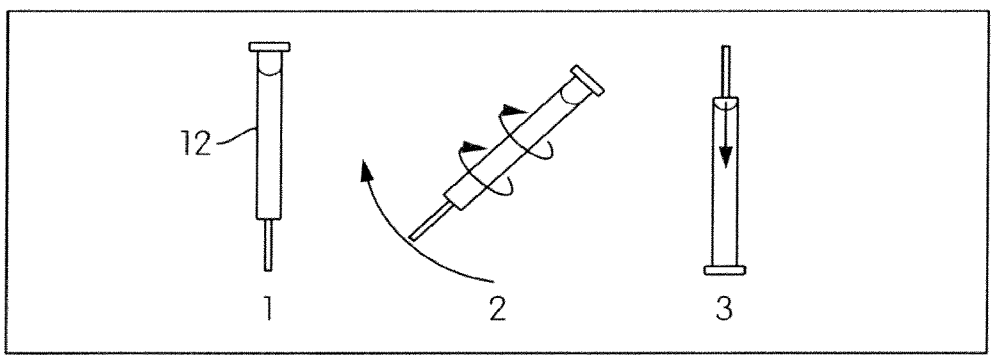
Figure 3C:
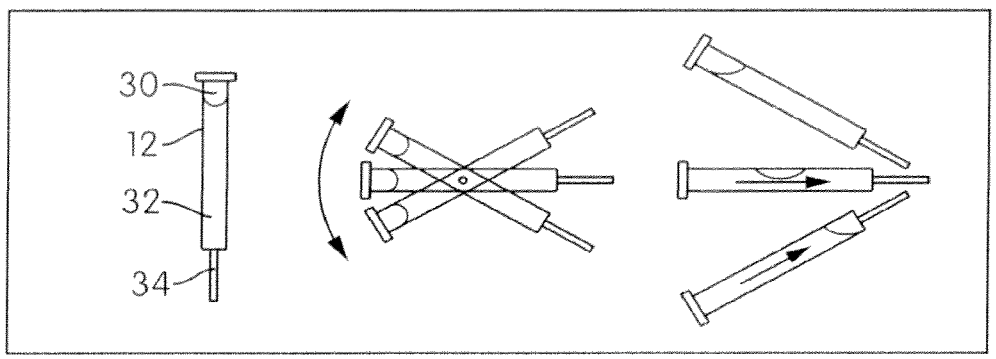

In one particular embodiment, a servo or stepper motor drives a spindle that holds a cylindrical container, causing the container to spin around its central axis, as shown in FIG. 3(*a*). Spinning the container 10 at sufficient speed causes even heavy particles (such as metal flakes) to rise from the bottom of the container 10 and into the fluid. For many fluids and particles, the motor drives a spindle holding the container 10 at 300 rpm for about three seconds. (Higher spin speeds may be required to energize heavy particles.) After three seconds of spin, the motor stops abruptly, and the fluid is allowed to flow freely in the now-static container. At this point, the imager 110 begins capturing video of the rotating fluid. The memory 140 records video for up to about seven to fifteen seconds, depending on the size of container under scrutiny (the memory 140 records less video of fluid in smaller containers because the fluid slows down more quickly in smaller containers due to the increased impact of wall drag).

In another embodiment, the spindle rotates the container 10 in a two-phase agitation/imaging sequence. In the first phase, the spindle spins the container 10 at 300 rpm for three seconds, causing less dense (and more delicate) particles, such as proteins, to become suspended in moving fluid. The imager 110 then captures video of proteins in the moving fluid. Once the imager 110 has collected enough time-series data, the second phase begins: the spindle rotates the container 10 at about 1600-1800 rpm for one to three seconds, causing denser particles, such as metal flakes, to become suspended in moving fluid, and the imager 110 captures time-series data representing the denser particles moving in the container 10. The high-speed rotation in the second phase may be intense enough to temporarily dissolve or denature the protein aggregates, which can re-form after the fluid slows or stops moving. The two-phase operation makes it possible to detect both dense particles that may not be energized by low-speed rotation and proteins that may be denatured by high-speed rotation.

Inventive systems may employ other rotation sequences as well, depending on (but not limited to) any of the following parameters: fluid viscosity, fluid fill level, fluid type, surface tension, container shape, container size, container material, container texture, particle size(s), particle shape(s), particle type(s), and particle density. For example, inventive systems may spin larger containers for longer periods of time before imaging the container contents. The exact agitation profile for a given fluid/container combination can be computed, characterized, and/or determined by routine experimentation.

If the visual inspection module uses a predetermined agitation sequence for a well-characterized container/fluid combination, it may trigger data acquisition only when the fluid (and suspended particles) are in a laminar flow regime. Alternatively, it may acquire additional time-series data, and the processor may automatically select start and end frames based on the container/fluid combination and/or agitation sequence.

In some embodiments, data acquisition may be triggered based on a detected characteristic of the fluid flow in the container. For example, as described in detail below, in some embodiments, it is possible to detect the meniscus of the fluid in the container and monitor the movement of the meniscus to determine when a vortex in the fluid relaxes post-spin. In some such cases the data acquisition may begin when the detected movement of the meniscus has returned to a substantially stable state.

Any of the visual inspection systems described above can also be used to detect and/or identify native and foreign particles in a syringe 12 that is at least partially filled with a drug product 32 or other fluid, as shown in FIG. 3B. Syringes 12 are often stored needle-down. As such, particulate may settle in the syringe's needle 34. To visualize these particles, a robot or person inverts the syringe 12—i.e., the robot or person rotates the syringe 12 by 180° about an axis perpendicular to its longitudinal axis so that the needle 34 points up. Particulate that has settled in the needle 34 falls vertically, enabling visualization by the imager 110. The robot or person may also spin syringe during the flip to fully mobilize the fluid.

Many syringes 12 have barrels with relatively small inner diameters (e.g., about 5 mm), which dramatically increases the effect of wall drag. For many drug products 32, the wall drag causes all rotational fluid motion to cease within approximately one second. This is a very short time window for practical particle analysis. Fortunately, rocking the syringe 12 gently about an axis perpendicular to its longitudinal axis, as shown in FIG. 3(*c*), yields particle motion that lasts longer than one second. The lateral rocking, which can be done with a robot or by hand, agitates particles through the motion of the syringe 12 and the motion of any air bubble(s) 30 oscillating within the barrel of the syringe 12. The visual inspection modules, units, and platforms described above are designed to be reconfigurable, and can accommodate this alternative method of agitation.

Once agitation is complete, the visual inspection system should remain still for the video recording phase. Because of the high resolution of the imagers typically employed, the spatial resolution of the images is very fine (e.g., about ten microns or less) and can be at least as fine as the diffraction limit. For certain configurations, a small (e.g., ten-micron) movement of the sample equates to a full pixel of movement in the detected image. Such motion compromises the effectiveness of static feature removal (background subtraction), which in turn degrades the performance of the analysis tools and the integrity of the output data.

With this in mind, vibration isolation is a key design consideration. In particular embodiments, the base of an illustrative visual inspection system is mechanically isolated from the laboratory environment, e.g., using vibration-dampening shocks, floats, and/or gaskets. Additionally, inside the unit, sources of vibration such as computers and robot controllers can be mechanically isolated from the rest of the system. Alternatively, data acquisition can be synchronized with residual motion of the container with respect to the imager or performed with a camera that performs pixel shifting or some other motion-compensating behavior. Such residual motion can also be recorded for postprocessing to remove deleterious effects of image motion.

Imager Configurations

Illustrative visual inspection systems can use standard, off-the-shelf imagers with any suitable sensor, including, but not limited to charge coupled device (CCD) or complementary metal-oxide-semiconductor (CMOS) arrays. The choice of sensor is flexible and depends somewhat on the requirements of the particular application. For instance, sensors with high frame rates enable the accurate mapping of the trajectories of fast-moving particles (e.g., in low-viscosity fluids). Sensitivity and noise performance are also important because many protein particles are transparent in solution and scatter light weakly, producing faint images. To improve noise performance, the sensor can be cooled, as understood in the art. For most applications, monochrome sensors offer the best performance due to slightly higher resolution over color cameras, as well as boasting higher sensitivity. For a small subset of applications, however, color sensors may be preferred because they capture the color of the particle, which may be very important in establishing its source (e.g., clothing fiber). In product quality investigation (also known as forensics), for instance, color sensors can be useful for distinguishing between different types of materials (e.g., fibers) in the manufacturing facility that can contaminate the drug product.

For complete container inspection, the imager's field of view should encompass the whole fluid volume. At the same time, the imager should be able to resolve small particles. Visual inspection systems achieve both large fields-of-view and fine resolution with large-format, high-resolution sensors, such as the Allied Vision Technologies (AVT) Prosilica GX3300 eight-megapixel CCD sensor, which has 3296× 2472 pixels. Other suitable sensors include the ACT Pike F505-B and Basler Pilot piA2400-17 gm five-megapixel cameras. When the imaging optics are chosen to fully image the fluid-bearing body of a 1 ml BD Hypak syringe, the AVT Prosilica GX3300 CCD sensor captures time-series data with a spatial resolution of approximately ten microns per pixel in both transverse dimensions. The combination of high speed and high resolution implies that recording the time-series data may involve large data transfer rates and large file sizes. As a corollary, the video compression techniques described below are specially designed to reduce data storage requirements while preserving the integrity of the fine detail of the particles captured in the image.

The collection optics that image the region of interest onto the sensor should be selected to provide a sharp images of the entire volume with a minimum spot size that is equal to or smaller than the pixel size of the sensor to ensure that the system operates with the finest possible resolution. In addition, the collection optics preferably have a depth-of-field large enough to fit the entire sample volume.

Figure 4:
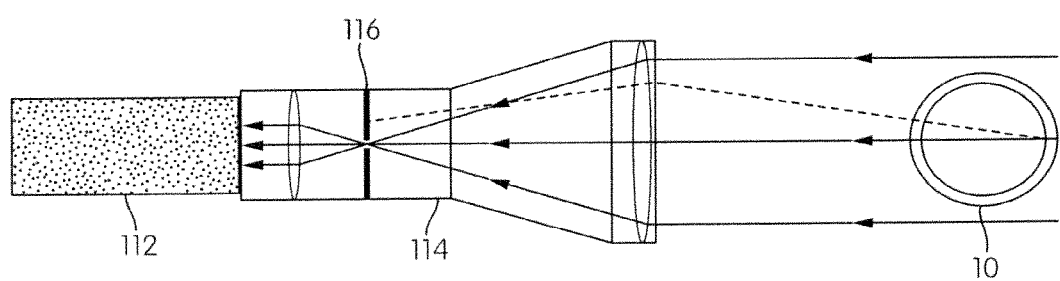
FIG. 4 is a ray optics diagram of a telecentric lens used to image a cylindrical vessel.

Telecentric lenses, such as the lens 114 shown in FIG. 4, are especially well-suited to visual inspection of fluid volumes because they are specifically designed to be insensitive to depth of field. As understood by those of skill in the art, a telecentric lens is a multi-element lens in which the chief rays are collimated and parallel to the optical axis in image and/or object space, which results in constant magnification regardless of image and/or object location. In other words, for an object within a certain range of distances from an imager with a telecentric lens, the image of the object captured by the imager is sharp and of constant magnification regardless of the object's distance from the imager. This makes it possible to captures images in which particles at the 'back' of the container 10 appear similar to those at the 'front' of the container 10. The use of a telecentric lens also reduces the detection of ambient light, provided a uniform dark backplane is used. Suitable telecentric lenses 114 include the Edmund Optics NT62-901 Large Format Telecentric Lens and the Edmund Optics NT56-675 TECHSPEC Silver Series 0.16× Telecentric Lens.

Container-Specific Blind Spots

Figure 5A:
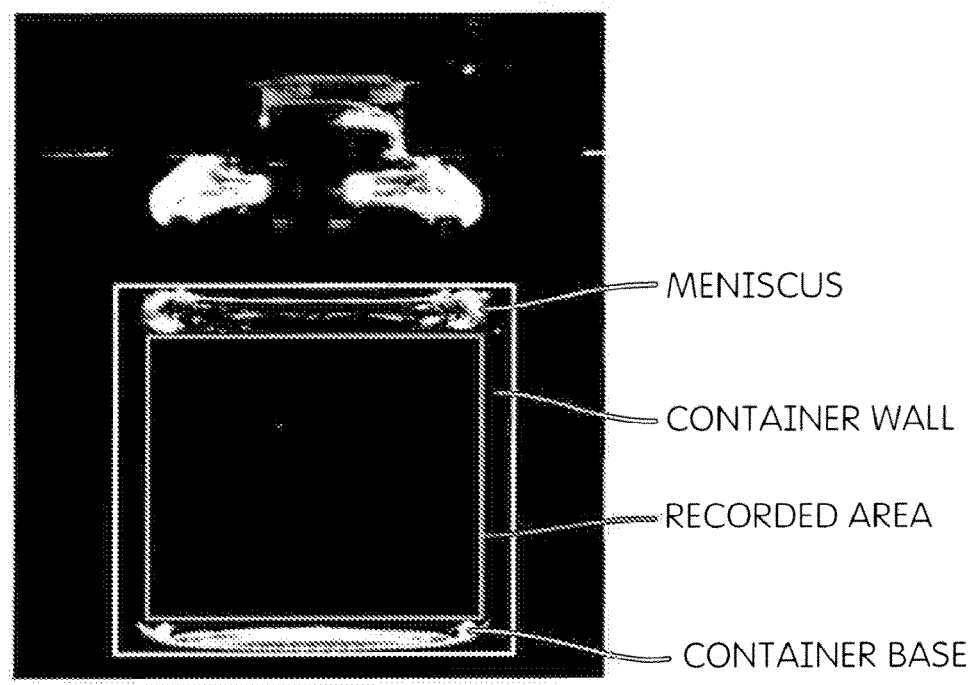
FIG. 5A shows the fluid meniscus and the recorded volume in a cylindrical vessel containing fluid.

One goal for almost any visual inspection system is to provide 100% container volume inspection. In reality, however, there may be fixed zones in which particles cannot be detected, as shown in FIG. 5A. First, the liquid around the meniscus may be difficult to incorporate in the analysis because the meniscus itself scatters light in a manner that potentially saturates the detector at that location, obscuring any particles or other features of interest. Second, for vials, the base of the container is typically curved at the corner, generally referred to as the 'heel'. The curved heel has the effect of distorting and ultimately obscuring any particles that venture sufficiently close to the bottom of the vial. Third, for syringes, the rubber plug features a central cone which intrudes slightly into the container volume. The tip of this cone can potentially hide particles, although it is small. The most subtle blind spots occur due to the curvature of the vial.

Figure 5B:
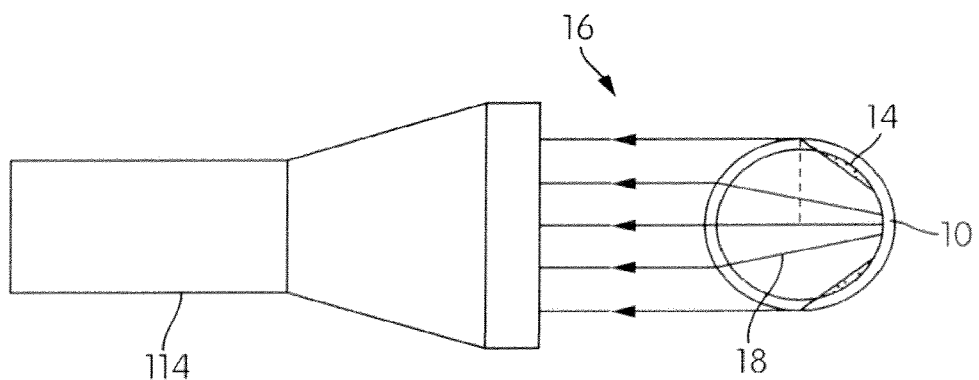
FIG. 5B illustrates distortion and blind spots in a cylindrical container created by the container's shape.

Cylindrical containers may also cause a lensing effect, shown in FIG. 5B, (indicated by bent rays 18) which serves to undermine the performance of the telecentric lens. The container's curved walls also create blind spots 14.

Figure 5C:
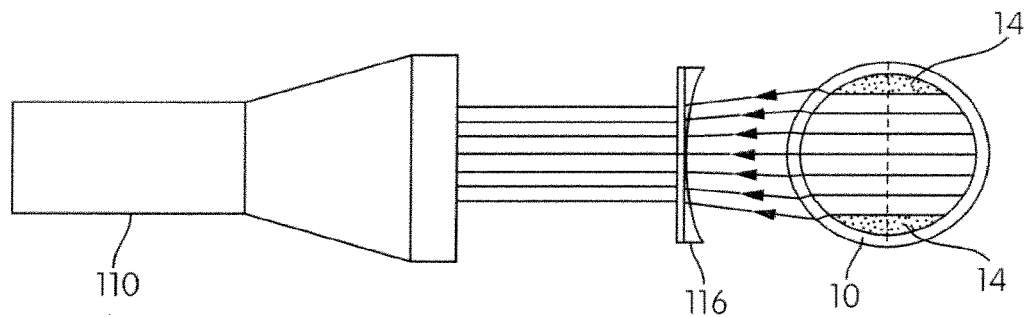
FIGS. 5C and 5D illustrate techniques to compensate for distortion and blind spots when imaging cylindrical vessels.
Figure 5D:
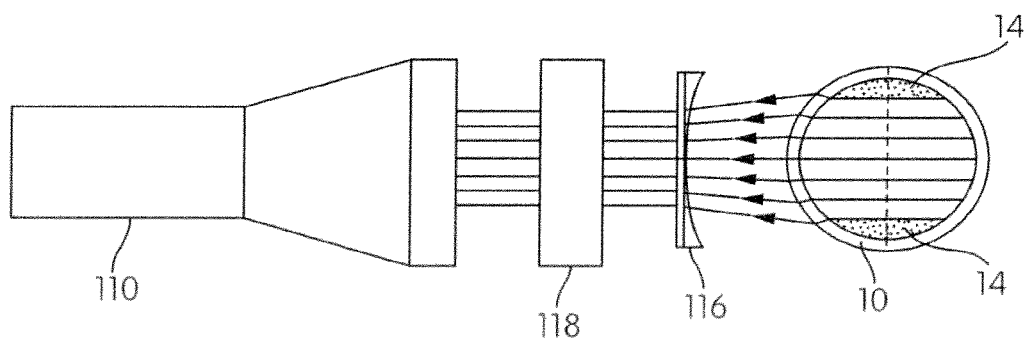
Figure 5E:
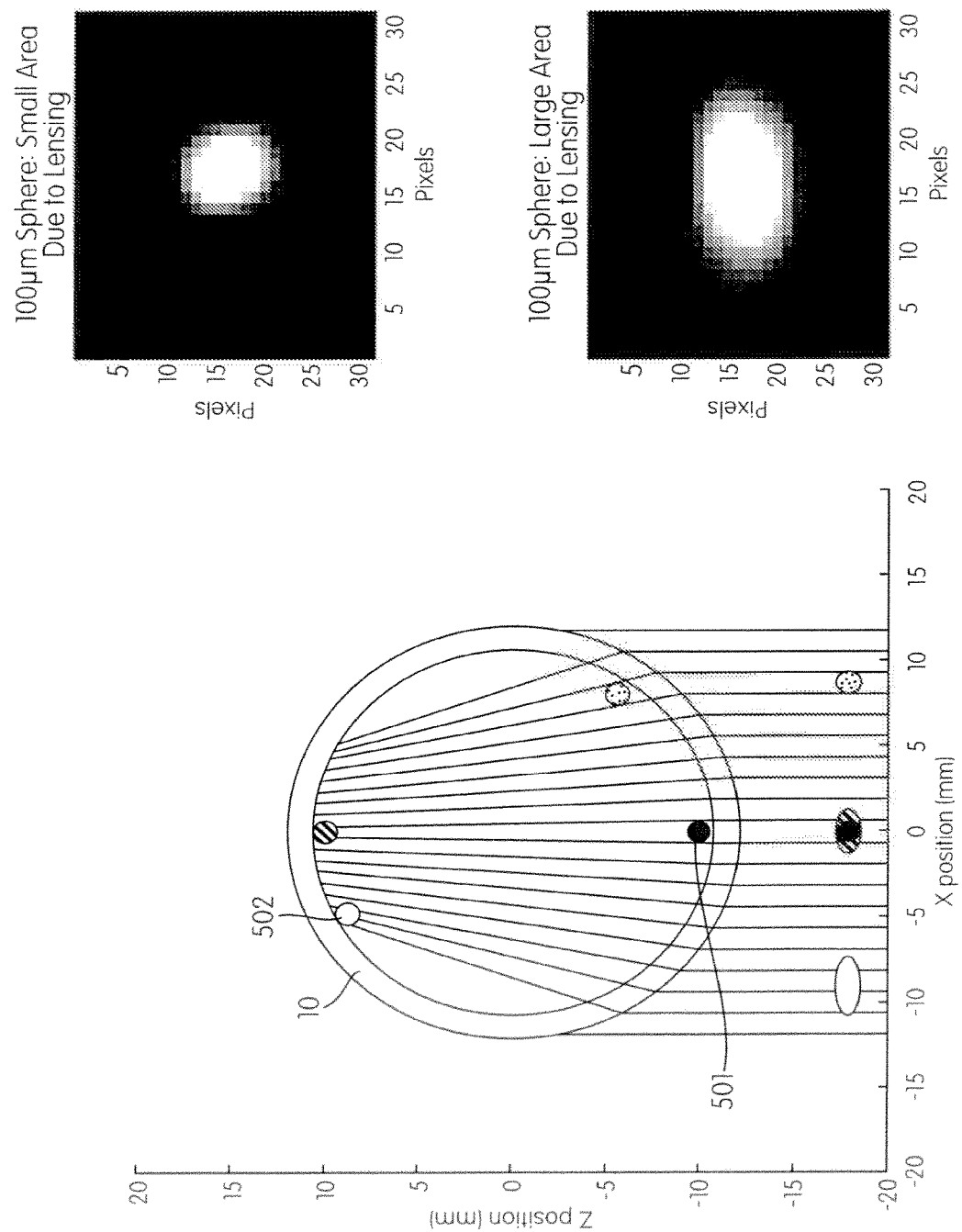
FIG. 5E illustrates the distortion and blind spots in a cylindrical container created by the container's shape for particles at various positions in the container.

FIG. 5E shows an example of the lensing effect cause by a cylindrical container 10. The camera/observer is at the bottom of the figure. As described above, a telecentric lens may be used when imaging particles in the container 10 to ensure that particles have a consistent appearance in the image that does not depend on their position in the container, that is, their distance from the camera. To accomplish this, in some embodiments, the depth of focus of the telecentric lens is chosen to be larger than the diameter of the fluid volume. In some embodiments, in the absence of a corrective optical element, the container curvature undermines this principle.

As shown, the shape and magnification of a imaged particle in the container 10 will depend on the position of the particle in the container. A particle 501 at the front-and-center of the container is not distorted at all (top inset). An identical particle 502 at the rear-and-side is distorted the most (bottom inset). Note that for a cylindrical container, the distortion occurs only along the horizontal axis (as is evident in the bottom inset).

To mitigate these effects, optional corrective optics, such as a corrective lens 116, are placed between the telecentric lens 114 and the container 10 as shown in FIG. 5C. Additional spatial correction optics 118 may provide additional compensation for distortion caused by the container's shape as shown in FIG. 5D. In various embodiments, any suitable corrective optical elements, e.g., tailored based on the curvature of the container 10 and/or the refractive index of the fluid, may be used in addition or alternative to the corrective lens 116 and optics 118.

Figure 5F:
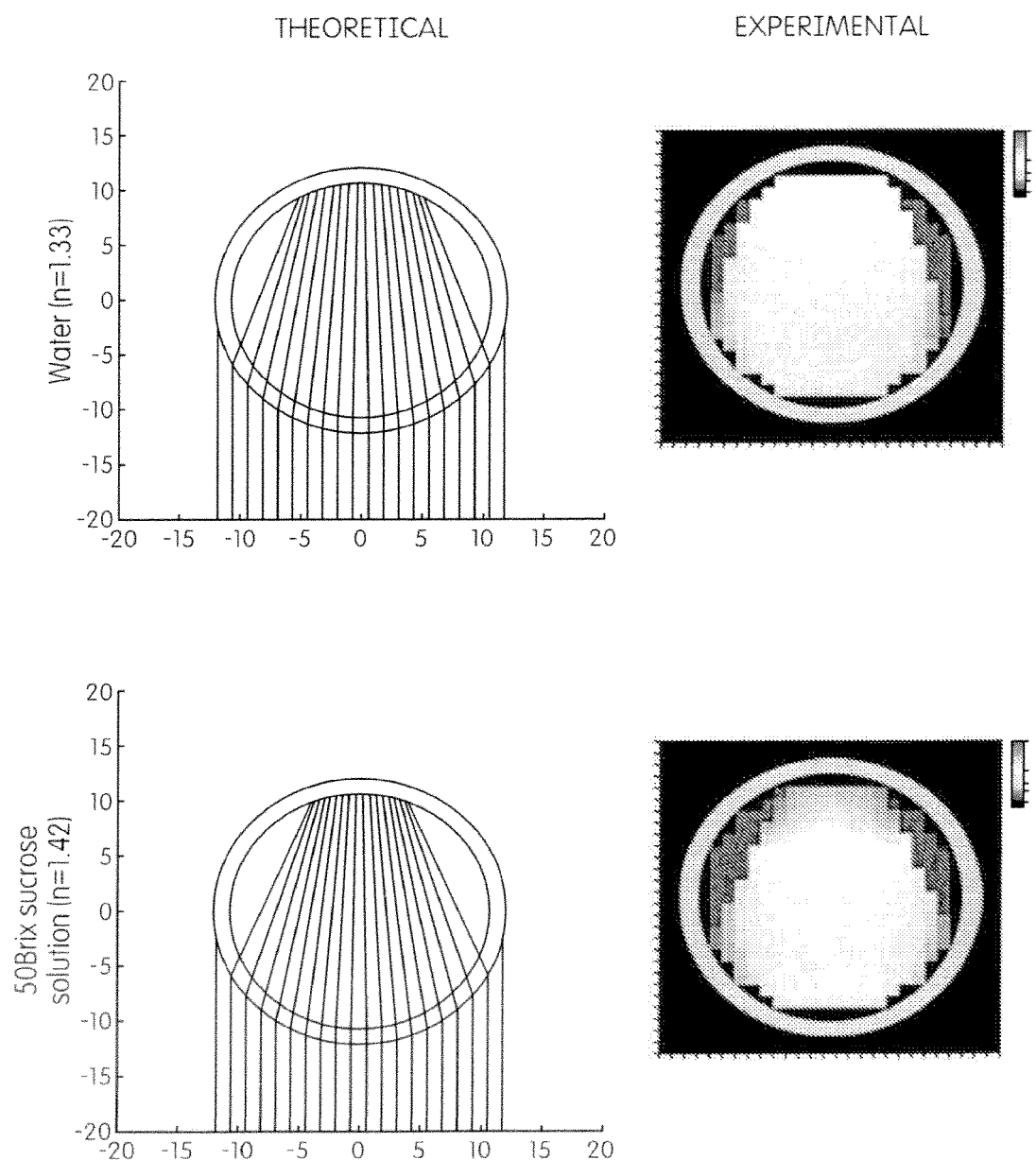
FIG. 5F illustrates theoretical models for distortion caused by a cylindrical container, each model corresponding to the same container but filled with a fluid with a different refractive index. The figure also shows corresponding experimental measurements confirming the theoretical models.

For example, in some embodiments, a model of the lensing effect caused by the cylindrical container 10 may be developed. The model may be based on a suitable set of parameters characterizing the optical distortion including, for example, the container outer diameter, container inner diameter, container refractive index, liquid refractive index, and wavelength of illumination light. The model may be developed using any suitable techniques know in the art including, for example, ray tracing techniques. FIG. 5F shows examples of theoretical models for the lensing effect for two different sets of container parameters (top left, bottom left), along with experimental data for the corresponding physical situations (top right, bottom right). As shown, the theoretical model and experimental data are in excellent agreement.

Figure 5G:
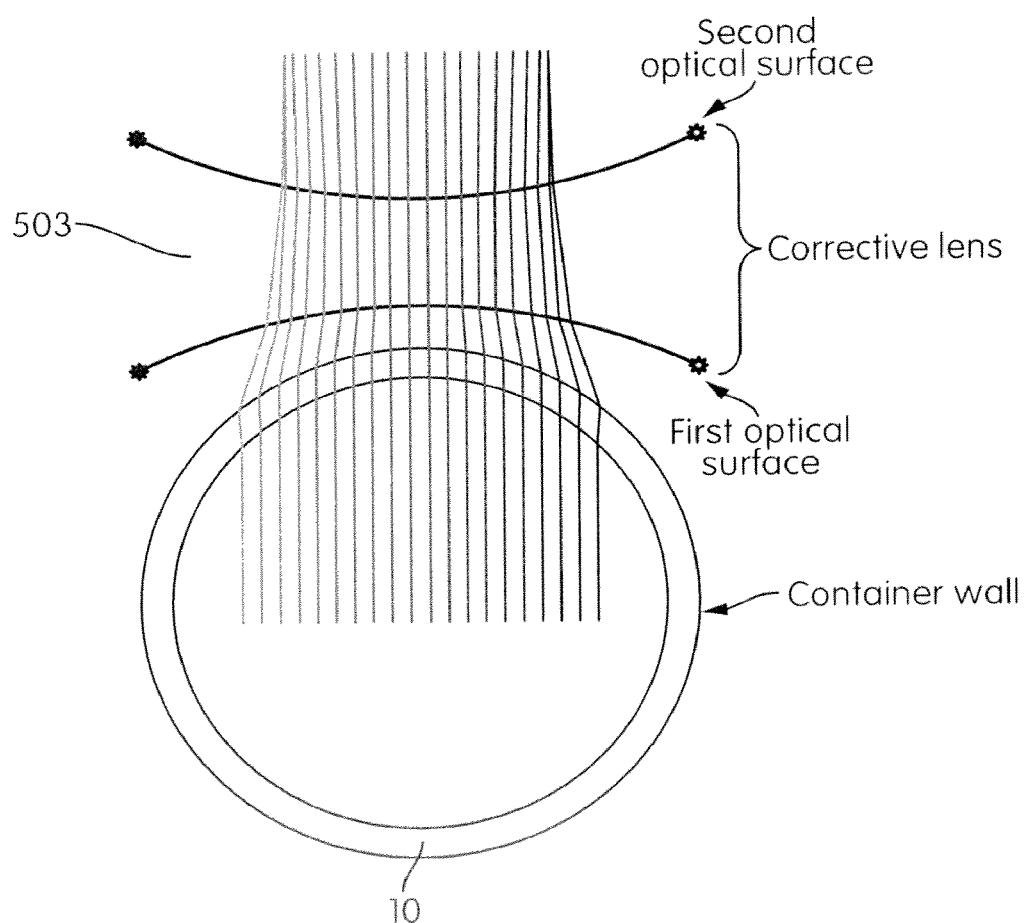
FIG. 5G illustrates the use of a corrective optical element to correct for distortion in a cylindrical container, created by the container's shape.
Figure 5H:
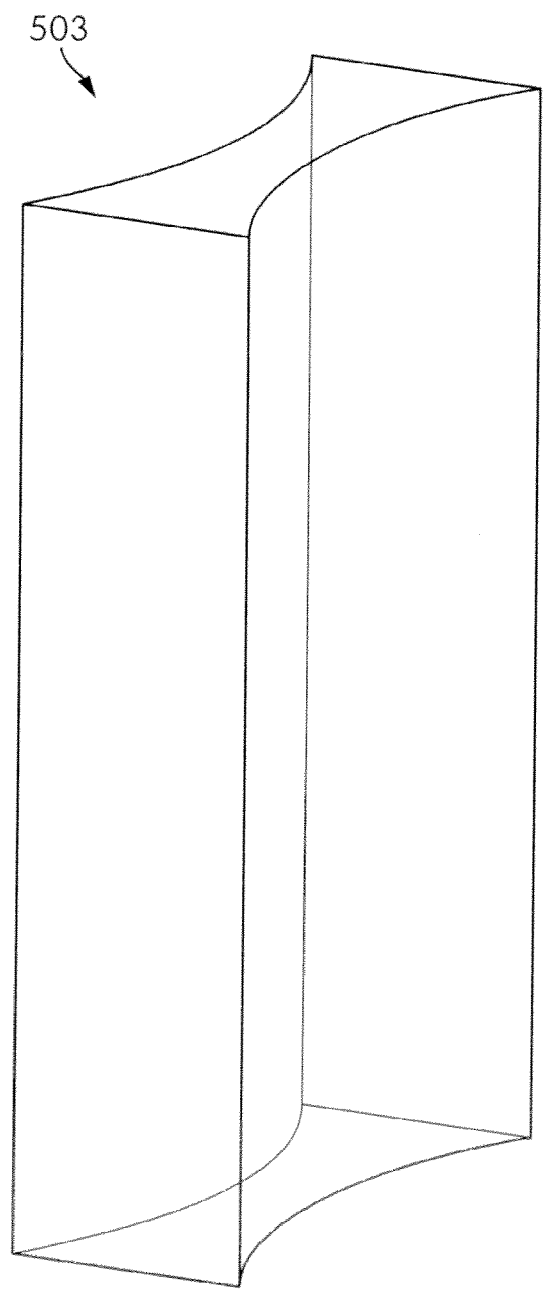
FIG. 5H is a detailed view of the corrective optical element of FIG. 5G.

Referring to FIGS. 5G and 5H, a corrective optical element 503 (as shown a lens) is used to correct for the lensing effect described above. The design of the corrective optical element may be based on a theoretical optical model of the container, experimental data indicative of the optical properties of the container, or combinations thereof. As shown, the corrective optical element 503 is made of a refractive material having cylindrical front and back surfaces. In some embodiments the design of the lens may be determined using free parameters including the radius of the front and back surfaces, the thickness of the lens, the refractive index of the lens, and the position of the lens relative to the container.

In some embodiments, other shapes can be used for the front and back surfaces of the lens, e.g., parabolic or arbitrary custom shapes. In some embodiments, relaxing the requirement that the surfaces be cylindrical will increase the size of the parameter space for the design of the corrective optical element 503 thereby allowing improved correction.

In some embodiments, the corrective optical element 503 may include multiple elements, thereby further increasing the design parameter space. In some embodiments, the corrective optical element 503 may correct for other types of optical distortion, aberration, or other effects. For example, in cases where illumination at multiple wavelengths is used, the corrective optical element 503 may be used to correct for chromatic aberration.

Figure 5I:
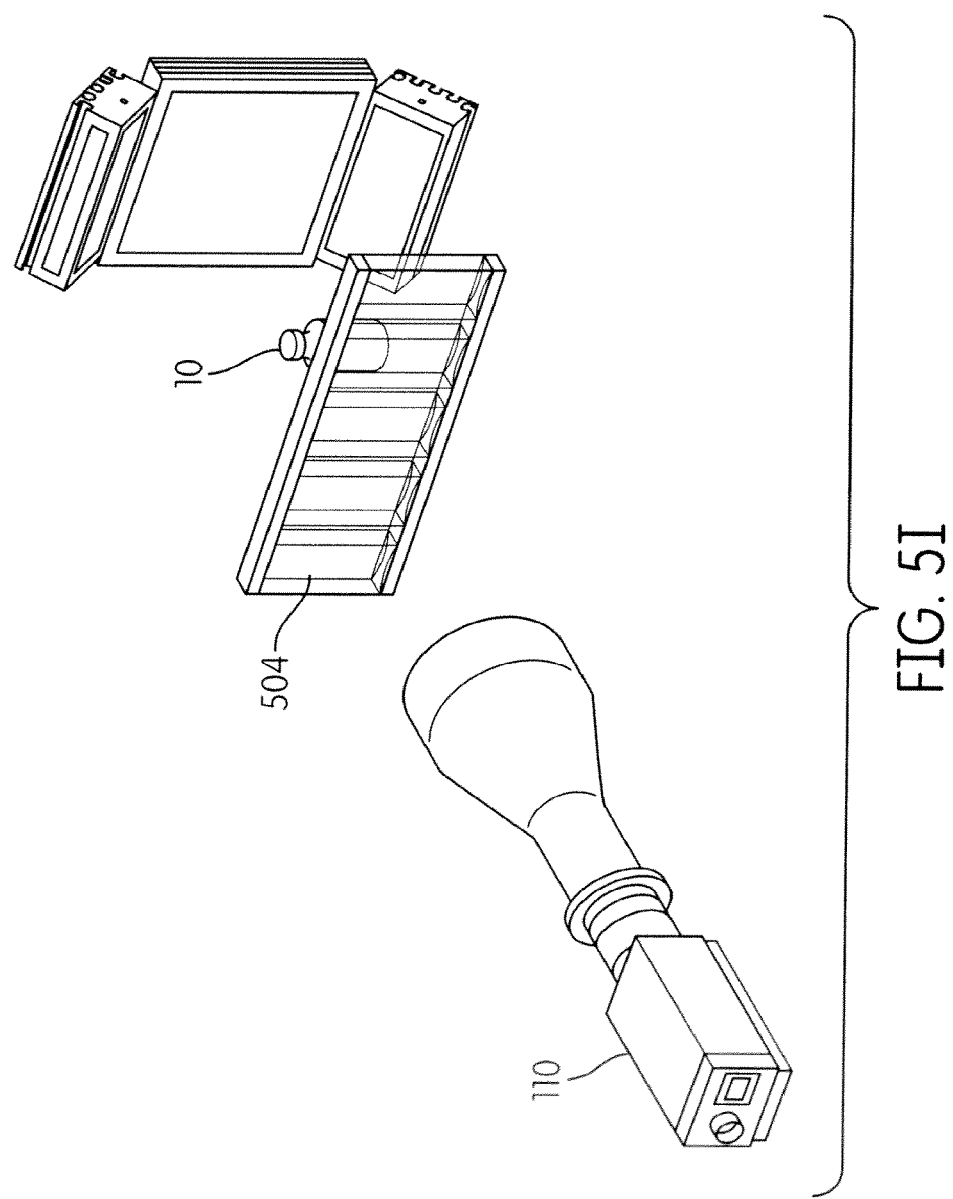
FIG. 5I illustrates a device for selecting one of several corrective optical elements.

In some embodiments, the corrective optical element 503 may be designed to correct for distortion caused by a particular container and/or fluid type. Because a single automated visual inspection unit 100 may be used with multiple container types, in some embodiments, it may be desirable to allow the corrective optical element 503 to be selectably changed to match the specific container 10 under inspection. For example, FIG. 5I shows a rack 504 that holds multiple corrective optical elements 503. The rack may be moved (manually or automatically) to place a selected one of the elements into the optical chain for an imager 110. Note that although a rack is shown, in various embodiments, any other suitable mechanism for selecting one optical element out of a set of multiple optical elements may be used.

Alternative visual inspection systems may include adaptive optics to compensate for distortion due to the container's curvature. For example, the telecentric lens 114 may be configured to capture an image of the container 10 reflected from a deformable mirror, such as a micro-electrical-mechanical system (MEMS) mirror. The sensor 112 uses the background data to derive the nature and magnitude of the aberrations resulting from surface curvature, surface defects, and other imperfections in the container 10. The sensor 112 feeds this information back to the deformable mirror, which responds by adjusting its surface to compensate for the aberrations. For example, the deformable mirror may bend or curve in one direction to compensate for the container curvature. Because the deformable mirror responds dynamically, it can be used to compensate for aberrations specific to each individual container 10.

In addition, particle tracking can be tuned to detect particle disappearance in conjunction with the known locations of these blind spots, allowing the program to predict if and where the same particle might re-appear later in the video sequence as described below.

Additional techniques for dealing with blind spot related issues (e.g., using multiple imagers) are described below.

Camera Frame Rate

Effective particle tracking using the nearest-match (greedy) algorithm described below can be considered as a function of three primary factors: the camera capture rate (frame rate), the particle density (in the two-dimensional image) and the typical particle velocity. For truly effective tracking using the nearest-match algorithm, the camera should preferably be fast enough to meet the criterion:

$$\text{Camera rate} > \frac{\text{Maximum particle velocity}}{\text{Minimum interparticle separation distance}}.$$

In reality, when projecting a three-dimensional volume onto a two dimensional image, it is possible for particles to appear to be very close to one another (even occluding one another) when in fact they are well spaced in the container. When taking this into account, it makes more sense to consider the mean nearest-neighbor distance than to consider the apparent minimum interparticle separation distance. Note that here that nearest-neighbor distance is the distance between adjacent particles in a given frame of time-series data, while nearest-match distance refers to the distance between the difference in position observed for a single particle in consecutive frames of time-series data. Rewriting the criterion for camera speed in terms of nearest-match distance gives:

$$\text{Camera rate} > \frac{\text{Maximum particle velocity}}{\text{Minimum interparticle separation distance}}.$$

Alternative visual inspection systems may use predictive tracking techniques instead of nearest-match (greedy) particle tracking techniques. Predictive techniques use knowledge of a particle's known trajectory, in conjunction with knowledge of the spatial constraints of the container and the expected fluid behavior, to make estimate the particle's most likely position in a subsequent frame. When properly implemented this approach can more accurately track particles moving through densely populated images at speed.

When attempting to detect and measure very small particles in relatively large containers, it is advantageous to maximize the spatial resolution of the image sensor. In general, this has the direct effect of lowering the sensor's maximum achievable frame rate.

Visual Inspection with Multiple Imagers

The use of a single camera may compromised by the presence of known blind spots. Additionally, mapping a three-dimensional particle distribution onto a two-dimensional image can result in ambiguity due to occlusion (e.g., as shown in FIG. 5E, where a particle at the back center of the container is occluded by a particle at the front center). Alternative visual inspection systems (e.g., as seen in FIG. 6) can, in principle, resolve this problem by correlating results from two or more imaging systems. By correlating positional trajectory information from two or more cameras it is possible to construct detailed three-dimensional trajectory maps, which may be more robust and less prone to errors caused by occlusion (discussed below) than two-dimensional trajectory maps.

Increasing the spatial resolution of the imager also limits the data acquisition rate (frame rate) for a given particle concentration and particle speed. When inspecting unknown containers, there can be no guarantee the particle concentration will be suitably low. At the same time, in order to suspend heavy particles such as glass or metal in the fluid, rotation rates in the container may need to be quite high, resulting in high particle velocities in the captured video stream. One way to resolve this conflict is to employ the novel imaging hardware configurations described below. Assuming the best commercially available sensors are already being employed, and the particles in the container are scattering a sufficient amount of light, it is still possible to increase the data acquisition rate by multiplexing two or more sensors, with constant, reliable triggering from a dedicated trigger source.

In addition, exemplary visual inspection systems can be configured to provide spatial resolution finer than 10 microns by relaxing the requirement for full container inspection, and instead consider only a subset of the volume. In general, for sub-visible particles, especially protein aggregates, this is acceptable because smaller particles tend to occur in higher numbers and be more homogenously distributed throughout the volume. Alternatively, exemplary visual inspection systems can provide both full container inspection and fine spatial resolution by using multiple imagers with different magnifications to acquire both wide-area and fine-resolution time-series data in parallel.

Figure 6B:
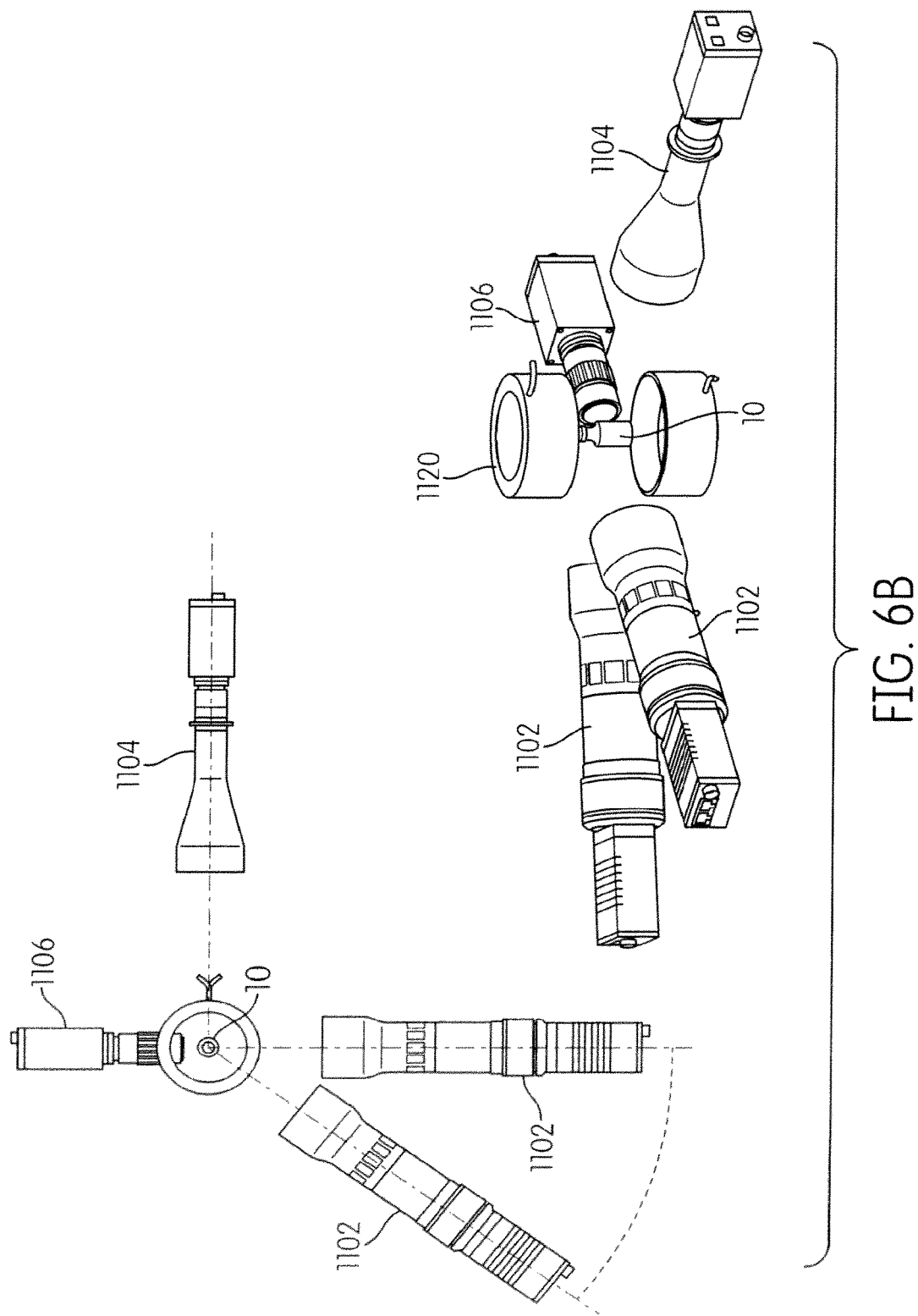

Alternative magnifications can be used simultaneously, e.g., as in FIG. 6A, with one imager 1102 to look at the full container, and a second imager 1104 with higher magnification (e.g., a long-working distance microscope objective) to zoom in on a smaller sub-volume and examine, for instance, very small particles (e.g., particles with diameters of about ten microns, five microns, one micron or less). Other visual inspection systems may include multiple imagers 1102, 1104, and 1106 disposed about a container 10 illuminated by one or more rings of light-emitting diodes (LEDs) 1120 mounted above and below the container 10 as shown in FIG. 6B. Identical imagers 1102 mounted at different position provide binocular vision. An imager 1104 with a long-working-distance microscope objective provides fine resolution for a subvolume of the container 10, and an imager 1106 with an alternative sensor (e.g., an infrared sensor, bolometer, etc.) provides additional time-series data.

Figure 6C:
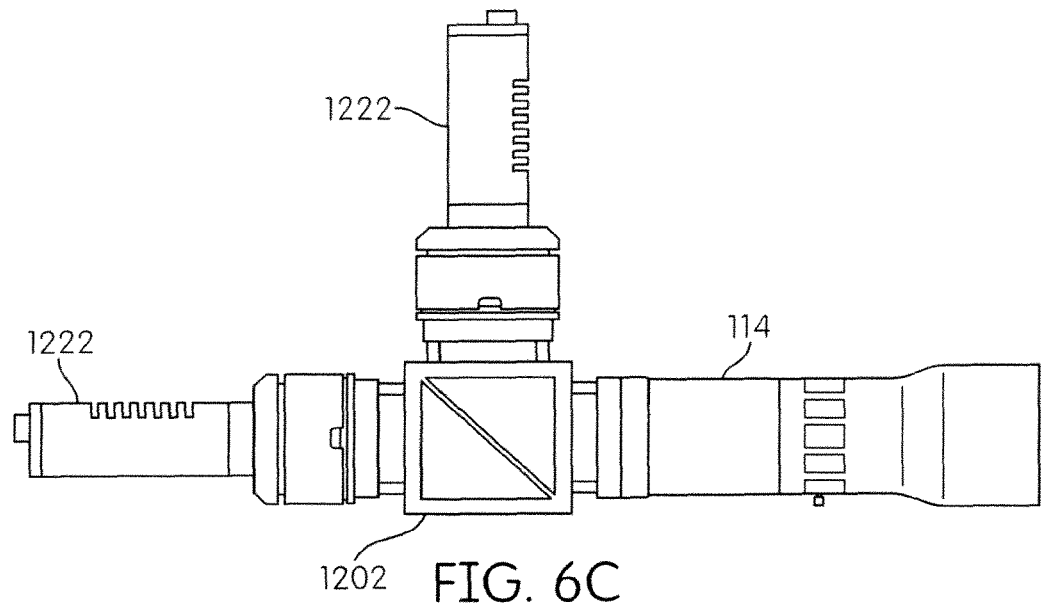
Figure 6D:
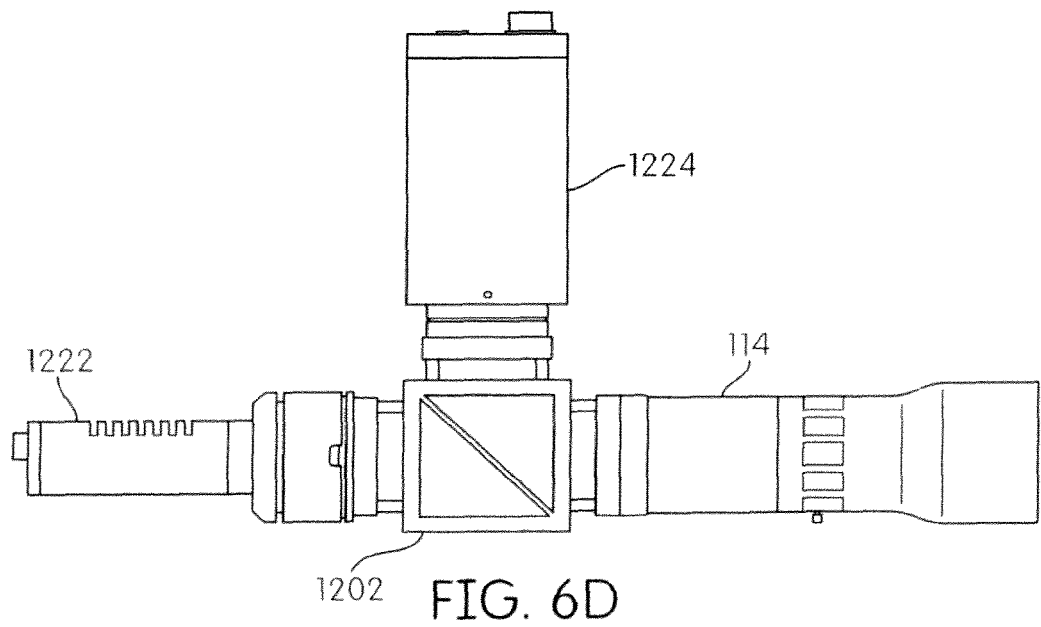

FIGS. 6C and 6D show alternative imaging configurations that harness the properties of telecentric imaging. At the back aperture of the telecentric lens, a 50/50 beamsplitting cube 1202 splits the projected image into two separate imaging arms. Each imaging arm may include a high-resolution, low-speed sensor 1222 that operates in interleaved fashion with the sensor 1222 in the other arm as shown in FIG. 6C to double the frame rate. That is, running the two sensors 1222 simultaneously with a half-cycle relative phase offset improves temporal resolution by a factor of two. The image streams can then be combined to provide a single movie at double the nominal sensor frame rate.

Alternatively, each arm may include a different sensor as shown in FIG. 6D, e.g., to compensate for a tradeoff in imaging sensor arrays: the finer the camera resolution, the slower the camera's maximum possible frame rate (e.g., 10-50 or 15-25 frames per second at full resolution, 50-200 frames per second at low resolution, etc.). For accurate particle tracking, the dominant sensor performance parameter is high temporal resolution (high frame rate). For accurate particle sizing, however, the dominant sensor performance parameter is fine spatial resolution (as many pixels as possible in the image). At present, the primary limiting factor on the spatial resolution and data transfer rate is the data transfer bus. Available imagers can acquire time-series data of a four-centimeter tall container with a spatial resolution of about ten microns per pixel and a data transfer rate of about twenty-five frames per second for a standard personal computer bus (e.g., a dual GigE or CameraLink bus).

FIG. 6D illustrates one way to achieve fast frame rates and fine resolution: image the fluid with both a high-resolution, low-speed sensor 1222, and a sensor 1224 with a more modest spatial resolution, but a higher frame rate. External triggering can ensure the two cameras are synchronized in a commensurate fashion. Because the cameras are viewing copies of the same image, their data can be directly correlated to produce improved particle analysis.

Figure 7A:
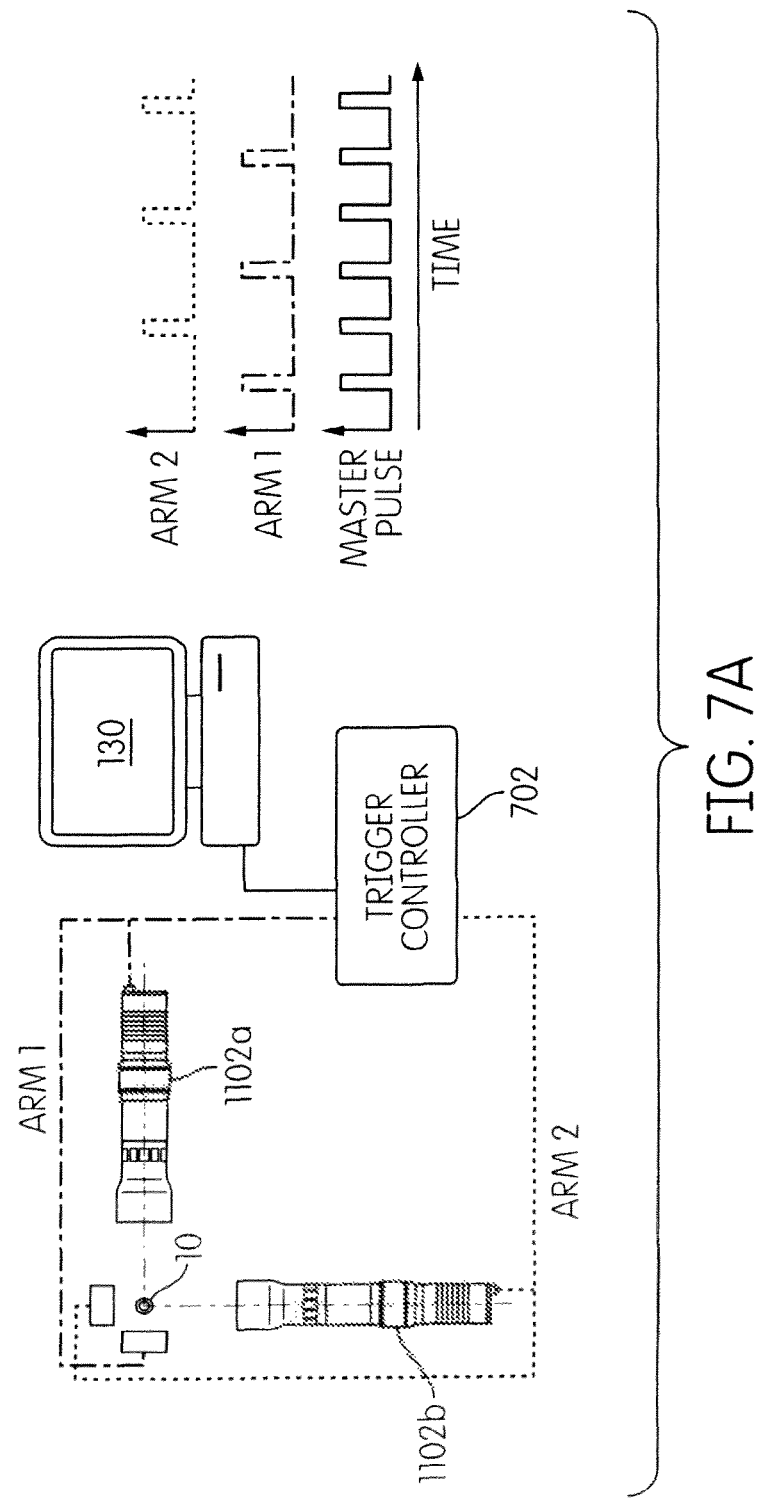
FIGS. 7A and 7B illustrate triggering of image acquisition and illumination for imaging particles with dual-sensor imagers.
Figure 7B:
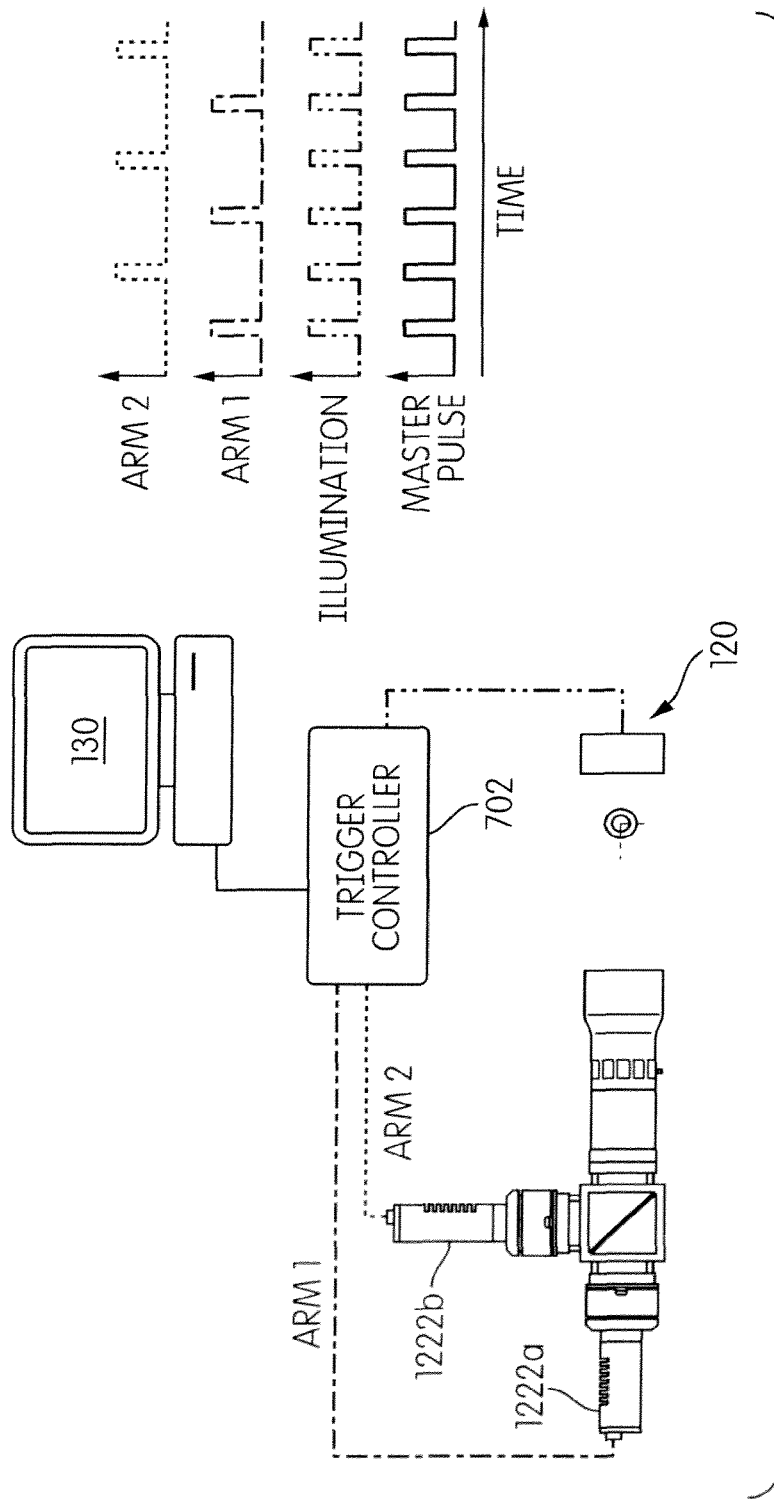

FIGS. 7A and 7B illustrate timing and control of illumination sources 120 and multiple cameras. In both FIG. 7A and FIG. 7B, a trigger controller 702 emits two trigger signals—labeled ARM 1 and ARM 2 in FIGS. 7A and 7B—derived by decimating a master pulse signal. The ARM 1 trigger signal drives a first camera (1102*a* in FIG. 7A, 1222*a* in FIG. 7B) and the ARM 2 trigger signal drives a second camera (1102*b* in FIG. 7A, 1222*b* in FIG. 7B) in interleaved fashion. That is, the trigger signals causes the first and second cameras to acquire alternating sequences of frames. The trigger controller 702 may also drive the illumination source 120 with an illumination signal that causes the illumination source 120 to illuminate the container every time the first or second camera acquires an image. Other trigger sequences are also possible; for example, the trigger controller 702 may drive additional cameras and/or combinations of high- and low-resolution cameras that acquire images at different frame rates.

Other arrangements are as possible, as evident to those of skill in the art. For instance, the image sensors on each arm may be equivalent to each other, but the collection optics may be different. One arm may include extra image magnification optics to 'zoom in' on a particular subset of the image, providing a simultaneous wide-field and magnified view.

Illumination Configurations

The inventive visual inspection systems harness the manner in which various particles interact with light to detect and identify particles in fluid-bearing containers. The interaction of a particle with light is a complex function of a number of factors, including the particle's size, shape, refractive index, reflectivity and opacity. Proteinaceous particles may primarily scatter light through refraction, while laminar glass particles may predominantly reflect light. Some particles, for example collagen fibers, can modify intrinsic physical properties of the light, such as a rotation of polarization. Tailoring the detector, particle, and light geometry to maximize contrast between various particle types can lead to highly accurate detection and differentiation.

FIGS. 8-12 show various illumination configurations that are tailored or can be switched/actuated among different illumination modes for specific types of particle, container, and/or fluid. For example, the light sources may illuminate the particles in such as way as to maximize the amount of light they reflect or refract towards the detector, while keeping the background dark to maximize the contrast between the images of the particles and the background. In addition, the sources may emit radiation at any suitable wavelength or range of wavelengths. For example, they may emit broadband white light (390-760 nm), a narrowband beam (e.g., at 632 nm), or even ultraviolet or X-ray radiation. Suitable ranges include 10-3000 nm, 100-390 nm (ultraviolet), 390-760 nm (visible), 760-1400 nm (near infrared), and 1400-3000 nm (mid-wavelength infrared). X-ray emissions (<10 nm) are also possible. When taken as a complete ensemble, the array of lighting options disclosed herein allows inventive visual inspection systems to detect and identify the full range of particles that can potentially appear in drug products.

Because some particles scatter only very weakly, it is often beneficial to irradiate the sample with as much light as possible. The upper limit of the sample irradiance is primarily driven by the photosensitivity of the product under examination. A judicious choice of wavelength may also be necessary, particularly for biological products; the exact choice depends on the product being illuminated. Monochromatic red light centered around 630 nm represents a 'happy medium' and is an easily available wavelength in terms of affordable light sources.

LED arrays, such as the LDL2 series LED arrays from CCS Lighting, are effective for illuminating particles seen in pharmaceutical products; however, collimated laser beams could also be used. In some cases, illumination optics may pattern or shape the illumination beam to be collimated inside the fluid volume (as opposed to outside the container). For alternative light sources, if heating from the light source is a concern, light can be delivered to the inspection area through the use of optical waveguides or optical fibers 124 as shown in FIG. 8.

The illumination wavelength can be chosen based on the absorption and/or reflectivity of the fluid and/or particles being analyzed; this is especially important light-sensitive pharmaceutical products. Red light (630 nm) offers a good balance between low absorption by the protein and low absorption by water. Strobing the illumination in sync with the times-series data acquisition further protects the integrity of light-sensitive pharmaceutical products by minimizing the products' exposure to incident light. Strobing has two further advantages: LEDs operate more efficiently when run in this manner, and strobing reduces the effect of motion blur, which left unattended compromises particle size measurements as described below.

Figure 8:
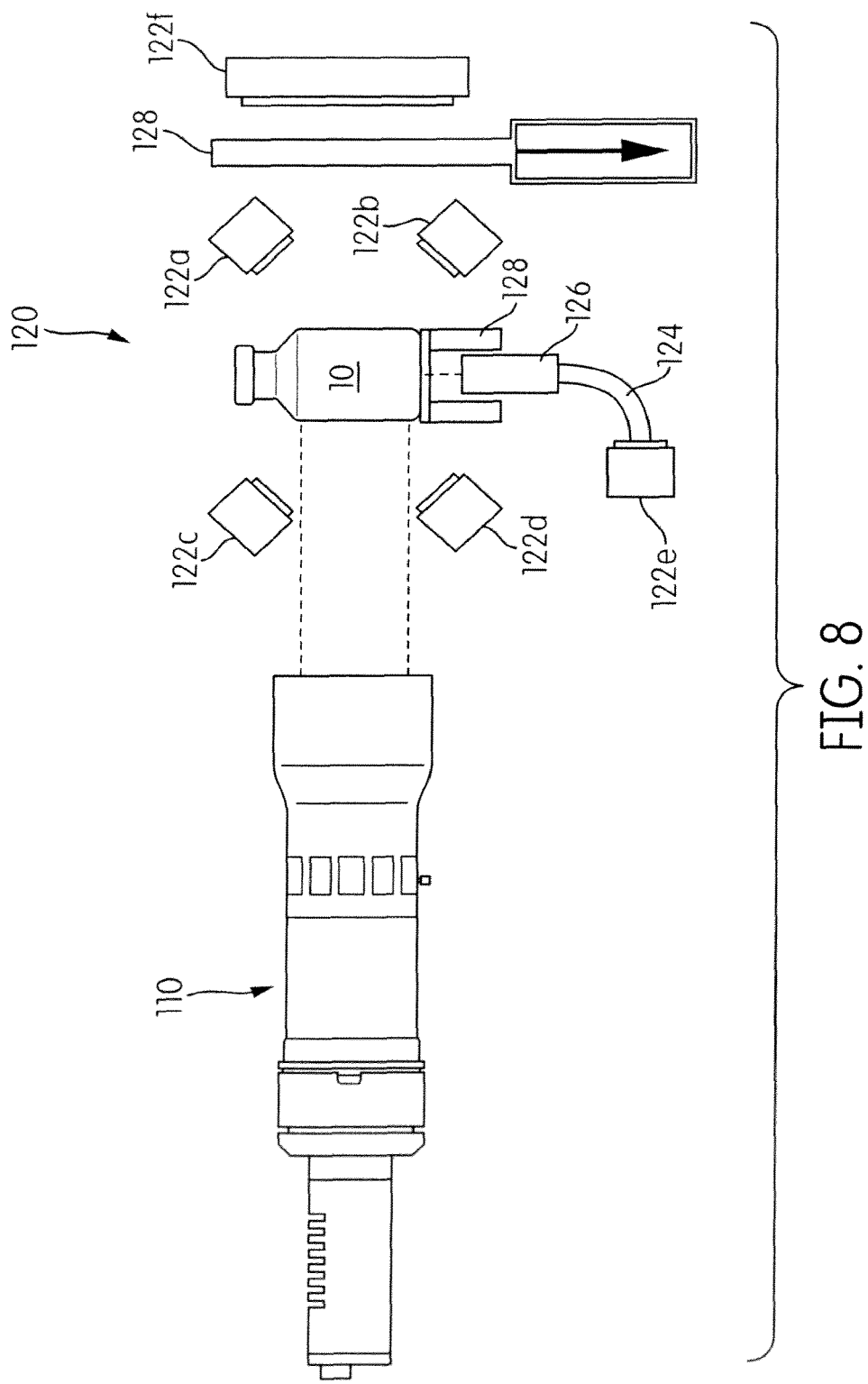
FIG. 8 is a schematic diagram of an flexible, multipurpose illumination configuration that includes light sources positioned before, behind, and below the vessel being inspected.

FIG. 8 shows an exemplary reconfigurable illumination system 120 that includes several light sources 122*a*-122*f* (collectively, light sources 122), which may be LEDs, lasers, fluorescent or incandescent bulbs, flash lamps, or any other suitable light source or combination of suitable light sources. Light sources 122 may emit visible, infrared, and/or ultraviolet radiation. They may be narrowband or broadband as desired, and can be filtered using appropriate optical filters or polarizers. In FIG. 8, for example, a polarizer 126 polarizes light emitted by the light source 122*f* that backlights the container. In addition to the backlight 122*f*, the illumination system 120 includes four lights sources 122*a*-122*d* at corners of rectangular prism around the container 10. Another light source 122*e* illuminates the container 10 from the bottom via an optical fiber 124 coupled to a collimator 126 pointing at the bottom of the container 10. In some cases, the fiber 124 and collimator 126 may be housed inside a hollow shaft 128 of the spindle used to rotate the vessel.

The multiple light sources 122 shown in FIG. 8 can be used to determine the optical properties of a given particle for differentiation based on the given particle's interaction with light. As understood by those of skill in the art, different particles interact with light in varying manners. Common modes of interaction include scattering, reflecting, occluding, or rotating the polarization of the light, as shown in TABLE 1, where "X" indicates that a particle of this type will show up using a given lighting technique, as exemplified in FIGS. 9A-9D and FIG. 11 (described below). An "M" indicates that particles of this type might show up using a given technique, but could still potentially be detected/ differentiated using post-processing image segmentation and feature identification techniques.

TABLE 1

Light Interaction for Various Particle Types

| | Particle Type | | | | |
|---|---|---|---|---|---|
| | Protein | Lamellae | Opaque | Cellulose | Air |
| | | | Primary Interaction | | |
| Lighting Technique | Scatter | Reflect | Occlude | Polarization Change | Scatter |
| Rear Angle | X | X | X | X | X |
| Bottom | | X | M | | |
| Backlight | | | X | | |
| Polarizing | | M | M | X | M |

Figure 9A:
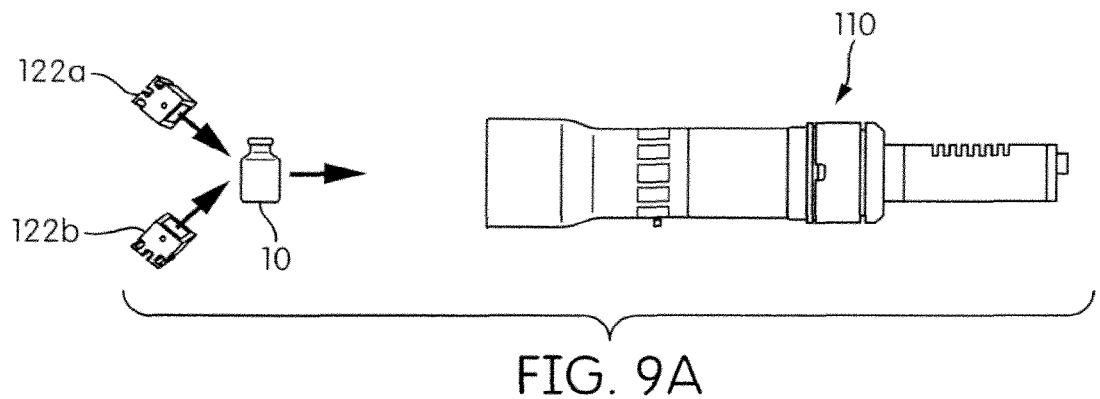
FIGS. 9A-9C illustrate illumination from different angles for distinguishing between different particle species using the light sources shown in FIG. 8.
Figure 9B:
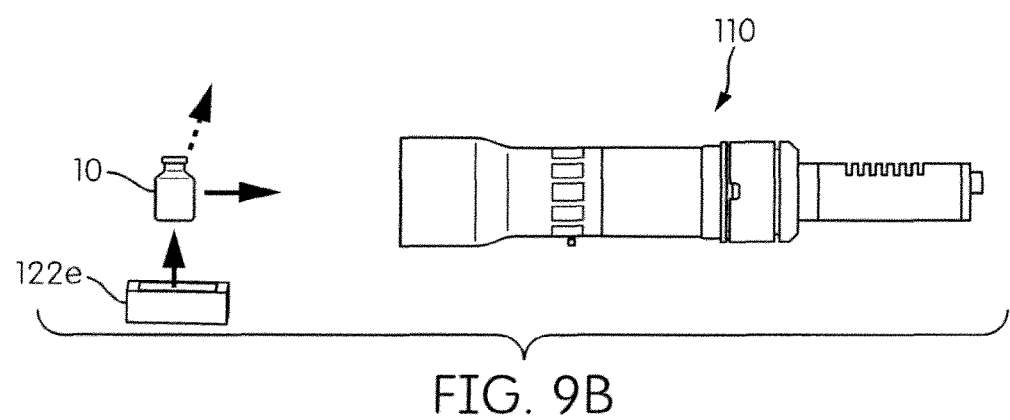
Figure 9C:
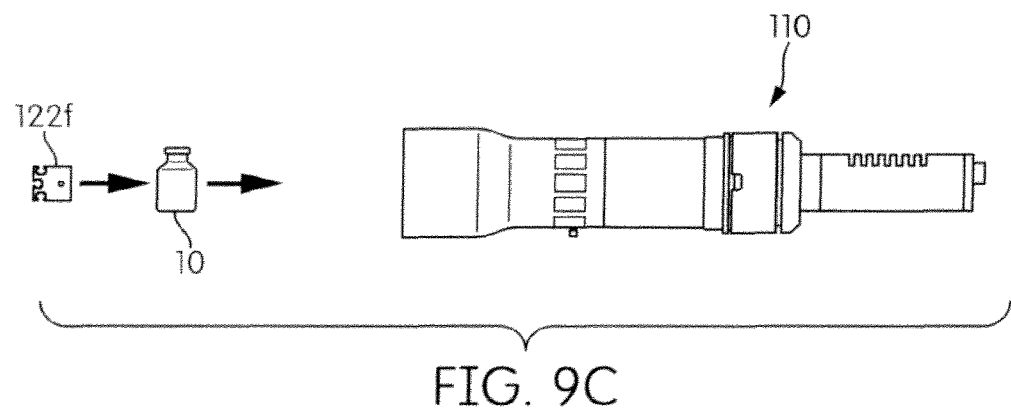

FIGS. 9A-9C illustrate different illumination patterns that can be implemented with the illumination system 120 of FIG. 8 (some light sources 122 are omitted for clarity) to differentiate particle type based on light interaction. In FIG. 9A, light sources 122a and 122b provide rear angled lighting, which is useful for showing proteins, as well as most particle types that scatter light. In FIG. 9B, Light source 122e provides bottom light, which is useful for showing reflective particles, such as glass lamellae, that reflect light towards the imager 110 (horizontal arrow); particles that scatter but do not reflect light (e.g., proteins), may not show up on the sensor (diagonal arrow). In FIG. 9C, light source 122f provides uniform backlight, which is useful for showing particles that occlude the light, such as metal, dark plastic, and fibers. Those of skill in the art will readily appreciate that other light sources and/or illumination patterns and sequences are also possible.

Figure 9D:
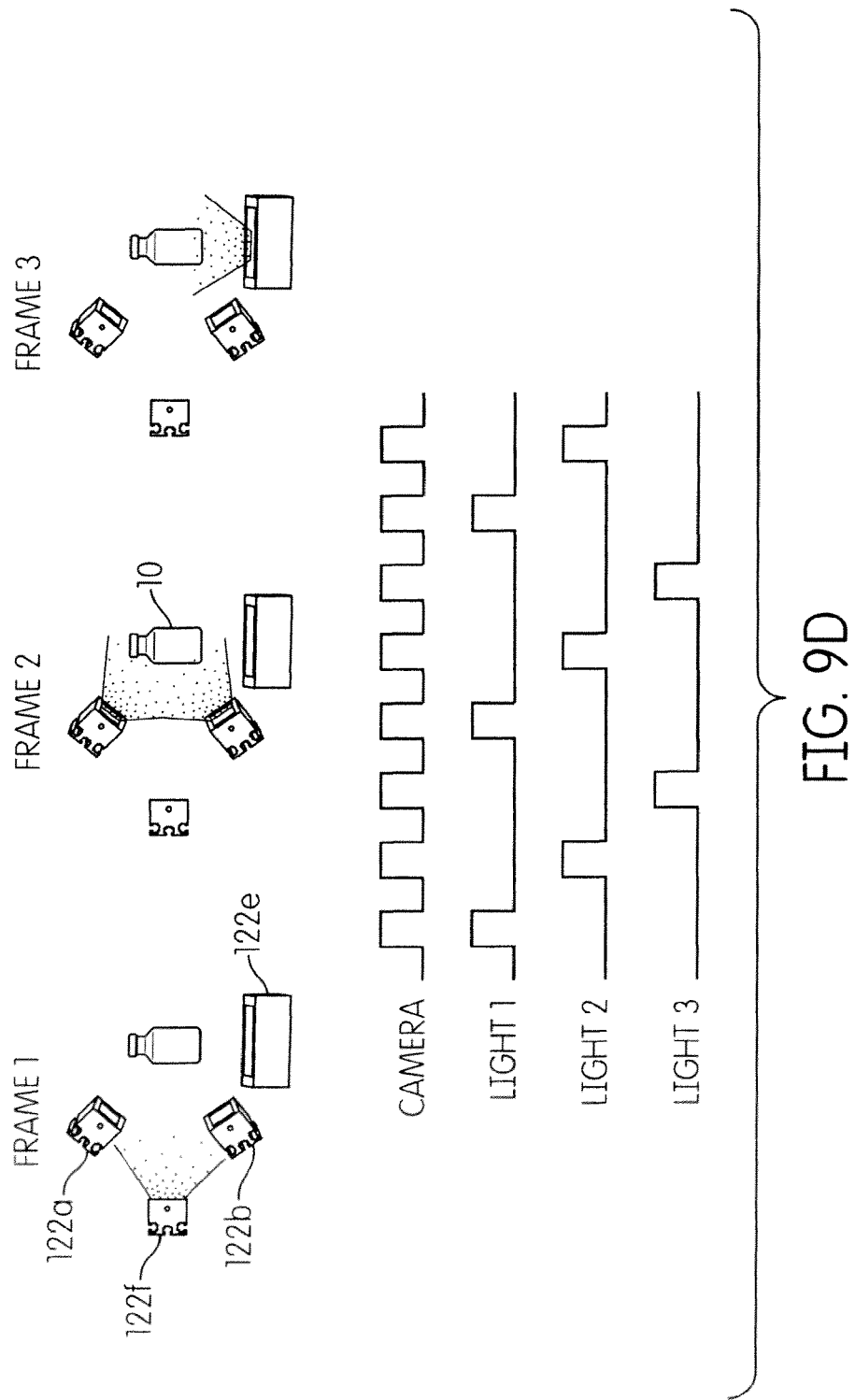
FIG. 9D shows an illumination sequence and timing diagram for using the configurations of FIGS. 9A-9C to distinguish between different various particle species.

FIG. 9D shows how the lighting techniques of FIGS. 9A-9C can be applied sequentially to capture time-series data of scattering, reflecting, and/or occluding particles. In this case, a system containing a uniform backlight, rear-angled lights, a bottom light and a single camera alternates the lighting each frame, such that only one particular light source 122 (or combination of light sources 122) is active at a time. For a single imager (not shown), only one set of lights is used per acquired frame of time-series data. Repeating this sequence provides a video for each lighting configuration.

Acquiring a video sequence using the aforementioned lighting techniques sequentially provides a near simultaneous video for each light source 122. At completion, this provides three interleaved videos, one for each lighting technique. For each video, a particle in a given frame may correlate with the same particle in the other two videos using alternate lighting techniques (neglecting the small time difference between frames). Using the mutual information contained from the way a given particle interacts with the various lighting techniques, conclusions can be made about the material composition of the particle.

This technique can be combined with other image feature extraction information in order to increase specificity. For instance, the videos can be auto-segmented to determine the features in each frame. For each lighting technique, information such as size, shape, brightness, smoothness, etc., can be automatically determined for each feature. This can help to differentiate different particle types that have similar signatures in terms of visibility on each of the different lighting techniques.

Figure 10A:
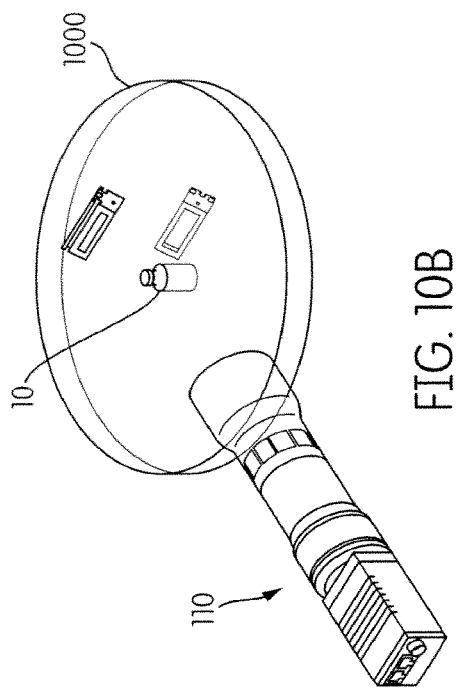
FIGS. 10A-10C illustrates glare from a vessel partially filled with fluid (FIG. 10A) and positioning of light sources outside a zone defined by revolving the imager about the vessel's longitudinal axis (FIGS. 10B and 10C).
Figure 10B:
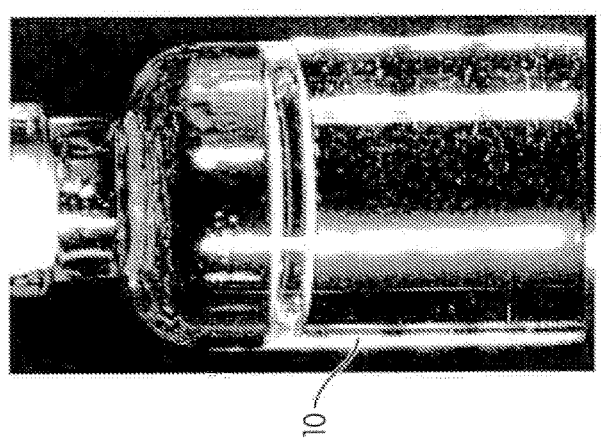
Figure 10C:
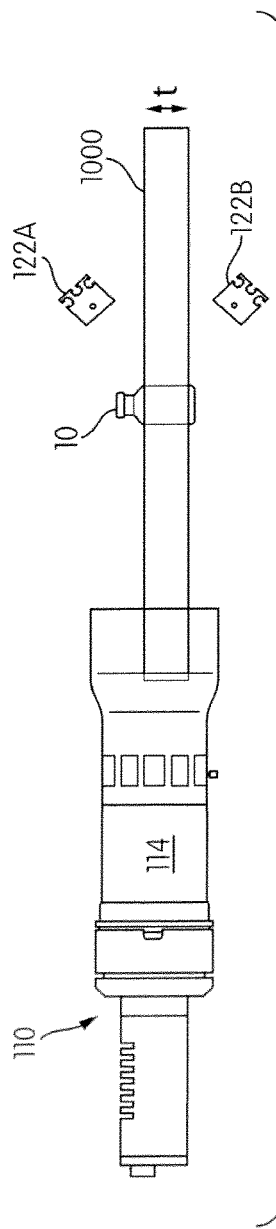

FIGS. 10A-10C illustrate how to reduce glare caused by unwanted reflection/refraction of light from the light sources 122 off the container 10. Illuminating the container 10 causes unwanted glare to appear in images captured by imagers 110 whose optical axes are aligned with the propagation direction of light from the light sources 122 that reflects off the container surface. Glare may obscure particles that would otherwise be detectable and saturate areas of the sensor. Positioning the imager 110 or the light sources 122 so that the imager's optical axis is not coincident with or parallel to rays of light emit by the light sources 122 that reflect of the container surface reduces or eliminates glare detected by the sensor. For example, placing the light source(s) 122 outside of an exclusion zone defined by revolving the imager about the longitudinal axis of the container 10 reduces the amount of unwanted reflected and/or refracted light captured by the imager. Alternatively, the zone 100 can be defined as a plane orthogonal to the central axis of the cylindrical container, with a thickness equal to the height of the containers' vertical walls. As understood in the art, containers with more complex shapes, such as concave sidewalls, may have different exclusion zones and different corrective optics.

Illuminating the container sidewalls obliquely from above or below the zone 1000, or from directly below the container base also reduces the glare detected by the imager 110. Illuminating the container 10 from below (e.g., with light source 122e (FIG. 8)) also provides excellent contrast between particles that reflect light (e.g., glass lamellae) and those which scatter light (e.g., protein).

Figure 10D:
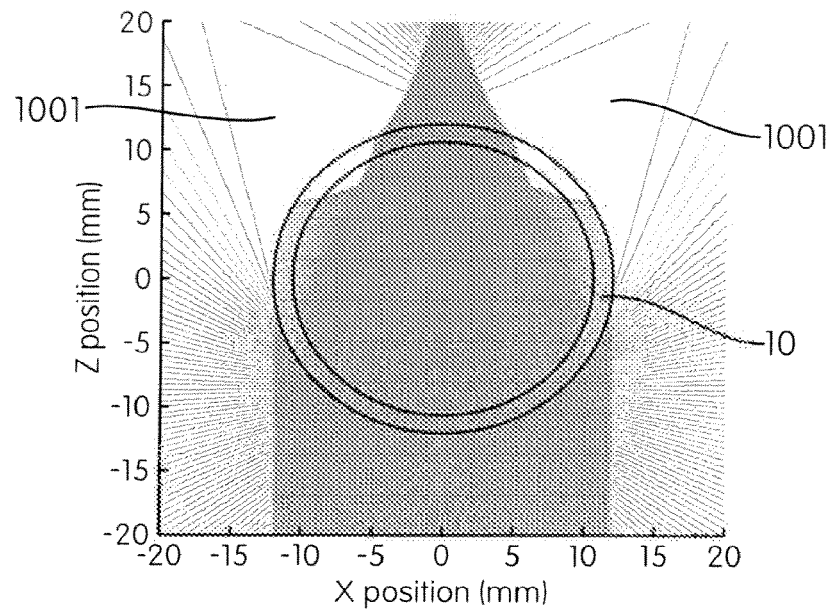
FIGS. 10D-10E illustrate an alternative illumination scheme for reducing or eliminating glare from a vessel.
Figure 10E:
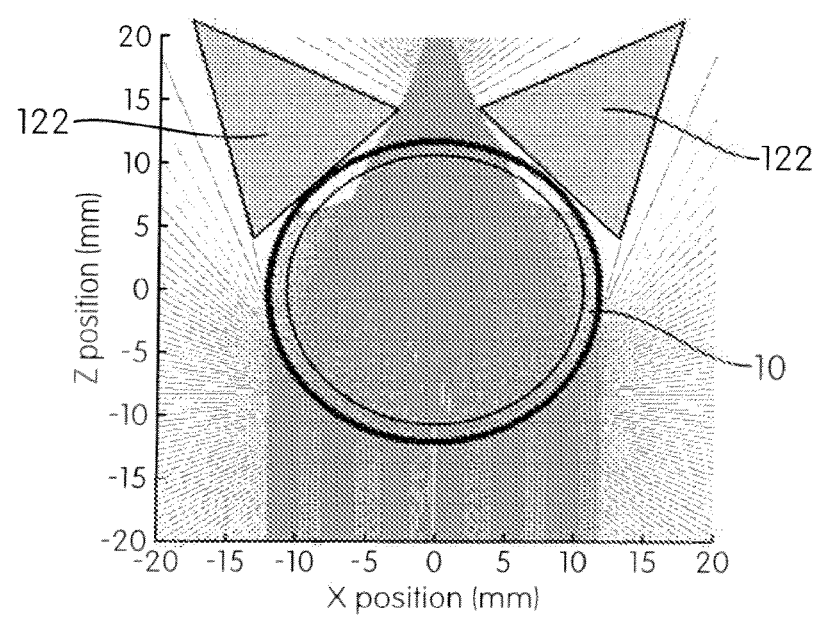

FIGS. 10D-10E illustrate an alternative illumination scheme for reducing or eliminating glare from the container 10, where one or more light sources sources 122 are placed in the exclusionary zone described above (e.g., in the horizontal plane of the container 10).

FIGS. 10D-10E show a ray optics model of the propagation of rays outward from the sensor of imager 110, through the imaging optics of the imager (as shown, including a telecentric lens), and back through the container 10. A light source placed along any of the rays that back propagate from the sensor will refract or reflect light onto the sensor, thereby potentially obscuring the container 10 and its contents. Note however, that there are two regions 1001 located in the horizontal plane of the container 10 and close to the outer wall of the container 10. As shown in FIG. 10E, if one or more light sources 122 are placed in the regions 1001, glare from the light sources may be reduced or substantially elimination.

Note that, because a telecentric lens was used in the example shown, only light rays incident normal to the sensor need to be considered in the ray optics model. However, a similar approach may be applied for other types of imaging optics, taking into account additional rays. For example, in some embodiments, one may back propagate a representative set of rays from the sensor (e.g., including the principle rays of the imaging system) to identify regions that are free or substantially free of back propagated rays. Illumination light sources can be placed in the identified regions while avoiding glare.

Figure 11:
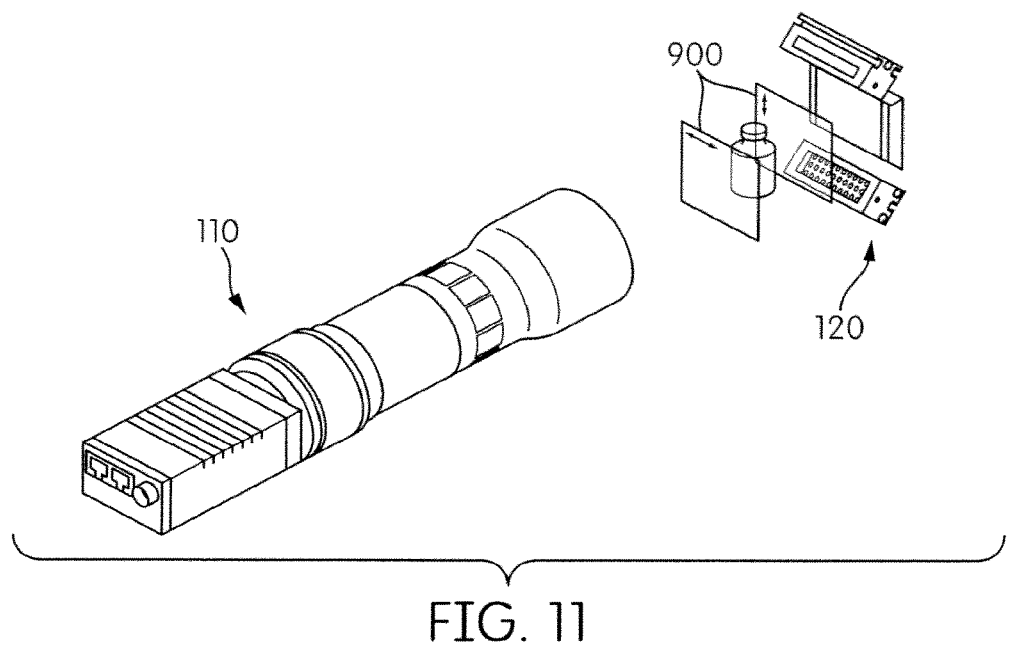
FIG. 11 is a schematic diagram of an imaging configuration suitable for imaging polarizing (e.g., chiral) particles.

FIG. 11 shows a setup for distinguishing elongated protein aggregates from cellulose and/or fibers (natural or synthetic) with polarized light. An illumination system 120 emits light towards the container 10, which is sandwiched between crossed polarizers 900 that provide a black image in the absence of particles. Particles that modify (e.g., rotate) the polarization of the incident light appear white in the time-series data detected by the imager 110.

Figure 12:
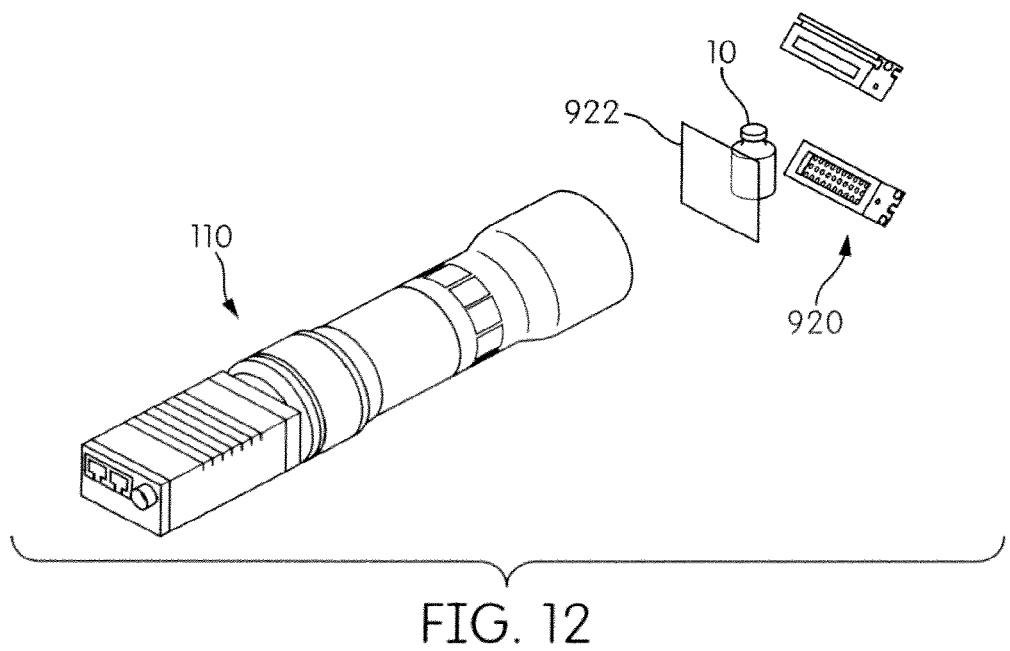
FIG. 12 is a schematic diagram of an imaging configuration suitable for exciting and imaging fluorescent particles.

If the particles of interest are known to fluoresce, fluorescence imaging can be employed for particle identification, as shown in FIG. 12. In this case, an illumination source 920 emits blue light that it excites the particle of interest. A narrow-band (e.g., green) filter 922 placed in front of the imager 110 ensures that only fluorescence from the excited particles will reach the detector. These illumination and filter wavelengths can be selected to suit the specific wavelengths of interest.

Finally, it is possible to detect (and identify) particles, such as small pieces of black, opaque material, that neither scatter (refract) nor reflect light. For such opaque particles, the sample should be backlit directly from behind. The particles are then identifiable as dark features on a bright background. Images of opaque particles can be inverted, if desired, to form images that are scaled with same polarity as images of scattering and reflective particles (that is, so particles appear as light spots on dark backgrounds instead of dark spots on light backgrounds).

Lamellae-Specific Visual Inspection Platforms

As understood by those of skill in the art, glass lamellae are thin, flexible pieces or flakes of glass formed by chemical reactions involving the inner surfaces of glass containers. The inventive systems and techniques can be used and/or tailored to detect, identify, and count glass lamellae to minimize the likelihood of administering drugs containing glass lamellae in order to prevent administration of drugs containing (excessive quantities) of glass lamellae. Inventive systems and techniques can also be used and/or tailored to study glass lamellae formation, which depends on the makeup of a given formulation and differ from proteins and other types of particulate matter in that they reflect and scatter light. Without being bound to any particular theory, it appears that certain conditions are more likely than others to promote or hinder glass lamellae formation. For example, glass vials manufactured by tubing processes and/or under higher heat tend to less resistant to lamellae formation than molded glass vials. Drug solutions formulated at high pH (alkaline) and with certain buffers, such as citrate and tartrate, are also associated with lamellae. The length of time the drug product remains exposed to the inner surface of the container and the drug product temperature also affect the chances that glass lamellae will form. For more, see, e.g., the U.S. Food and Drug Administration, Advisory to Drug Manufacturers: Formation of Glass Lamellae in Certain Injectable Drugs (Mar. 25, 2011) (www.fda.gov/Drugs/DrugSafety/ucm248490.htm), which is incorporated herein by reference in its entirety.

In order to create a system for differentiation based on this principle, the imager can be aligned with a vial in a typical fashion and oriented the incident lighting through the bottom of the container (orthogonal to the camera axis). This yields very little signal from particles that scatter (e.g., proteins), and a large signal from particles that reflect (e.g., glass lamellae). In other words, as the lamellae float through the vessel, they appear to flash intermittently. This technique has shown to be highly specific in differentiating lamellae particles from protein aggregates. Additionally, the signal obtained using this imaging technique is correlated with the concentration of lamellae within a vial. As a result, this technique can not only be used for non-destructive detection of lamellae in commercial products, but also used as a tool for determining which formulation compositions lead to increased/decreased lamellae presence.

Figure 13A:
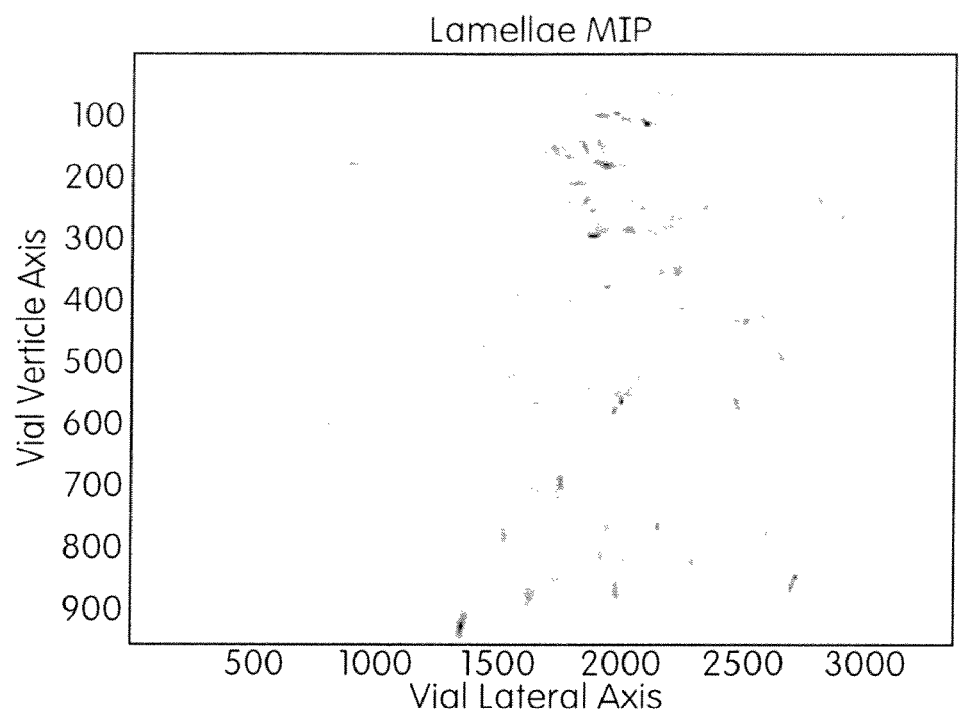
FIGS. 13A and 13B show maximum intensity projection images of glass lamellae (FIG. 13A) and protein (FIG. 13B) acquired with an illustrative visual inspection system.
Figure 13B:
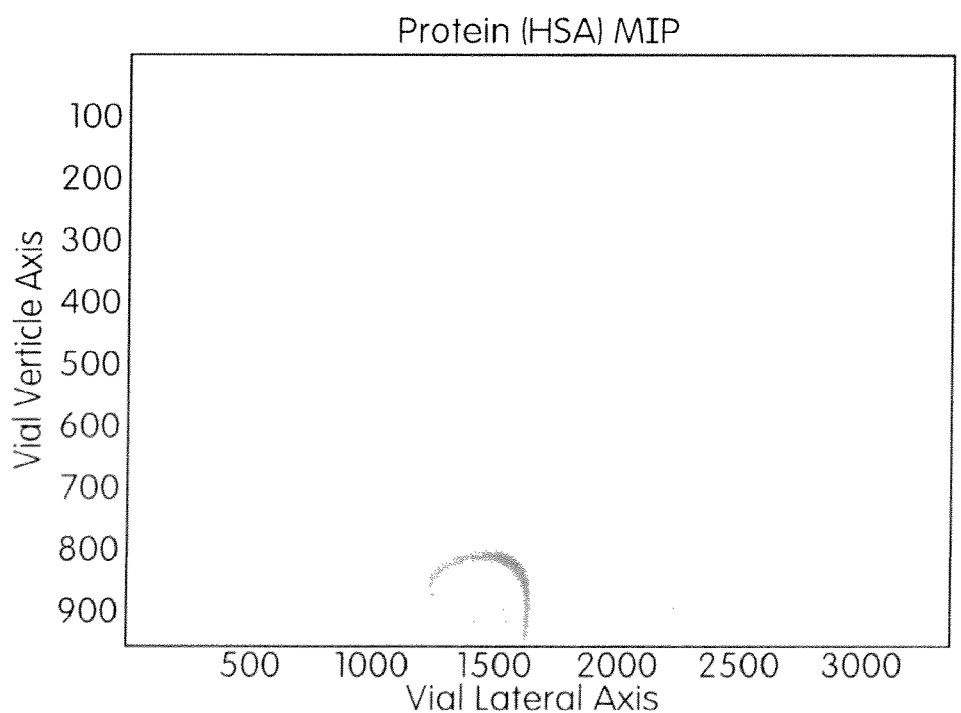

FIGS. 13A and 13B show maximum intensity projection (MIP) images of glass lamellae (FIG. 13A) and protein (FIG. 13B) acquired with an illustrative visual inspection system. Conventional MIP images are used in computerized tomography to visualize a three-dimensional space viewed along one spatial axis, e.g., the z axis. A typical conventional MIP image represents the maximum value of the data taken along an optical ray parallel to the visualization axis. In this case, however, the MIP images shown in FIGS. 13A and 13B are visualizations of data that represent the temporal evolution of a two-dimensional image—they are projections along a temporal axis rather than a spatial axis.

To create the MIP images shown in FIGS. 13A and 13B, the processor selects the maximum value of at least some of the pixels in the time-series data, where each pixel represents the amount of light reflected (and/or transmitted) from a respective spatial location in the vessel. Plotting the resulting values yields a MIP image, such as those shown in FIGS. 13A and 13B, that represents the brightest historical value of the pixels. The processor scores the MIP image by counting the number of pixels in the MIP image whose value exceeds a predetermined threshold. If the score exceeds a historical value representing the number of lamellae in a similar vessel, the processor determines that the vessel is statistically likely to contain glass lamellae. The processor may also determine the severity of lamellae contamination by estimating the number, average size, and/or size distribution of the glass lamellae from the MIP image.

Inventive systems can also be used to distinguish glass lamellae from other particles in the vessel, e.g., based on differences in the amount of light reflected by the particles as a function of time and/or on differences in the amount of light transmitted by the particles. Some non-lamellae particles may reflect light from a light source that illuminates the vessel from below (e.g., light source 122e in FIG. 8) to the detector. Glass chunks, metal chunks, and foreign fibers, for instance, could show up continuously using a bottom lighting configuration. These types of particles will consistently be detected as they move through the container, as opposed to lamellae which are orientation dependent and only visible for a few frames each time they align themselves to reflect light towards the imager. Particle tracking can be employed on bottom light time series images to track consistently visible, yet moving, particulate matter. These tracks can then be eliminated from MIP calculations used for lamellae scoring, or alternatively be included in a mutual light information technique to determine how a given particle interacts with other lighting orientations. For example, a metal particle that reflects light may be tracked on the bottom lighting configuration. That same particle occludes light when illuminated with a back light (e.g., light source 122f in FIG. 8). Using both of these metrics makes it possible to differentiate the metal particle from a glass chunk, which reflects bottom lighting but does not occlude rear lighting.

Particle Detection, Tracking, and Characterization

As described above, the visual inspection unit 100 shown in FIG. 1 can record a high quality, high-resolution monochromatic stream of images (time-series data) of bright particles imaged against a dark background. (Alternatively, the particles can be displayed as dark spots on a white background.) Because drug product can contain a wide assortment of radically differing particles, the time-series data can be analyzed using a number of different approaches to differentiate features on an image from the background. Often, the appearance of a particle on a single image (frame of time-series data) is not sufficient to make truly accurate quantitative estimates for critical objectives (e.g., count/size). For instance, what appears to be a single particle in one frame of time-series data may actually be two or more particles colliding with each other or passing by each other, which may result in accurate particle counts and/or estimations of particle size.

Temporal correlation of image features between frames in a video sequence improves the precision of particle counting and size measurements. The process of linking image features in consecutive frames together to form a time dependent trajectory for each particle is known as particle tracking, registration, or assignment. Particle tracking techniques exist for other applications (notably in the experimental study of fluid mechanics). However, these applications typically employ well-defined spherical tracer particles. Applying the principle to drug products and other fluids requires a significantly more complex solution. In addition, for some species of particles, temporal (tracking) analysis is not always practical. In such cases a statistical approach can be employed as an alternative to yield characteristic measurements.

Figure 14:
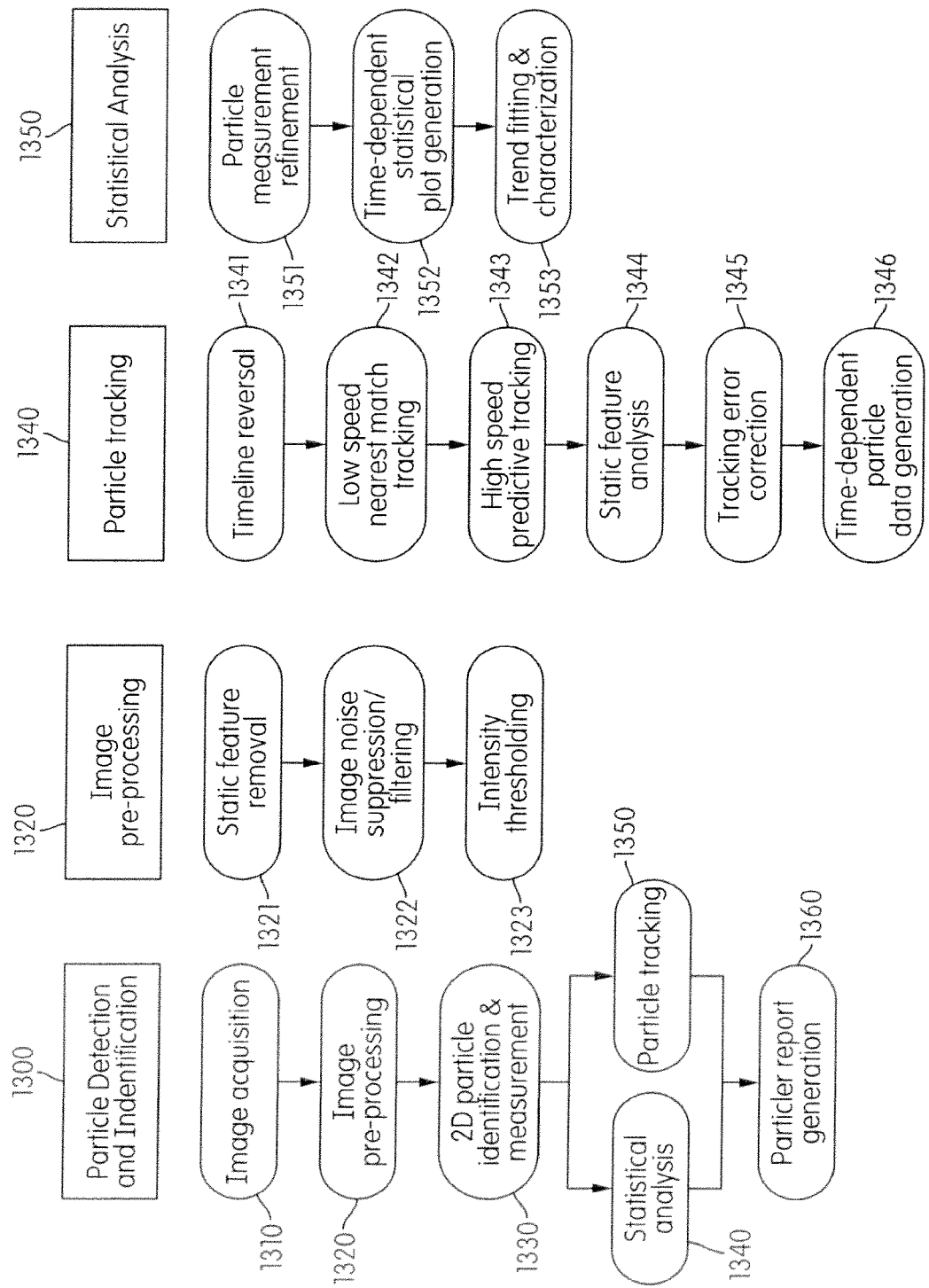
FIG. 14 includes flowcharts that illustrate different the overall particle detection and identification process as well as image pre-processing, particle tracking, and statistical analysis subprocesses.

FIG. 14 provides an overview of the high-level particle detection and identification 1300, which starts with acquisition 1310 of time-series data. The time-series data (and/or reversed time-series data) is pre-processed 1320, and the pre-processed, reversed time-series data is used for two-dimensional particle identification and measurement 1330, which may include statistical analysis 1340 and/or particle tracking 1350 of the reversed time-series data. As explained above, reversed time-series data is time-series data whose frames have been re-ordered in reverse chronological order. Particle report generation 1360 occurs upon completion of particle identification and measurement 1330.

Time-Series Data Pre-Processing

Pre-processing 1320 includes static feature removal (background subtraction) 1321, image noise suppression/filtering 1322, and intensity thresholding 1323. Static feature removal 1321 exploits the fact that spinning the container energizes the fluid and the particles contained within. Their dynamic motion allows them to be distinguished from other imaging features. Since image capture commences after the container has stopped spinning, the assumption is that everything that is moving is a potential particle. Static features are subsequently irrelevant and can be removed from the image to improve clarity.

Figure 15B:
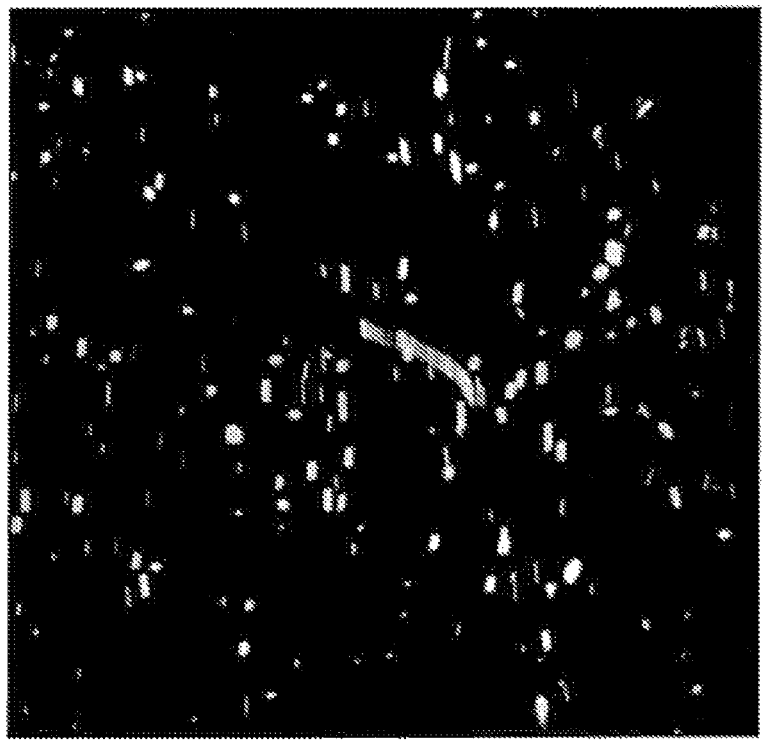
FIGS. 15A and 15B show a frame of time-series data before (FIG. 15A) and after (FIG. 15B) background subtraction.
Figure 15A:
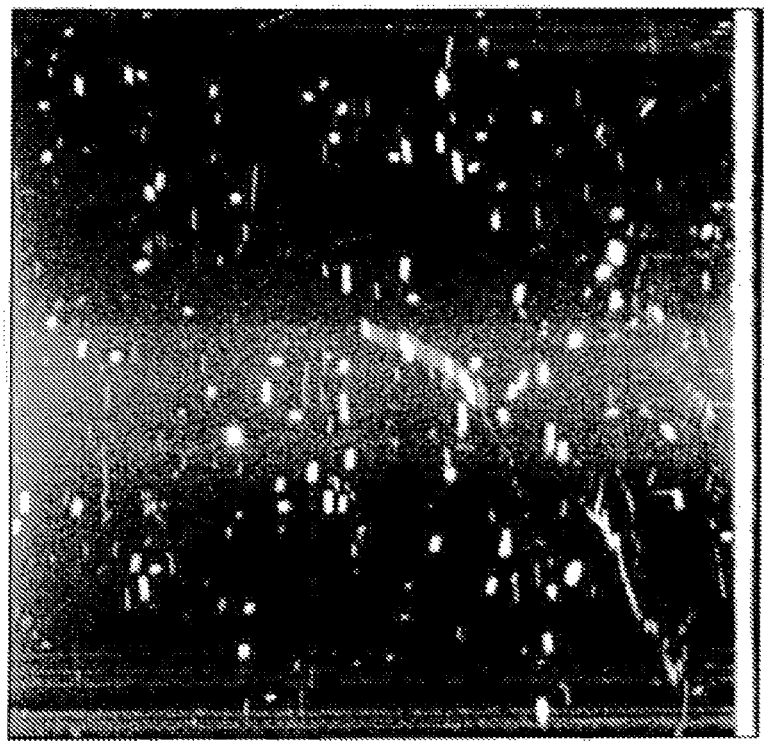

In one embodiment, a minimum intensity projection establishes an approximate template for features in the image that are static. This includes, for instance, scratches, dirt and defects that may be present on the container wall. This 'static feature image' can then subsequently be subtracted from the entire video sequence to generate a new video sequence that contains only moving features against a black background. For example, FIGS. 15A and 15B show a single frame of time-series data before and after static feature removal. Glare, scratches, and other static features obscure portions of the container in FIG. 15A. Background subtraction removes many of the static features, leaving an image (FIG. 15B) with more clearly visible moving particles.

A caveat of this approach is that most glass defects such as surface scratches scatter a relatively significant amount of light, appearing bright white in the captured images, as detector pixels are saturated. Subtraction of these features may result in 'dead' regions in the image. As particles move behind or in front of these illuminated defects, they may be partially occluded or even disappear entirely. To resolve this problem, the 'static feature image' can be retained, analyzed, and used to correlate defect positions to particle positions to minimize the influence of surface defects on particle size and count data. (As a side note, application of a cleaning protocol is advised before operating the system to ensure surface defects have been removed as much as possible.) The data can also be filtered 1322, e.g., to remove high-frequency and/or low-frequency noise. For example, applying a spatial bandpass filter to the (reversed) time-series data removes and/or suppresses data that varies above a first spatial frequency or second spatial frequency.

Figure 16A:
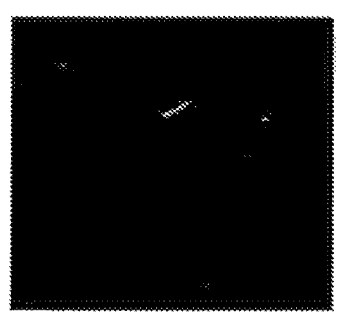
FIG. 16A is a time-series data frame of a particle shown on eight-bit grayscale (shown at left).
Figure 16A:
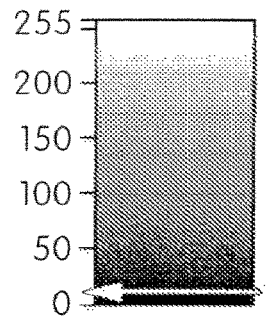
Figure 16B:
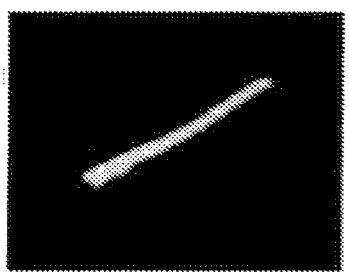
FIG. 16B is a close-up of the time-series data frame shown in FIG. 16B.
Figure 16B:
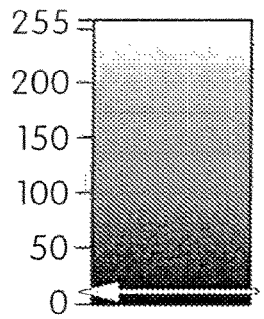
Figure 16C:
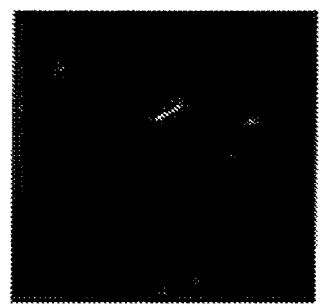
FIGS. 16C and 16D are thresholded versions of the time-series data frames shown in FIGS. 16A and 16B, respectively.
Figure 16C:
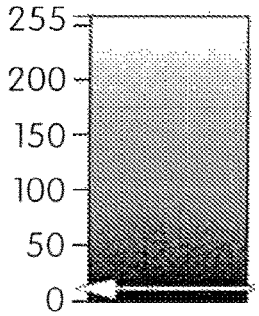
Figure 16D:
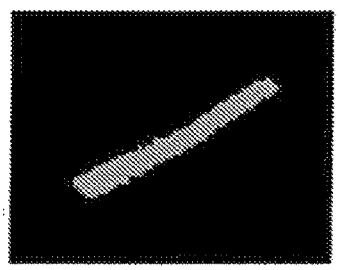
Figure 16D:
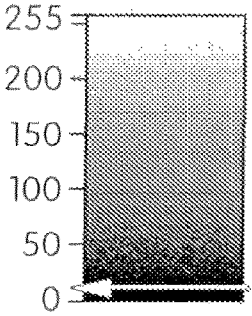
Figure 17A:
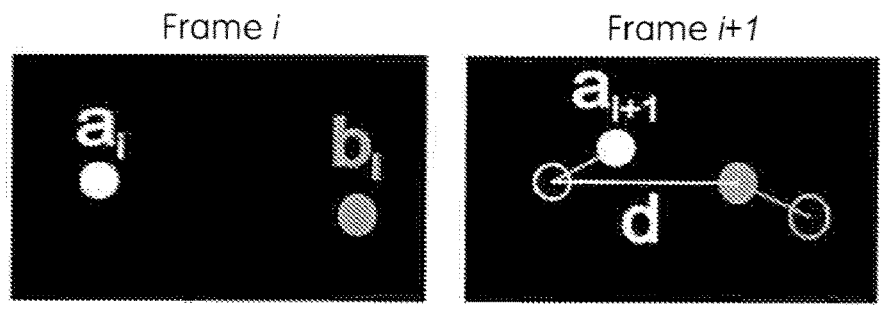
FIGS. 17A-17D illustrate how a pair of successive frames of time-series data (FIG. 17A) can used to perform predictive tracking (FIGS. 17B-17D).
Figure 17B:
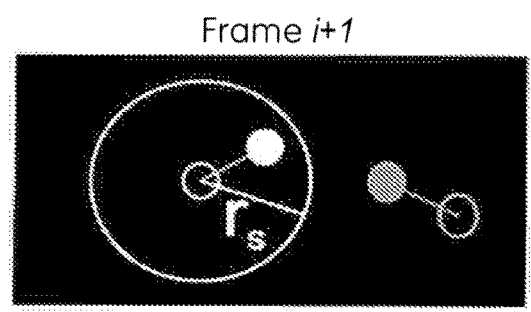
Figure 17C:
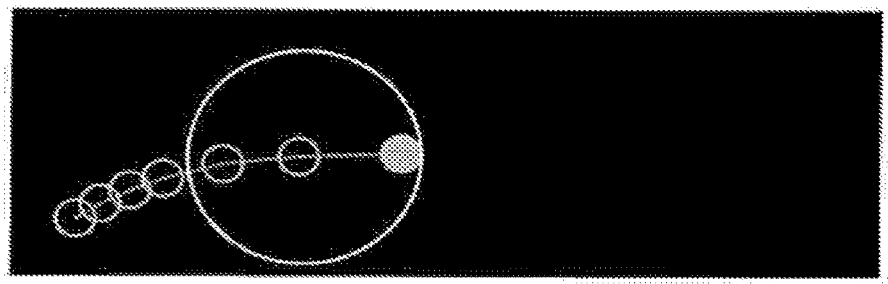
Figure 17D:
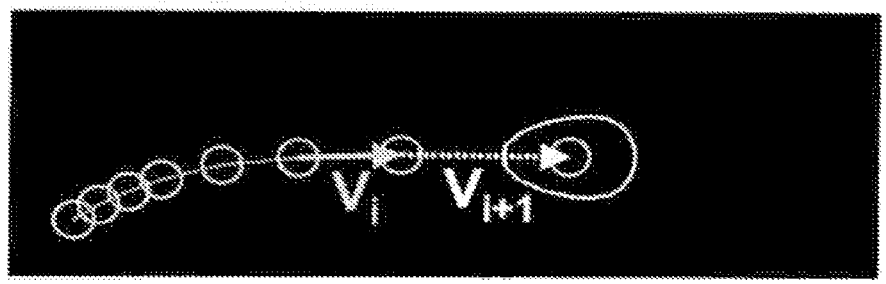

Once the background features have been removed, the time-series data is thresholded 1323 by rounding the intensity value of each pixel in the image to one of a predetermined number of values. Consider the grayscale images shown in FIGS. 16A and 16C, which are scaled according to the eight-bit scale shown at left (other possible scales include 16-bit and 32-bit). Each pixel has an intensity value from zero to 255, where zero represents no detected light and 255 represents the highest amount of light detected. Rounding those intensity values of 127 or under to zero and those intensity values of 128 and up to 255 yields the black-and-white images shown in FIGS. 16B and 16D. Those of skill in the art will readily appreciate that other thresholds (and multiple thresholds) are also possible.

Particle Detection

Effective particle detection in an image relies on a variety of image processing and segmentation techniques. Segmentation refers to the computational process by which features of interest in an image are simplified into discrete, manageable objects. Segmentation methods for extracting features from an image are widely used, for example, in the medical imaging field, and these techniques have been employed for particle identification. In short, the images acquired from the camera are pre-processed using thresholding, background (static feature) subtraction, filtering (e.g., bandpass filtering), and/or other techniques to maximize the contrast. At the completion, the processor 130 segments the image, then selects certain areas of an image as representing particles and categorizes those areas accordingly. Suitable segmentation approaches include, but are not limited to confidence-connected, watershed, level-set, graph partitioning, compression-based, clustering, region-growing, multi-scale, edge detection, and histogram-based approaches. After the images are acquired, segmentation can yield additional information to correlate a given feature on an acquired image with a particle type. For instance, information about the given segmented feature such as area, perimeter, intensity, sharpness, and other characteristics can then be used to determine the type of particle.

Particle Tracking and Time Reversal

Critically, no previously available particle identification tools consider in full detail the temporal behavior of the particles as they move around the vial. The counting and sizing of particles can be inaccurate if only measuring from a single "snapshot." However, time-series data provide a more complete picture of particle behavior that can be resolved using using particle tracking 1340, which enables the creation of time-dependent spreadsheets for each individual particle, enabling a far more robust and accurate measurement of its fundamental properties. Particle tracking is a technique used extensively in video microscopy, as well as in fluid dynamics engineering (where it is commonly referred to as particle tracking velocimetry, or PTV).

Although PTV is known, the majority of particle tracking solutions assume that movement of particles between successive video frames is slight, and smaller than the typical separation distance between particles in a given image. In such cases, it is sufficient to link particle positions by identifying closest matching neighbors. In many applications, however, this is not an appropriate model. Due to the spin speed (e.g., about 300 rpm, 1600 rpm, and/or 1800 rpm) and potentially high particle concentrations, particles can be expected to move far further between successive frames than the typical inter-particle separation distance. This can be resolved by employing a form of predictive tracking, which involves searching for a particle in a region predicted by the particle's prior movement. Predictive tracking includes the evaluation of physical equations to mathematically predict the approximate future position of the particle in the subsequent frame, as shown in FIG. 17. For improved performance, this phase of predictive tracking can be coupled with knowledge of the local fluid behavior (if known), e.g., as described with respect to FIG. 21C.

Forming an accurate prediction for a given trajectory may require some prior data points on which to base the trajectory. This presents a conundrum—at the start of the image sequence, when the particles are moving fastest, there may be little to no prior data on which to base position predictions. Over time, however, wall drag in the container causes the rotating fluid to slow down and ultimately stop. Recording time-series data for long enough yields frames in which the particles slow down considerably and even stop.

Reversing the timeline of the video 1331, so that the particles initially appear to be static, and slowly speeding up as the video progresses provides "prior" data points for determining the trajectory. At the start of the video, where the particles are now barely moving, the nearest-match principle can be used to build up the initial phase of each trajectory. At an appropriate time, the system can then switch to the predictive mode. Reversing the timeline of the acquired data in this manner dramatically improves performance.

FIG. 17 shows an overview of predictive tracking with time reversal. The goal of particle tracking is to track link the position of a particle $a_i$ in frame i to its position $a_{i+1}$ in frame i+1, as shown in FIG. 17(a). This is straightforward if the movement of particle a between frames is smaller than the distance d to its nearest neighbor, particle b. If the particle's direction of movement is unknown or random, the simplest methodology is to have a search zone—typically a circle of radius $r_s$, where $r_s$ is chosen so as to be longer than the expected range of particle movement, but smaller than the typical inter-particle separation distance d, as shown in FIG. 17(b). After reversing the movie timeline, as in FIG. 17(c), the particles appear to begin to move slowly. After a while, however, the particles appear to speed up, and the nearest-match search method may start to fail. The first few frames of reversed time-series data partially establish the trajectory, yielding some knowledge of the particle's velocity and acceleration. This information can be input into appropriate equations to predict the particle's approximate location in frame i+1, as in FIG. 17(d). This predictive tracking method is considerably more effective than simple nearest match tracking, especially in dense and/or fast moving samples.

Center-of-Mass Detection

Figure 18A:
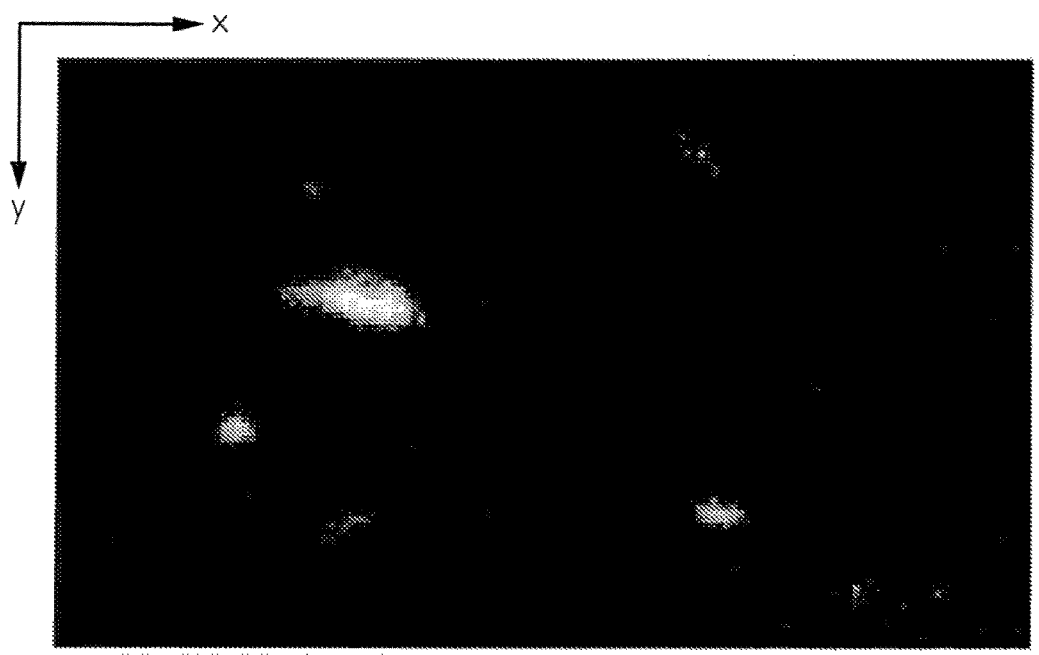
FIG. 18A shows a grayscale time-series data frame showing several particles.
Figure 18B:
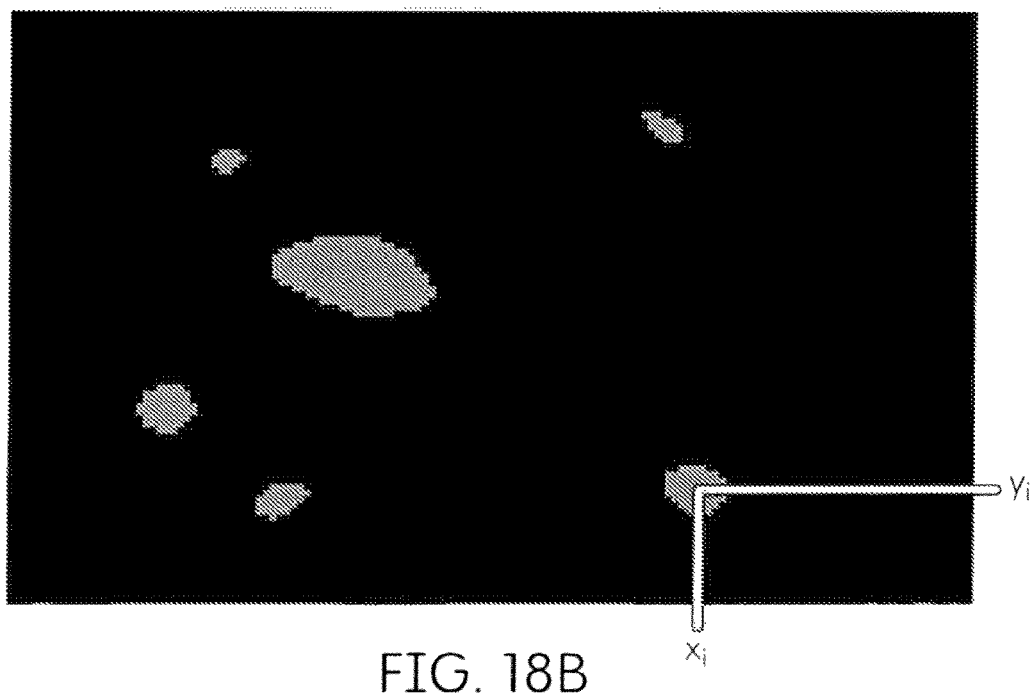
FIG. 18B shows a thresholded version of FIG. 18A used to locate a particle's geometric center.

FIGS. 18A and 18B illustrate center-of-mass detection for particles in (reversed) time-series data after thresholding. First, the processor 130 transforms a grayscale image (FIG. 18A) into a thresholded image (FIG. 18B). Each particle appears as a two-dimensional projection whose shape and size depend on the shape, size, and orientation of the particle when the frame was recorded. Next, the processor computes the geometric center, or centroid, of each two-dimensional projection (e.g., as indicated by the coordinates $x_i$ and $y_i$) using any suitable method (e.g., the plumb line method, by geometric decomposition, etc.). The processor 130 can compare the location of the centroid of a particular particle on a frame-by-frame basis to determine the particle's trajectory.

Particle Occlusion

Figure 19:
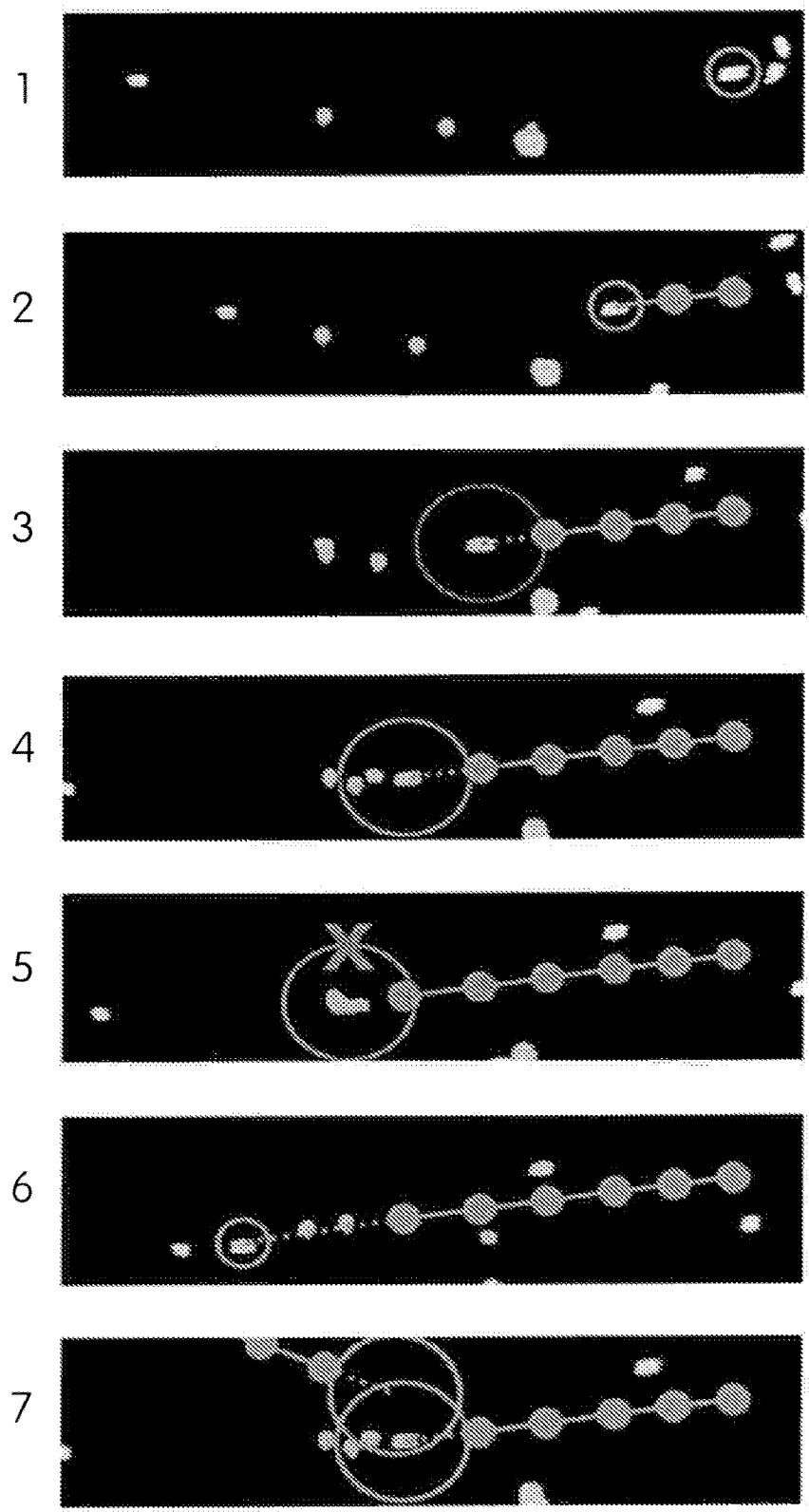
FIG. 19 shows successive time-series data frames that illustrate particle collision/occlusion.

Each of the visual inspection systems disclosed herein project a three-dimensional volume—a container and its contents—onto the two-dimensional surface of the image sensor. For a given two-dimensional sensor, it is possible for particles in the three-dimensional volume to appear to cross paths. When this happens, one particle may partially or completely occlude another, as shown in FIG. 19. In FIG. 19(1), a new particle is identified in the image sequence; tracking the particle through the image sequence yields a series of sequential steps as shown in FIG. 19(2). Employing a search zone to look for potential matches in consecutive frames as shown in FIG. 19(3). Occasionally more than one candidate particle will occupy the search zone, as shown in FIG. 19(4), in which case the system selects the best match. As readily appreciated by those of skill in the art, the best match can be decided using any one of combination of different approaches. For instance, data representing a candidate particle in one frame can be compared to and/or correlated with data representing a particle in a preceding frame. Comparing and/or correlating parameters including, but not limited to size, shape, brightness, and/or change in appearance leads to a match for the candidate particle. Illustrative visual inspection systems can cope with collisions, occlusions, and temporary particle disappearances, such the occlusion shown in FIG. 19(5). When the particle is recovered, as in FIG. 19(6), the track can be reconstructed. Illustrative systems can also resolve conflicts caused when two tracks (and their search zones) collide, ensuring that the correct trajectories are formed, as in FIG. 19(7).

FIG. 20 illustrates another case of particle occlusion in a two-dimensional image: (a) is a typical image of particles in suspension. FIGS. 20(b)-(e) show close-ups of the boxed region in FIG. 20(a), with two particles approaching one another from opposite directions. The next frames in the (reversed) time-series data show that occlusion causes two particles to appear to be a single, artificially large particle. If the occlusion is partial (FIG. 20(c)), this can lead to the appearance of single, artificially large particle. If the occlusion is complete (FIG. 20(d)), then the smaller particle may be lost from the field of view completely and the particle count may decrease by one. This may be of critical importance when inspecting drug products because the artificially increased size measurement may be sufficient to exceed regulatory thresholds, when in fact the product under scrutiny contains only acceptable, sub-visible particles. By FIG. 20(e), the particles have moved beyond one another and independent tracking can continue. By analyzing the particle trajectories and the subsequent time-dependent size profiles, the visual inspection system can automatically correct for errors due to occlusion, leading to a lower rate of false rejects.

Accounting for Lost Particles

As discussed, particles can disappear from a portion of a given video sequence for a number of reasons. They may traverse a 'blind spot' and/or a 'dead' region due to the static feature removal as discussed above. Finally, some types of particles may exhibit optical behavior where they appear and disappear (sparkle) with respect to the imaging optics. In such cases, the processor can predict the movement of these 'lost particles' as follows. Should the particle re-appear at an expected location within a certain timeframe, the processor can link the trajectories and interpolate virtual particle data for the interim frames. Note that from a regulatory standpoint it is important to be clear that virtual particle data is appropriately tagged so that it can be distinguished from true measured particle data.

Figure 21A:
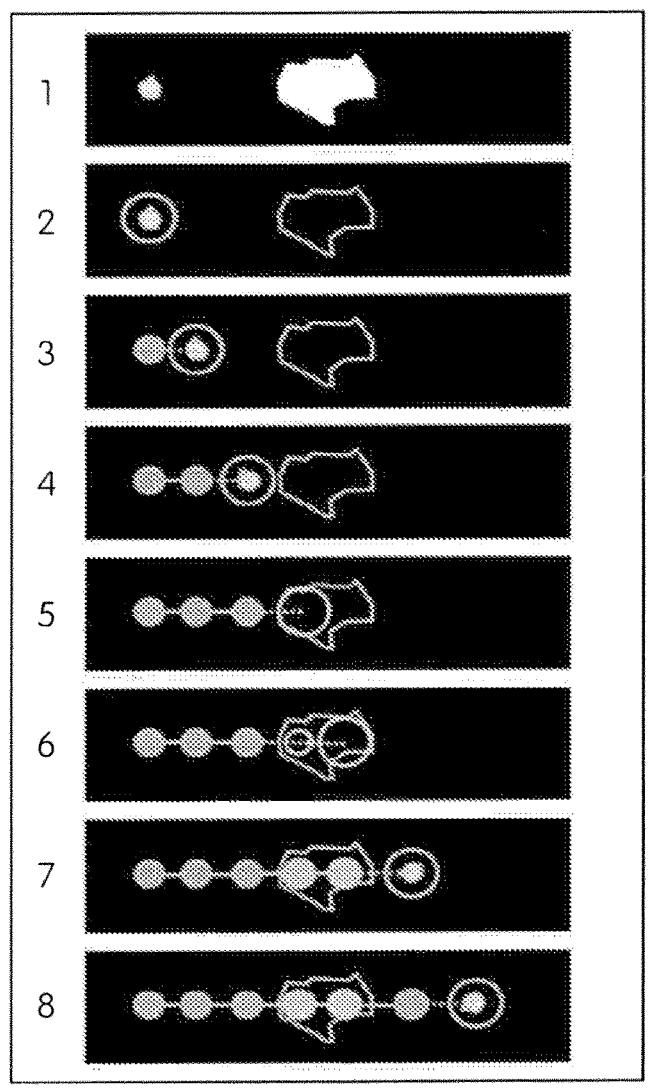
FIGS. 21A-21C illustrate apparent occlusion of a moving particle caused by background subtraction of an artifact, such as a scratch or piece of dirt, on a wall of the vessel for straight trajectories (FIG. 21A), curved trajectories (FIG. 21B), and parabolic trajectories (FIG. 21C).
Figure 21B:
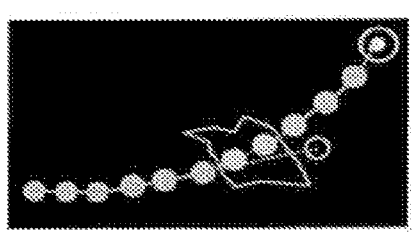
Figure 21C:
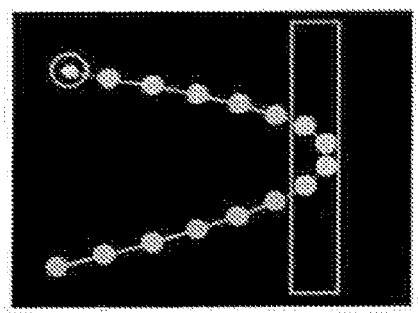
Figure 23A:
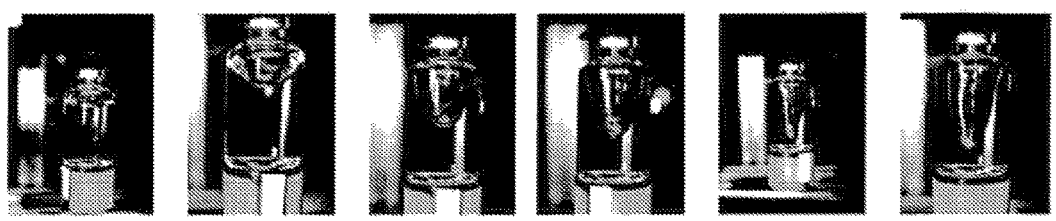
FIGS. 23A-23D illustrate fluid dynamics observed and modeled in cylindrical vessels.
Figure 23B:
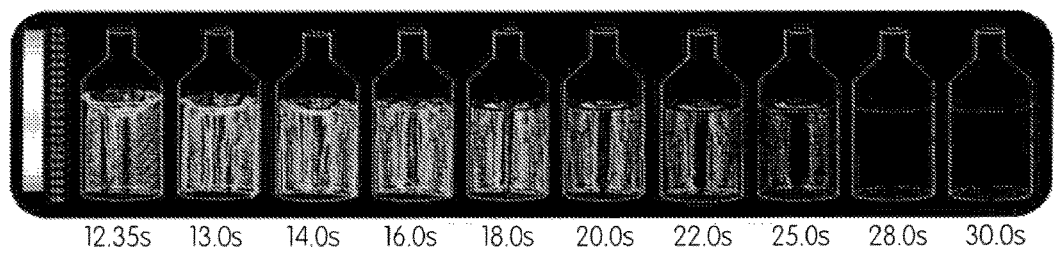
Figure 23C:
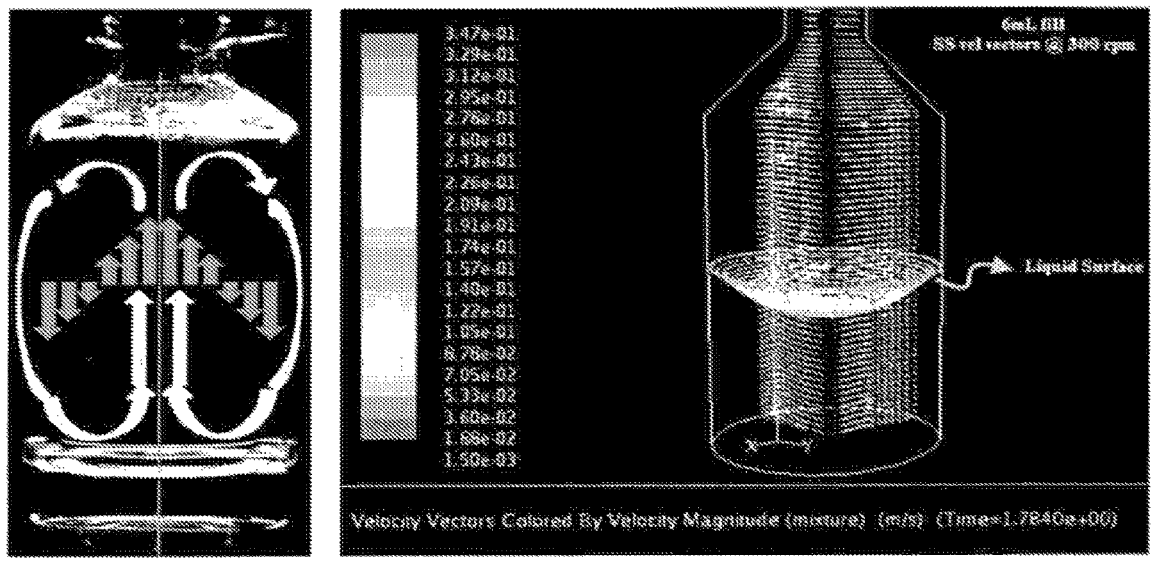
Figure 23D:
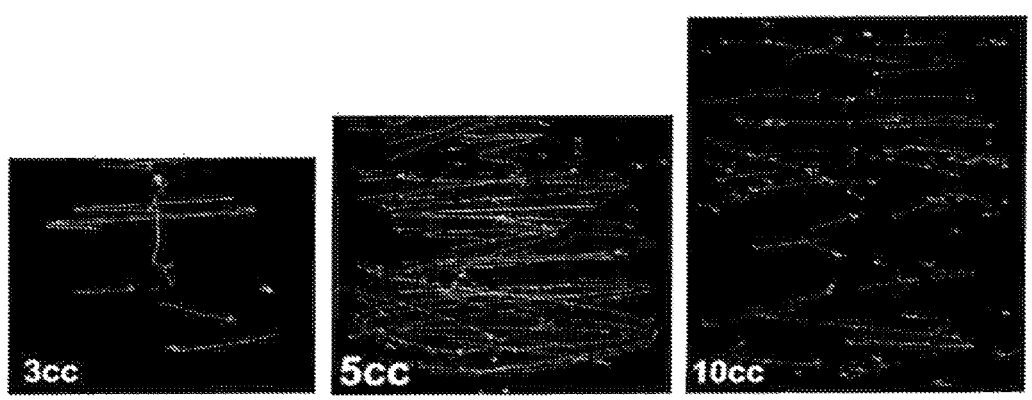

FIGS. 21A-21C illustrate one technique for tracking and recovering lost particles, i.e., particles that temporarily disappear from the field of view over the course of a video sequence. Disappearance may be due to occlusion behind another (larger) particle, occlusion behind a surface defect, transition through a known blind spot or simply a property of the particle's optical geometry (for example, some types of particles may only be visible at specific orientations). Finding or recovering particles that disappear from the field of view improves the precision with which particles can be detected and identified.

FIG. 21A illustrates predictive tracking to find a particle that is occluded by a defect on the container surface. The surface defect scatters a large amount of light, saturating the corresponding region of the image. After static feature removal is employed, this results in a 'dead zone' in the image. Any particles that traverse this zone disappear temporarily. The processor 130 can recover 'lost' particles by creating virtual particles for a finite number of steps. If the particle re-appears and is detected, the tracks are united.

More specifically, the processor 130 uses predictive tracking to determine the particle's velocity prior to its disappearance. It can also use predictive tracking and the particle's velocity to extrapolate an expected particle position. If the particle appears again in an expected position, the virtual positions can be linked to form a complete trajectory. If the particle does not reappear within a pre-defined time window, it can be signaled as being permanently lost, and is no longer tracked.

FIG. 21B shows how to track a particle that undergoes a significant acceleration or change of direction while it is out of sight. Rather predicting the particle trajectory, the processor 130 retrospectively links fragmented trajectories using the nature of the local behavior of the fluid. In this case the processor 130 united the trajectories by considering the laminar flow characteristics of the fluid at this speed and scale.

FIG. 21C illustrates how particles disappear and re-appear as they traverse known blind spots. In this example, the particle traverses a known blind spot at the extreme edge of the container. Programming the processor 130 with information about the position of the blind spot with respect to the container image enables the processor 130 to reconstruct the trajectory.

Particle Shape Irregularity

Some particles are not spherical or small enough to be considered point-like, as assumed by most particle tracking techniques. In fact, many particles are irregularly shaped and may tumble and rotate relative to the camera as they move through the fluid, as shown in FIGS. 22A-22C. In some cases, an irregularly shaped particle may appear as two separate particles, each with its own trajectory, as shown in FIG. 22B. Such unpredictable movement of the measured center of mass of the two-dimensional object may obscure the true movement of the particle. This behavior seriously complicates the process of predictive tracking. The visual inspection system described herein may contain functionality to cope with the apparently perturbed motion of an irregularly shaped particle, e.g., by calculating a mean trajectory as shown in FIGS. 22A and 22C for the irregularly shaped particle.

Container/Product-Specific Fluid Dynamics

The motion of particles in the container post-spin is a result of the combination of the motion of the fluid with the effect of gravity. The motion of the fluid is a function of the fluid's viscosity, the fill volume, the container shape and size, and the initial spin speed. Particle tracking performance can be significantly improved by incorporating knowledge of the physical constraints of the fluidic system into trajectory-building.

The fluid dynamics of liquids spun in conventional containers can be surprisingly complex under certain circumstances. Incorporating fluid dynamics knowledge (as it pertains to containers typically used in the drug industry) into trajectory-building constitutes a significant area of novelty and development over the prior art.

FIG. 23 shows some examples of fluid behavior in typical containers, with results from a computational model compared against real-world particle trajectories generated by the visual inspection platform. Studies have uncovered unexpected subtleties: as an example, in FIG. 23(d) we can see particle movement along a narrow vertical column in the center of the vial, which is due to the relaxation of the vortex created during the spin phase (FIG. 23(a)). As the fluid in this central column moves vertically upwards, it can sweep upwards heavy particles that one may normally expect to sink. This could, for example, cause confusion between identifying bubbles, which one would expect to rise, and foreign particles which are rising due to container-specific fluid motion.

Illustrative visual inspection systems can leverage prior knowledge of the expected fluid dynamics of drug products to yield considerable more accurate results than would otherwise be possible. Combining a physical model, such as the one illustrated in FIG. 23, with particle tracking in this fashion represents a significant improvement over existing technology.

Error Correction

While the visual inspection systems disclosed herein are robust under most experimental conditions, the complexity of the challenge of tracking large numbers of particles moving in a small three-dimensional volume means there is always the risk of some errors being introduced, chiefly in the form of incorrect trajectories being formed between successive frames when particles 'collide'. This phenomenon is illustrated in FIG. 24A.

An understanding of the physical constraints of the visual inspection system can be employed to advantage. Broadly speaking, the predominant movement of the fluid locally around each particle is laminar (rather than turbulent or random). What this essentially means is that, with a sufficiently fast camera, natural particle trajectories in this system should be smoothly varying, with no sudden, sharp changes in direction, particularly as particles traverse the center of the container in the image. Once initial trajectory linking is complete, the system can retrospectively analyze the trajectories for such errors. If they are detected, the system can compare nearby trajectories to establish whether a more physically consistent solution can be found. This is shown in FIG. 24B.

Accurate Particle Counting

Figure 24A:
FIGS. 24A and 24B show close-ups of consecutive frames of reversed time-series data where particle collisions have not been correctly resolved (FIG. 24A) and the same plot after error correction (FIG. 24B).
Figure 24B:

A particle count can be deduced by counting the number of particles in a snapshot image taken at a single point in time (e.g., as shown in FIG. 24A) after particle detection, where each particle is labeled with a count number. This approach is straightforward, but has a tendency to systematically undercount the number of particles in the volume for a variety of reasons. For instance, one or more particles may be occluded by another particle or surface defect. Particles may be in known (or unknown) blind spots. In addition, extremely small or faint particles may intermittently appear and disappear from view as they move across measurement thresholds.

One advantage of the particle tracking discussed herein is that it can account for all of these problems. As a result, for robust particle tracking, particle counting can be improved by counting the number of individual particle tracks (as in FIG. 24B), rather than the number of particles in a single image or a statistical analysis of several images. Counting the number of particle trajectories rather than the number of particles in a single frame (or ensemble of frames) represents a significant improvement over conventional particle tracking techniques. The size of the improvement varies with the number and size(s) of the particles present. Roughly speaking, as the number of particles increases, the chance of occlusion increases and so the improvement due to the temporal capabilities of the inventive particle tracking increase proportionally.

Accurate Particle Sizing

Conventional particle measurement systems measure particle size from static images. Most typically this is done by measuring the length of the particle's longest apparent axis, or Feret diameter, as shown in FIG. 25, according to regulatory and/or industry standards, which may define the particle size as the longest single dimension of the particle. Under this definition, a 1 mm hair is classed the same as a spherical particle with a 1 mm diameter. With this in mind, from a two-dimensional image, the maximum Feret diameter is a reasonable measurement to use. Measurement of particle size from static images however, suffers several critical problems.

First, in a two-dimensional projection of a three-dimensional volume, it is easily possible for multiple particles to overlap, creating what appears to be a single, much larger particle. In an industry where regulators set very strict upper limits on allowable particle size, this is a critical problem, particularly for manufacturing applications, where it may lead to false rejects, particularly for densely populated samples.

Second, irregularly-shaped particles may tumble unpredictably (relative to the camera) as they flow around the container. With a single two-dimensional snapshot, it may be impossible to guarantee that a given particle's longest dimension is orthogonal to the camera's viewing axis. The system may therefore systematically undersize particles, which could have dire consequences in a heavily regulated industry. Examining the time-dependent maximum Feret diameter of the particle as it flows around the container through particle tracking provides a much more accurate measure of the particle's largest dimension.

Figure 25A:
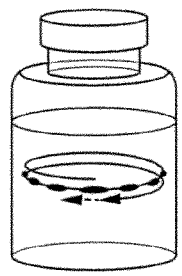
FIGS. 25A-25E illustrate the time-dependence of particle size measurement due to particle movement.
Figure 25B:
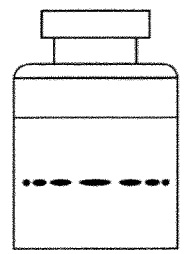

Third, as particles move around a cylindrical container, they generally align their long axis with the direction of the surrounding fluid flow, as shown in FIGS. 25A and 25B. In general, for a cylindrical container this means that elongated particles may appear larger in the center of the image than at the extreme lateral edges. Usually, the imager detects the maximum apparent particle size (Feret diameter) when the particle is travelling orthogonally with respect to the optical axis of the image sensor. If a single particle is tracked as it flows around the container, its correct maximum elongation can be accurately measured—something that is difficult for a static measurement procedure to achieve.

Finally, despite efforts to minimize the effect of motion blur by strobing the illumination (as discussed above), it may still be possible for some degree of motion blur to occur at the start of the image capture sequence, when the fluid and particles are moving fastest. By using a time-dependent analysis of particle size, artifacts in the data due to motion blur (which tends to increase measured particle size) can be identified and suppressed.

Figure 25C:
Figure 25D:
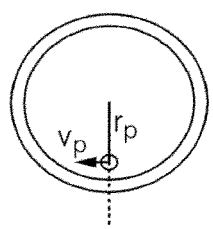
Figure 25E:
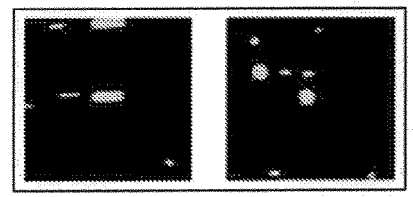

FIGS. 25C-25E illustrate the use of time-series data to track particle trajectories for more precise particle size measurements. FIG. 25C shows the typical track of a 100-micron polymer microsphere moving around a vial post-spin. Particles move fastest relative to the camera as they appear to cross the center of the container, when their velocity is orthogonal to the viewing direction, as shown in FIG. 25D. For example, if the initial spin speed is 300 rpm, and the radial position of the particle $r_p$ is 5 mm, then the particle velocity $v_p$ is about 9.4 m/s. At this speed, a camera exposure time of only 10 μs doubles the apparent particle size due to motion blur. FIG. 25E shows how badly motion blur can affect images: at left, the particles are moving fast (about 300 rpm) and stretched out; at right, the same particles are at a standstill and appear more circular.

Figure 25F:
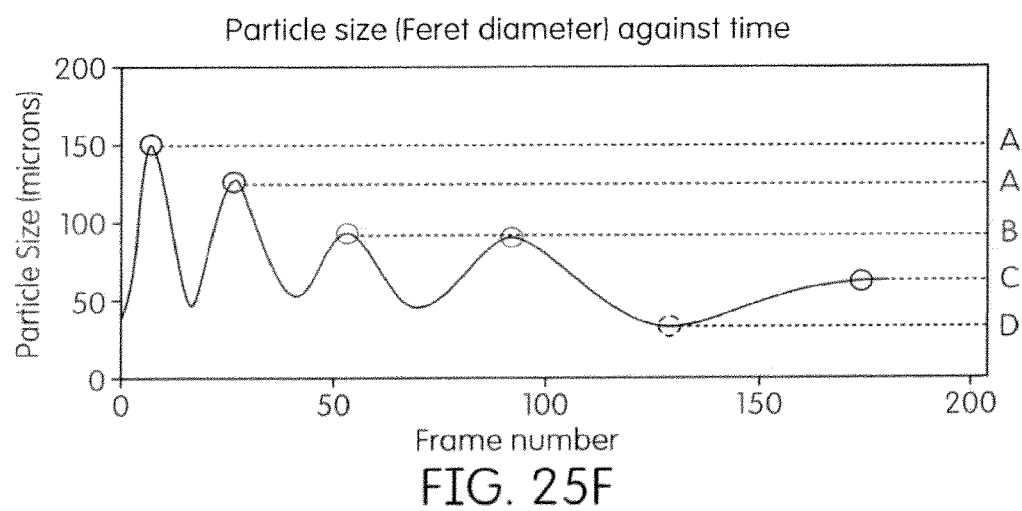
FIG. 25F is a graph of the time-dependent Feret diameter for the particle shown in FIG. 25C.

FIG. 25F is a graph of the time-dependent Feret diameter for the particle shown in FIG. 25C. Due to lensing effects of the cylindrical container, the particle's apparent size is reduced near the edge of the container (right axis tick D). The best estimate of the maximum particle size occurs when the particle traverses the center of the container, at modest speed (right axis tick B). If the speed is too high (which typically occurs during the first few seconds after the container spin) then motion blur exaggerates the particle size (right axis tick A). Eventually, due to fluid drag the particle will stop moving altogether (right axis tick C). In this case, the mid-range peak values (right axis tick B) is the most accurate reading of the maximum particle size.

Particle Characterization

Figures 26A, 26B:
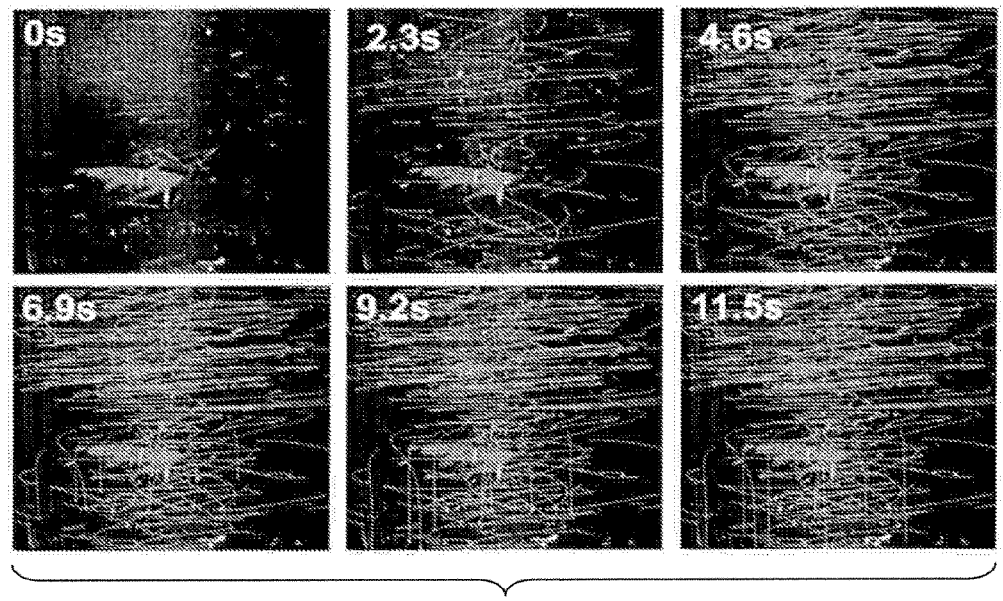
FIG. 26A shows frames of processed time-series data at different intervals with traces indicating different particle trajectories.
FIG. 26B shows illustrative measurements of a number of time-dependent particle properties from particle trajectories in FIG. 26A.

FIG. 26A shows successive frames of time-series data with both the particles and their trajectories. The roughly planar tracks represent trajectories of 100-micron polymer microspheres that mimic protein aggregates. These particles, which are almost neutrally buoyant move with the fluid and do not noticeably sink or rise. The vertically descending tracks represent the trajectories of 100-micron glass beads, which rotated with the fluid initially but sank as the sequence progressed. Rising tracks represent the trajectories of air bubbles and particles with positive buoyancy.

Particle tracking enables measurement of a number of time-dependent properties that can give important clues as to the nature of the particles under examination. For example, air bubbles, which can generally be considered benign from a regulatory standpoint, can confuse current optically-based inspection machines, leading to false positives and unnecessary rejects. In this case, the time-dependent motion of the particle (air bubbles tend to rise vertically as the fluid begins to slow down) leads to a very obvious characteristic that can easily be identified from the trajectory produced by the particle tracking. Similarly, neutrally buoyant particles may not rise or fall much, whereas dense particle sink to the bottom of the container. Lighter particles may be swept up in a vortex formed by the spinning fluid, and heavy particles may have straight-line trajectories.

More broadly, the particle tracking process produces a time-dependent spreadsheet, such as the one shown in FIG. 26B, that contains details of all relevant parameters, including position, velocity of movement, direction of movement, acceleration, size (e.g., two-dimensional area), size (maximum Feret diameter), elongation, sphericity, contrast, and brightness. These parameters provide a signature that can be used to classify a particle as a particular species. This approach, which is achievable via a particle tracking solution, works well for most particles of interest. The ability to categorize particles, on a particle-by-particle basis, based on such an array of time-dependent measurements is a particular benefit of the present invention.

Video Compression

Visualizing very small particles in a comparatively large container benefits from the use of very high resolution image sensors. The rate of image capture also needs to be maximized to ensure accurate trajectory building. The combination of these requirements results in extremely large video files, e.g., 1 GB, 2 GB, 5 GB, 10 GB, or larger. For some applications, it may be necessary to archive original video in addition to the analysis data. For even moderately sized sample sets, the large file sizes involved could potentially make data storage costs prohibitive.

Video compression of the (reversed) time-series data can be used to reduce the sizes of (reversed) time-series data files. Protecting particle data integrity may require the use of lossless video compression. Studies suggest that more commonly used (and more efficient) lossy compression techniques (e.g., MPEG) can critically distort and perturb the image, introducing a number of unwanted visual artifacts.

While lossless compression is, in general, comparatively inefficient compared to lossy compression, there are a number of steps that can improve its effectiveness. Most frames of the time-series data show a handful of small, bright object set against a dark background. The dark background contains no useful information. It is not truly black—rather it is made of very faint random noise. Replacing this background with a purely black background greatly simplifies the image, and makes it much more efficient for standard lossless compression techniques (e.g. zip, Huffyuv) to operate.

This process has been reported elsewhere in the literature. What is novel here, however, is the specific decision of what actually constitutes the background in a given frame. Other compression processes set a threshold intensity level and assume that all pixels in the image below this level are part of the background. This is a broadly effective strategy but can result in a slight reduction in the size of retained particles, and can completely remove very faint particles whose brightness is of the same order as the upper limit of the intrinsic random background 'noise'.

Although these conventional techniques work with (reversed) time-series data, the compression used in illustrative embodiments employs a unique phase that analyses the background for faint particles prior to the employment of destructive thresholding. This ensures the best balance of retaining data integrity while maximizing reductions on data storage requirements.

Fill Volume/Meniscus Detection

Automated embodiments of the visual inspection platform detect the fill volume of the sample accurately, which is important in research applications, where there is no guarantee that the fill volume will be consistent across a particular run. This is especially useful when dealing with very large data files, such as those generated by high-resolution image sensors, causing pressure on data transfer and storage. For this reason, it can be desirable to limit the recorded image to cover no more than the fluid volume, since any further information is irrelevant.

Illustrative systems may employ, for example, automated edge detection or feature recognition algorithms to detect the boundaries of the container in the image as shown in FIGS. 27-29 and described below. Because both the meniscus and the vial base are singular, unique features, a number of possible lighting configurations and/or image processing techniques can be employed to accurately identify their position in the image. Measuring the fill volume and determining the region of the image occupied by the fluid yields the region of interest. Specifically, from FIG. 8, configurations using light sources 122$f$ (backlight), 122$e$ (bottom light) and a combination of 122$a$ and 122$b$ (rear-angled lighting) can all be used to detect the fill volume as described below.

Figure 27A:
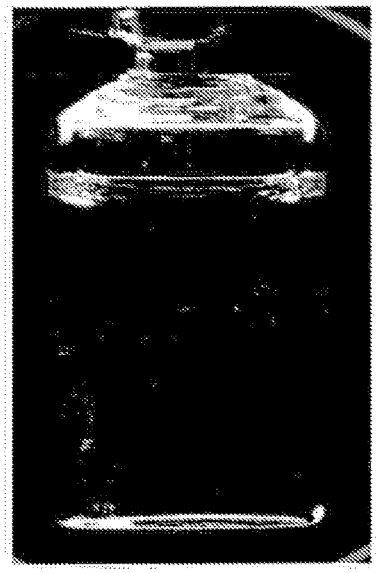
FIGS. 27A-27F illustrate detection of a region of interest using rear-angled illumination.
Figure 27B:
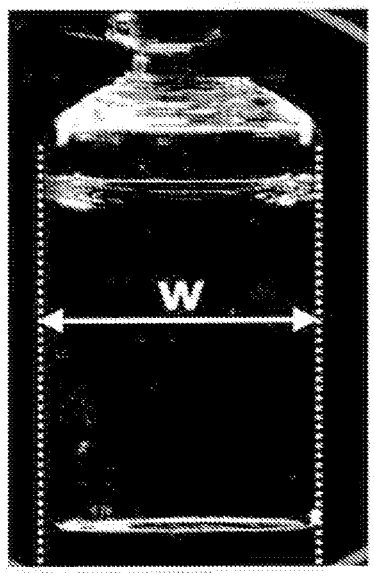
Figure 27C:
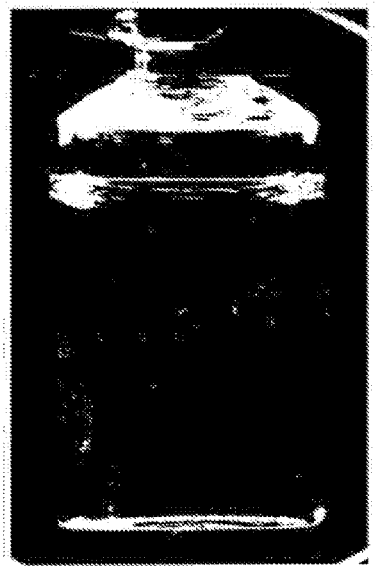
Figure 27D:
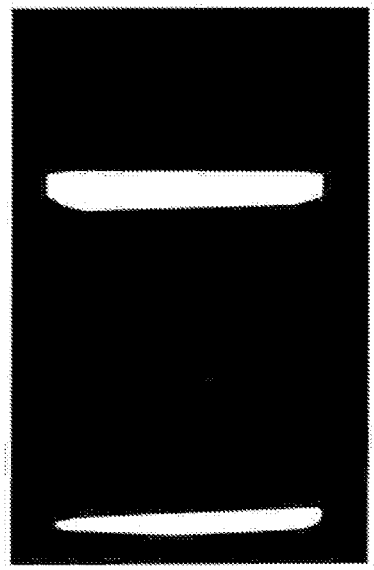
Figure 27E:
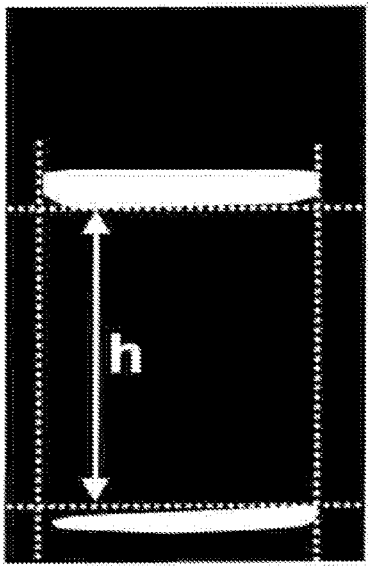
Figure 27F:
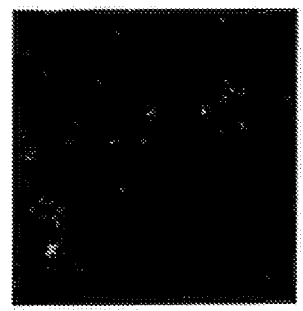

FIGS. 27A-27F illustrate automatic detection of a region of interest within a container using the rear-angled lighting 122$a$ and 122$b$ in FIG. 8. FIG. 27A shows a static image of the container where the base of the vessel and the meniscus are clearly visible as distinct, bright objects. As an example, a processor can employ edge detection to identify the vertical walls of the container and width of the region of interest, w, as shown in FIG. 27B. For detection of the meniscus and vial base, whose appearance can be less predictable, the process can, for example, employ intensity thresholding and segmentation to provide a simplified image of the region of interest (shown in FIG. 27C). At this phase, the processer can automatically identify containers that may not be suitable for particle analysis, e.g., containers whose surfaces are scratched and/or covered in dirt. The effectiveness of the system can be compromised by excessive turbidity, container surface defects, or excessively high particle concentration (whereby individual particles can no longer be discretized in the image). If the processor determines that the container is satisfactory, the objects that correspond to the meniscus and the vial base can then be isolated and simplified as shown in FIG. 27D. The processor defines the vertical height h of the region of interest as the distance between the lower edge of the meniscus and the upper edge of the vial base as shown in FIG. 27E. Finally, the processor may crop the original image stream using the width and height of the region of interest dimensions so that only the area of the image occupied by the visible fluid is recorded as shown in FIG. 27F.

Figure 28A:
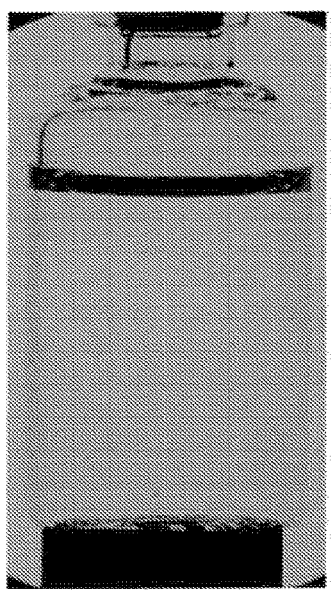
FIGS. 28A-28C illustrate fill volume detection of a backlit vial.
Figure 28B:
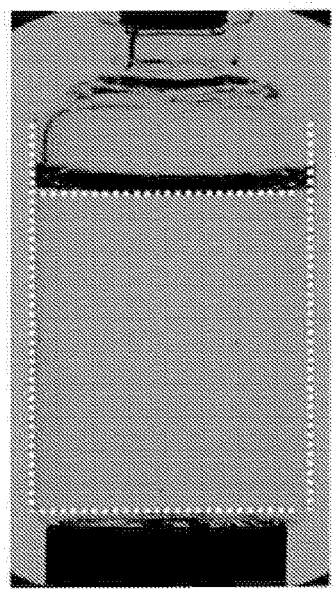
Figure 28C:
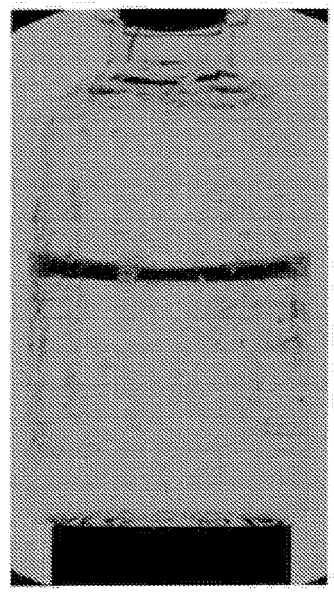

FIGS. 28A-28C illustrate a similar meniscus detection process carried out with data acquired using a backlit configuration (e.g., light source 122$f$ in FIG. 8). FIG. 28A shows a frame of time-series data representing a typical container imaged with a backlight. The meniscus, walls and base are clearly distinguishable, and can be automatically identified using edge detection as in FIG. 28B. However, defects such as large scratches can potentially compromise the accurate detection of the meniscus position whether using a backlight (FIG. 28B) or the rear-angled lights (e.g., as in FIG. 29C, described below). In one implementation, we use intensity thresholding of the image to identify the meniscus and vial base. Since these are relatively large objects, and due to their shape scatter a relatively large amount of light towards the detector, they can be clearly identified, distinct from any other features that may be present.

FIGS. 29A-29D illustrate detection of a meniscus in a cylindrical vessel with a roughly planar bottom. Automated fill volume detection starts with thresholding (FIG. 29A) to detect the meniscus, which then sets the region of interest and is also a measure of fill volume. Next, in FIG. 29B, oblique lighting highlights surface defects such as scratches (shown), dust, fingerprints, glass defects or condensation can make edge detection difficult. Lighting the vial from below (e.g., using light source 122$e$ as in FIG. 8), as in FIG. 29C, illuminates the meniscus in a manner which is (relatively) insensitive to surface defects—here, the meniscus is visible even though the surface is heavily scratched. Lighting from below also makes it possible to differentiate between empty vials and full vials, as shown in FIG. 29D, and to accurately detect the meniscus height at all fill levels between those extremes. Illuminating a vial from below increases the effectiveness of the meniscus detection, since it mitigates errors due to scratches and other surface defects (FIG. 27C). Setting the light source 122e to illuminate the vessel at a slight angle further decreases the sensitivity to surface defects. For syringes, which may be difficult to illuminate from below due to the absence of a transparent container base, a similar effect can be achieved by illuminating obliquely at a narrow angle.

Inspection techniques similar to the meniscus detection described above can also be employed to screen for features that would undermine any subsequent attempts to identify and analyze particles suspended in the fluid. This may include the identification of excessively turbid liquids, critically damaged containers (including excessive scratching or surface debris) and fluids in which the particle concentration is so high particles can no longer be discretized.

Processors and Memory

Those of skill in the art will readily appreciate that the processors disclosed herein may comprise any suitable device that provides processing, storage, and input/output devices executing application programs and the like. Exemplary processors may be implemented in integrated circuits, field-programmable gate arrays, and/or any other suitable architecture. Illustrative processors also be linked through communications networks to other computing devices, including other processors and/or server computer(s). The communications network can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are also suitable.

Figure 30:
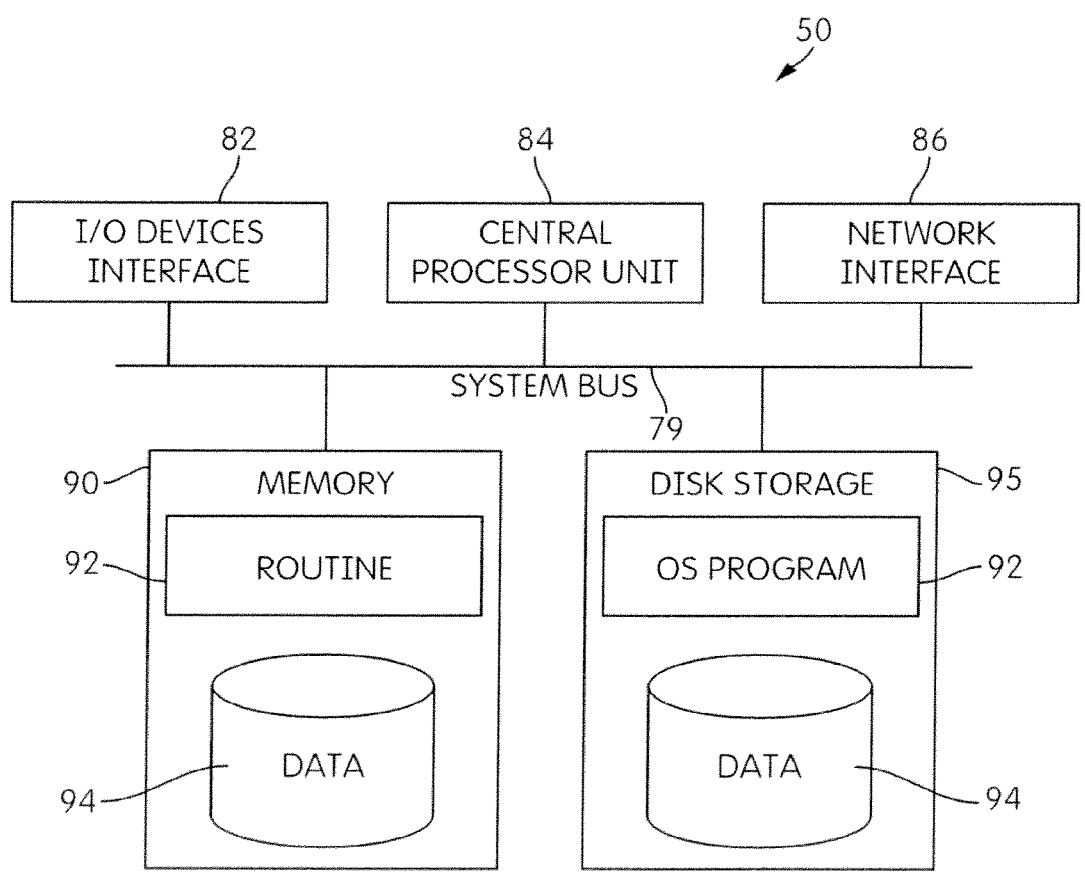
FIG. 30 shows a processor suitable for processing time-series data.

FIG. 30 is a diagram of the internal structure of an illustrative processor 50. The processor 50 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the processor 50. Network interface 86 allows the computer to connect to various other devices attached to a network. Memory 90 provides volatile and/or nonvolatile storage for computer software instructions 92 and data 94 used to implement an embodiment of illustrative visual inspection systems and techniques. Disk storage 95 provides (additional) non-volatile storage for computer software instructions 92 and data 94 used to implement an embodiment of illustrative visual inspection. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for illustrative visual inspection systems. Computer program product 92 can be installed by any suitable software installation procedure, as is well known in the art. In another embodiment, at least a portion of the software instructions may also be downloaded over a cable, communication and/or wireless connection. In other embodiments, exemplary programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the illustrative routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the processor 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Sensor Cooling

In the above-described embodiments, electronic sensors are used to capture images of particles. Electronic sensors such as CCDs are subject to several types of random noise which serve to compromise the integrity of the measured signal, especially at low signal strengths. In some embodiments the sensors may be cooled to reduce noise. The cooling may be accomplished using any suitable technique, including, e.g., the use of thermoelectric coolers, heat exchangers (e.g., cryocoolers), liquid nitrogen cooling, and combinations thereof.

In various embodiments, the noise reduction has an advantage in particle detection, especially relating to the detection of protein aggregates. In typical applications, protein aggregates can be relatively large (e.g., up to several hundreds of microns in diameter) however the physical structure of these aggregate particles is often very loose, with low density (a large proportion of the particle may be porous and filled with the surrounding medium) and of low refractive index contrast to the surrounding medium. Due to these physical properties, protein aggregates can scatter relatively small amounts of light compared to other particles, such as glass fragments or fibers.

Much of the noise affecting contemporary electronic image sensors is thermal in nature. This noise primarily affects the lower end of the dynamic range of the sensor. For example, in some embodiments, the lower X % (e.g., 10%) of the dynamic range is occupied by noise and must be removed during the image thresholding process (e.g., as described above). The threshold value for particle detection must be, at minimum, higher than this value of ~X %, thereby removing low intensity data from the signal. This may prevent the accurate detection of faint particles such as protein aggregates. By reducing the noise, e.g., by cooling the sensor, a lower threshold value may be used, allowing for improved detection of low intensity signals.

Figure 31A:
FIGS. 31A-31D illustrate an example of grayscale thresholding for an image including a bright particle and a faint particle.
Figure 31B:
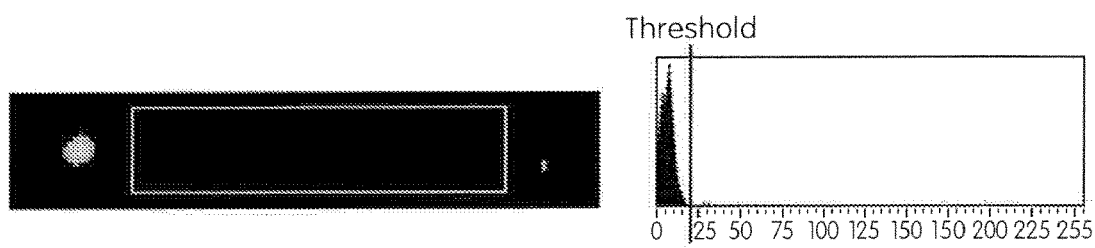

FIGS. 31A-31D illustrates the thresholding issue described above. FIG. 31A shows a cropped segment from a typical image sequence acquired using the devices and techniques described herein. As shown, the images are 8-bit grayscale images, that is, each pixel can have an intensity value ranging linearly from 0 (black) to 255 (white). The image contains two particles, one relatively bright and one very faint. FIG. 31B shows an intensity histogram showing the intensity values of the 'background'—corresponding to the box in the image that does not contain any particles.

The sensor exhibits a Gaussian background noise curve at the low end of the intensity histogram, due at least in part to thermal effects. The width of this curve determines the threshold value for particle detection. In short, particles need to be significantly brighter than the background noise to survive thresholding.

Figure 31C:
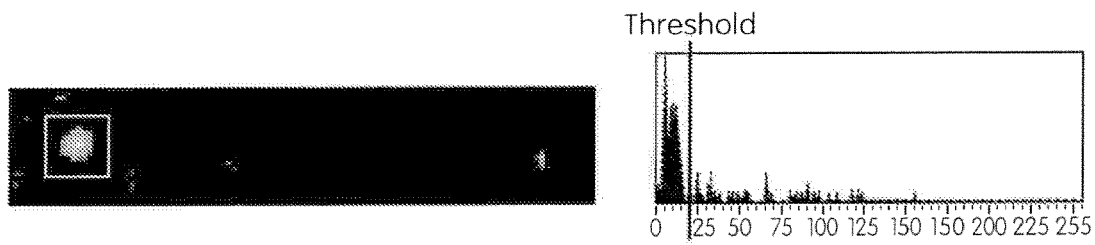

FIG. 31C shows an intensity histogram for the bright particle. The particle image has a significant number of pixels to the right of the threshold value in the histogram and so will be easily detectable after thresholding.

Figure 31D:
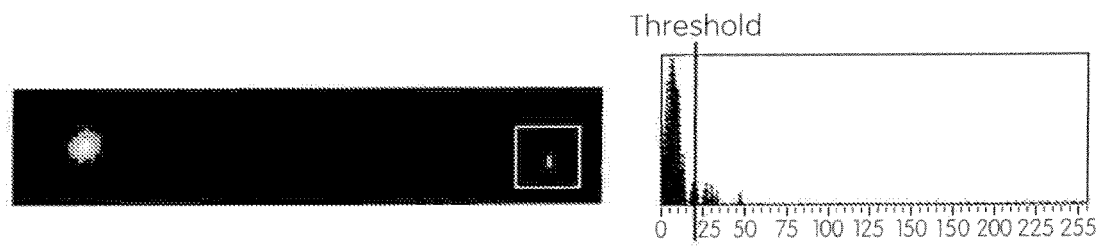

In contrast, as shown in FIG. 31D, the fainter particle has a relatively small number of pixels above the threshold value—it would likely be wiped out during the thresholding/segmentation process. However, if cooling or other techniques were applied to reduce the noise floor, thereby shifting the threshold value to the left, it is possible that the fainter particle could be detected.

Light-Based Enumeration and Non-Destructive Sizing (LENS)

When performing non-destructive sizing and counting of particles within a container, in some embodiments, there are appreciable artifacts generated by the container itself. The liquid interface refracts the light passing through the vial, which causes appreciable distortions in the image or images of the particles used for the sizing and counting procedure. As a result, particles of a given size appear up to, e.g., four times as large in the image, depending on their spatial position within the vial. Note that for a cylindrical container, the particle image is typically only stretched along the lateral axis, not the vertical axis of the vial. (See FIG. 5E for an illustration of these effects).

As noted above, in some embodiments, these distortion effects may be corrected (e.g., mitigated or even eliminated) using corrective optical techniques. However, in some embodiments, such optical correction may be incomplete or unavailable. In such cases, one cannot perform a direct correlation of the size of a particle to the corresponding image on the detector.

Figure 32:
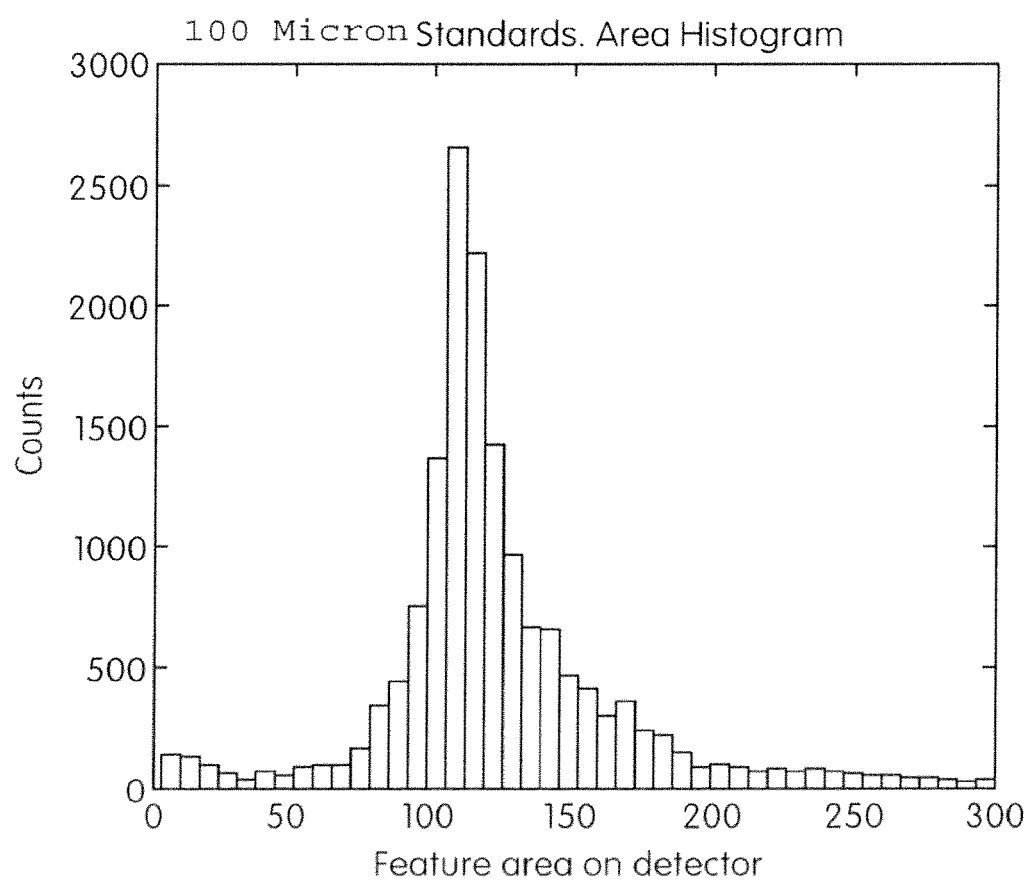
FIG. 32 shows a histogram of apparent particle sizes for a population of particles having a standard size (100 μm).

For example, FIG. 32 shows a histogram for the detected image size for a population of standard sized (as shown 100 µm diameter) particles (polymer microspheres) in a fluid acquired using a system where distortion from the container has not been corrected (corresponding to the situation shown in FIG. 5E). A significant variation in apparent image sizes due to container distortion effects is clearly shown.

Figure 33:
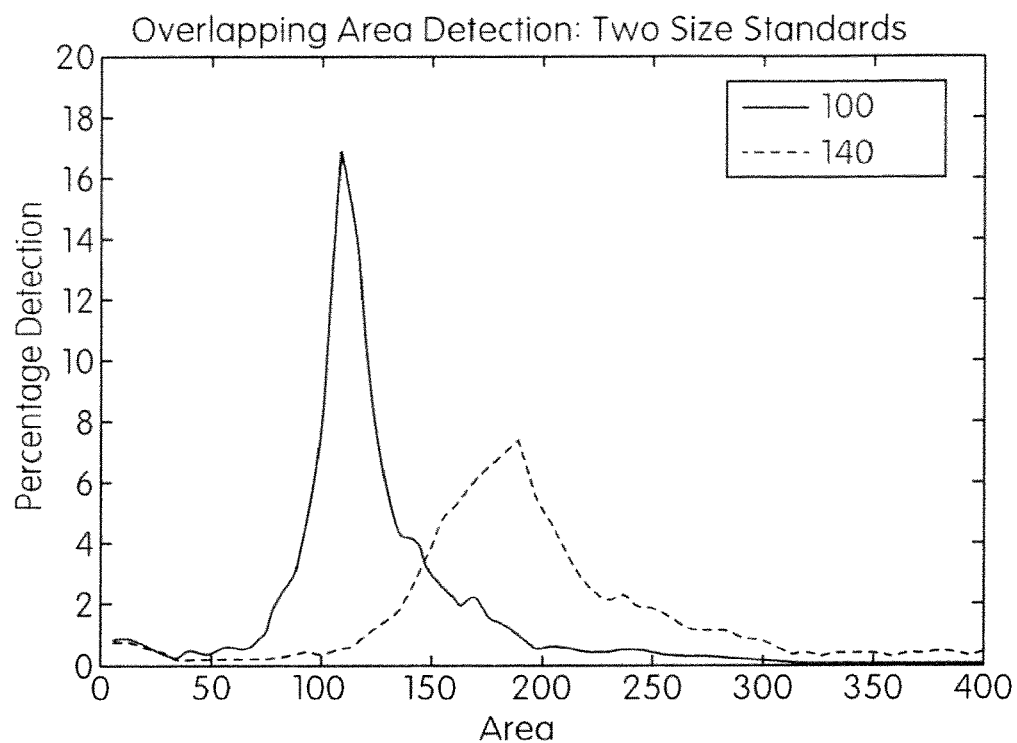
FIG. 33 shows apparent particle size count curves for two populations of particles, each population having the indicated standard size (μm).

This variation makes differentiation between populations of particles of different sizes difficult, as there may be a substantial overlap in the apparent area on the detector from each size population. For example FIG. 33 shows histograms for the detected image size for two population of standard sized (as shown 100 µm and 140 µm diameter) particles in a fluid. Significant overlap between the histograms for the two size populations is clearly shown.

Figure 34:
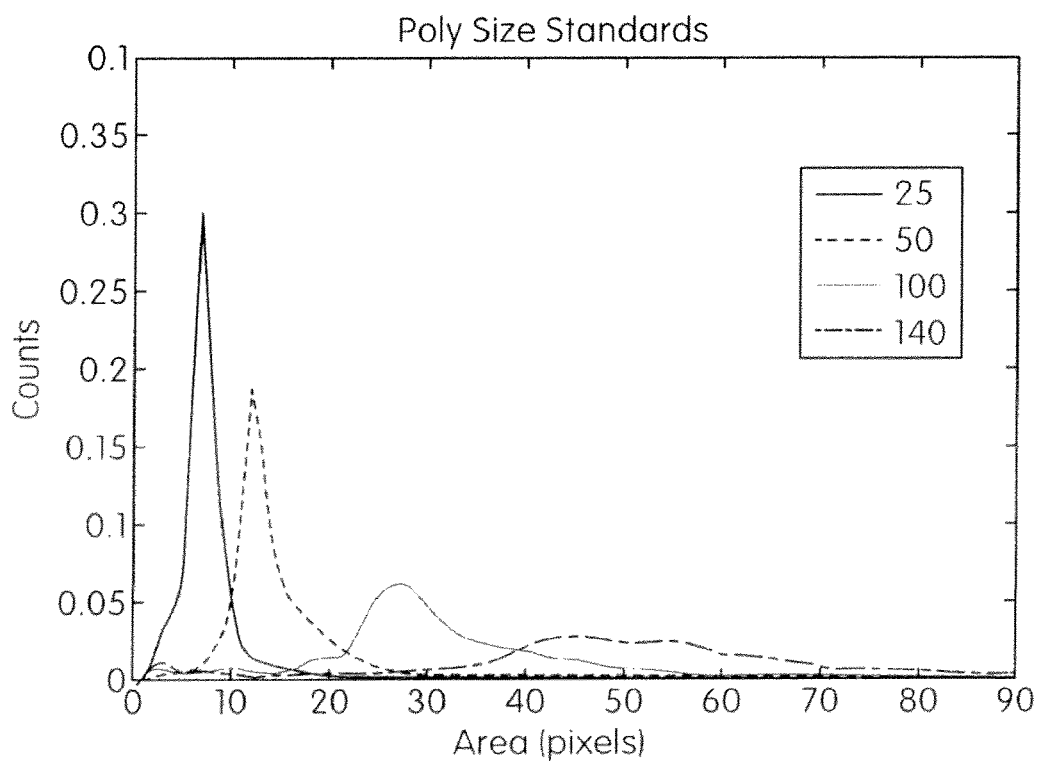
FIG. 34 shows apparent particle size count calibration curves for four populations of particles, each population having the indicated standard size (μm).

In some embodiments, a processing technique may be applied to recover accurate sizing information even in the presence of the distortion effect described above. The processing is calibrated using data obtained using known size standards. For example, FIG. 34 shows experimentally acquired apparent size histograms for four different populations of standard size particles (polymer microspheres).

Although four calibration curves are shown, in various embodiments, any suitable number may be used. In some embodiments, at least two, at least three, at least four, at least five, or at least six curves may be used. In some embodiments, the number of curves is in the range of 2-100, or any subrange thereof, such as 4-6. In some embodiments, a set of experimental calibration curves can be interpolated to generate additional curves (e.g., corresponding to size values between the experimentally measured values).

In some embodiments, the calibration curves may correspond to particle populations having actual sizes that differ by any suitable amount, e.g., at least 1 µm, at least 5 µm, at least 10 µm, at least 20 µm, or more, e.g., in the range of 1 µm to 1000 µm or any subrange thereof.

Once the calibration curves have been determined, the apparent size distribution curve for a sample with particles having unknown sized may be obtained (e.g., from a static image or images, or any other suitable technique). The sample curve may be obtained under the same or similar experimental conditions (e.g., the same or similar container size and shape, fluid properties, illumination conditions, imaging conditions, etc.), This sample curve is compared to the calibration curves to determine information indicative of the sizes of the particles in the sample.

For example, in some embodiments, a weighted superposition of the calibration curves is compared to the sample curve. The weighting of the superposition is varied to fit the superposition to the sample curve, e.g., using any suitable fitting techniques known in the art. The weighting of the best fit to the sample curve is then provides information about the actual sizes of the particle in the sample. For example, in some embodiments, the number of times each calibration curve appears in the best fit superposition corresponds to the count of that size species within the sample.

Figure 35:
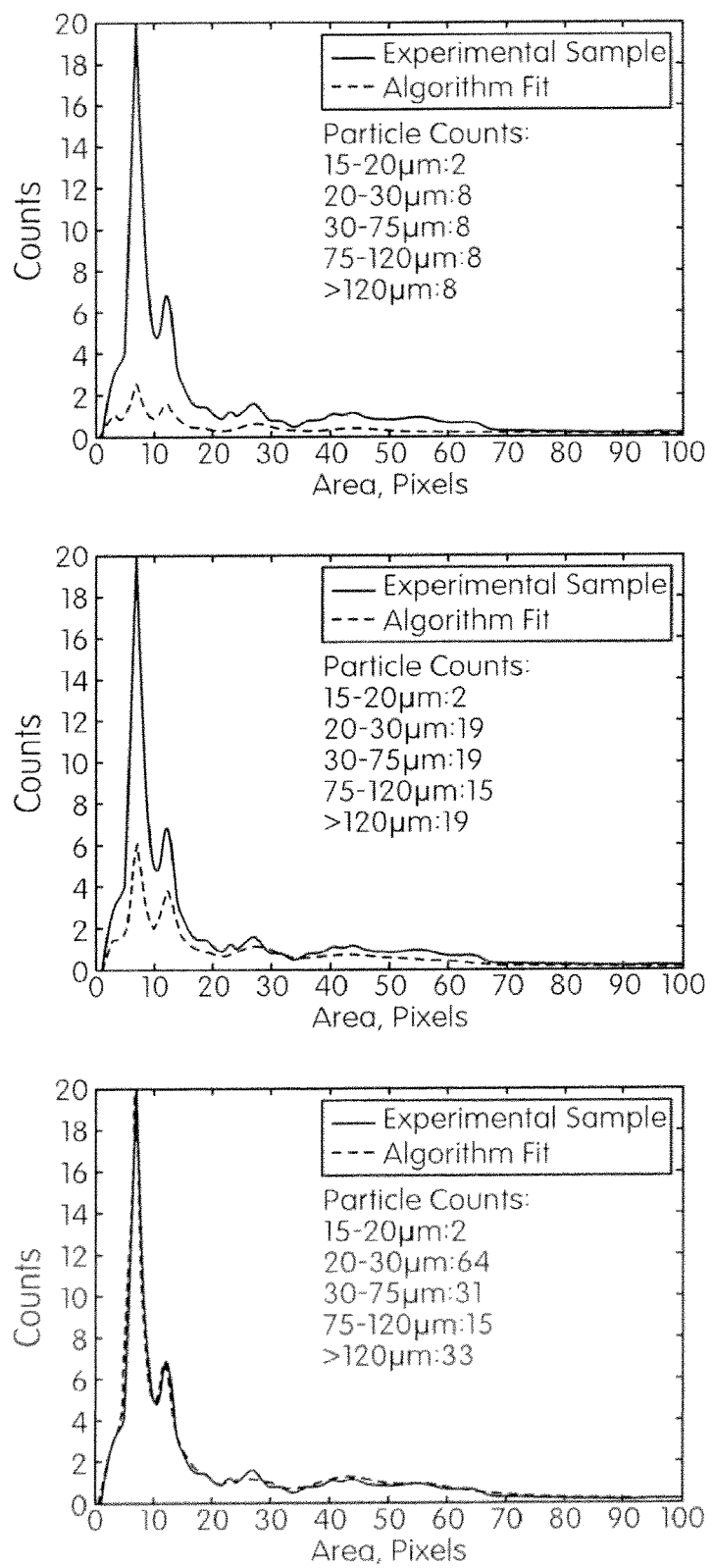
FIG. 35 illustrates fitting a superposition of calibration curves to a sample apparent particle size count curve.
Figure 36:
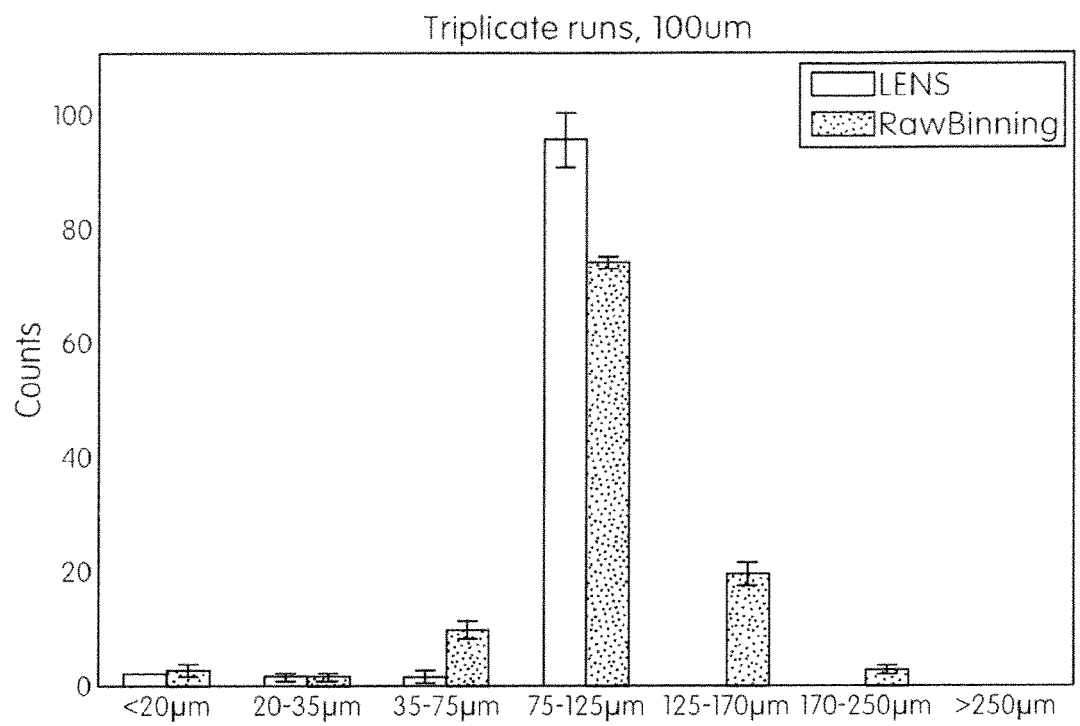
FIG. 36 compares the results of two techniques of counting and sizing particles, raw binning and LENS.

FIG. 35 illustrates the fitting of a superposition of calibration curves to an experimental sample curve. In this case, the sample was prepared such that it was known that the particles were within the range of 75-125 µm in diameter. FIG. 36 shows the resulting size counts from the fit, compared with size counts obtained by simply binning the raw apparent size from the corresponding image. For the raw data, there are significant numbers of spurious counts outside the actual 75-125 µm size range. In contrast, the results obtained from the fit of the calibration curves show a greatly reduced number of spurious counts.

Note that, although one possible approach to comparing the sample data to the calibration data has been described, other suitable techniques may be used. For example, in some embodiments, the sample curve may be decomposed using the calibration curves as basis functions, akin to the Fourier decomposition of a waveform using sinusoidal basis functions. In general any suitable convolution, deconvolution, decomposition, or other technique may be used.

In some embodiments, the Light-Based Enumeration and Non-Destructive ("LENS") sizing techniques may be used in combination with the particle tracking techniques as previously described. For example, the LENS technique will tend to operate better when the particles' shape approximates that of particles in the size standards used to generate the calibration data. Additionally, the techniques tend to perform well when the number of particles is high (e.g. greater than 10, greater than 50, greater than 100, or more), providing a larger data set for the algorithm to process However, in some applications, the number of particles present may be low. In some applications, the focus may be on the larger particles in the sample. Further, in some applications, the sample may include particles having shapes that differ from that of the size standard particles. For example fibers would be elongated rather than the spherical shape used in may standards. Under these conditions, the LENS techniques may not work effectively.

In general any number of particles may be counted using the techniques described above. In some embodiments, an upper limit on the number of particles that may be counted is determined by particle/particle overlap in the sample. In general, the more particles present in the container, the more likely it is that two will not appear disjoint to a single 2D detector. This is a function of particles per volume and the size of the particles. Typically, large particles take up more area on the detector (hence more overlap for a given count/ml when compared with smaller particles). For example, under certain conditions, in an 10 cc vial filled with 8 ml of fluid, up to about 500 particles with a diameter of 50 µm may be counted before undercounting and oversizing effects due to particle overlap become apparent.

Figure 37:
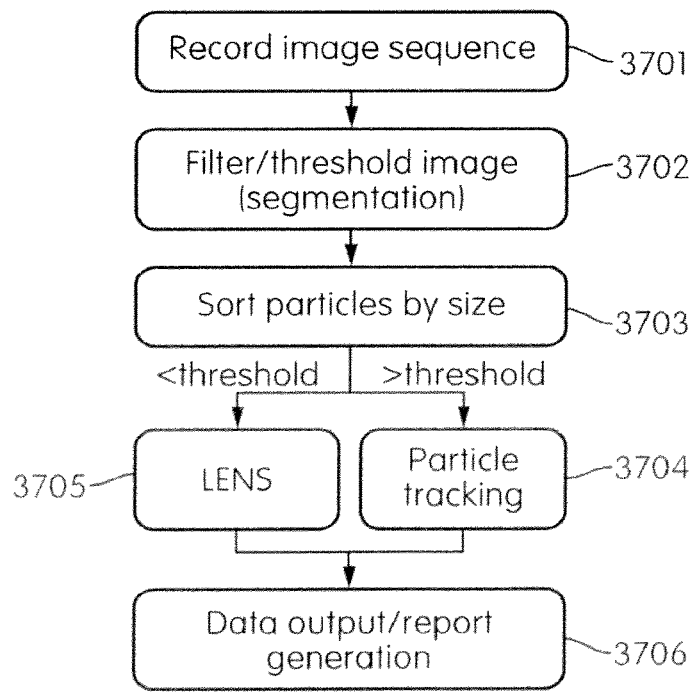
FIG. 37 illustrates a process for counting and sizing particles featuring different sizing techniques for particles below and above a threshold size.

However, the particle tracking techniques presented above may be effective to counting and sizing relatively large particles. Accordingly, in some embodiments, a hybrid of the two approaches may be used. FIG. 37 shows an exemplary embodiment of such a hybrid process. In step 3701, an image sequence is recorded, e.g., using any of the techniques described herein. In step 3702, the image sequence is processed (e.g., filtered, thresholded, segmented, etc,). In step 3703 particle data produced in step 3702 can be pre-screened for particles above a threshold size. These large particles can be removed from the data set and processed in step 3704 using tracking techniques. This may provide quality, time-dependent size measurements of the large particles. If there is a background of smaller particles (below the size threshold) present, then this can be processed in step 3705 using LENS techniques. The data produced by the two different techniques can then be combined into step 3706 to generate a single particle report for the container under scrutiny.

In various embodiments, the size threshold used to determine which technique is applied may be set to any suitable threshold or minimum value of about 1 µm or greater, e.g., about in the range of 1-400 µm of width or diameter of particle or any subrange thereof, e.g., about 1 to about 50 µm, about 50 to about 250 µm, or about 75 to about 100 µm. In some embodiments the particle data sent to each technique may be chosen using criteria other than size, e.g., information related to the shape of the particle. In general, any suitable combination of criteria may be used.

Three Dimensional Imaging and Particle Detection Techniques

As noted above, in some embodiments, automated visual inspection unit 100 may include two or more imagers 110, allowing for three dimensional imaging of the contents of the container 10.

Figure 38A:
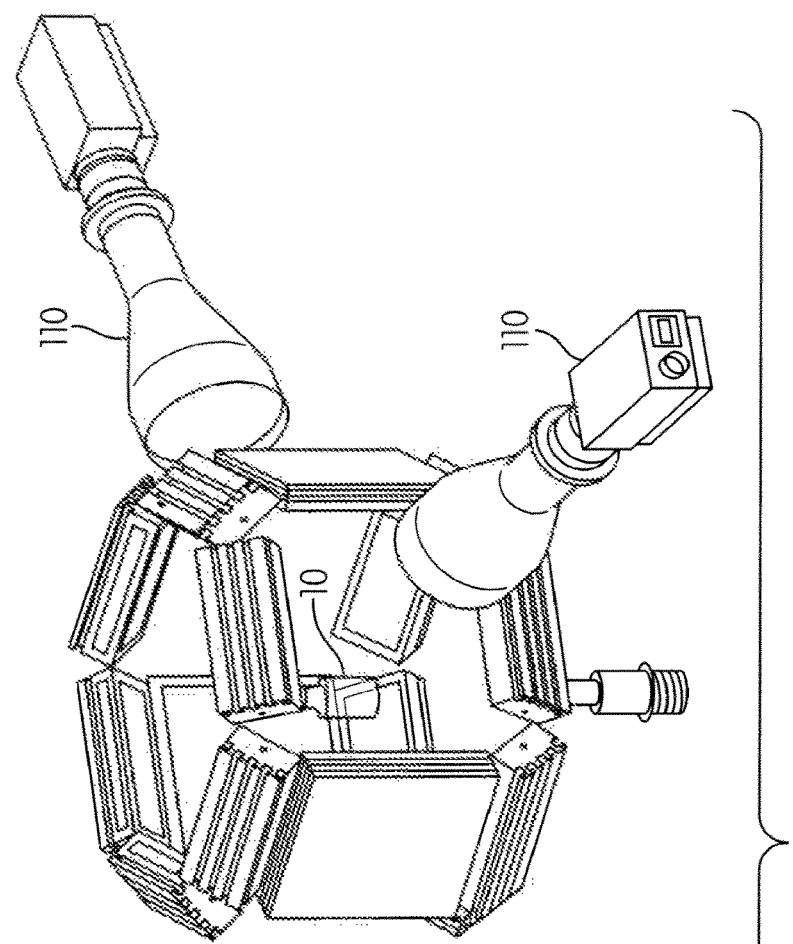
FIGS. 38A-38C illustrate particle tracking systems with multiple imagers to capture time-series data of the moving particles from multiple angles.
Figure 38A:
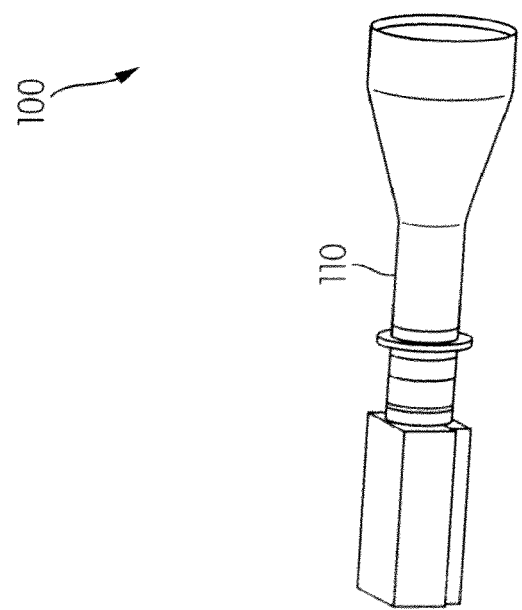
Figure 38B:
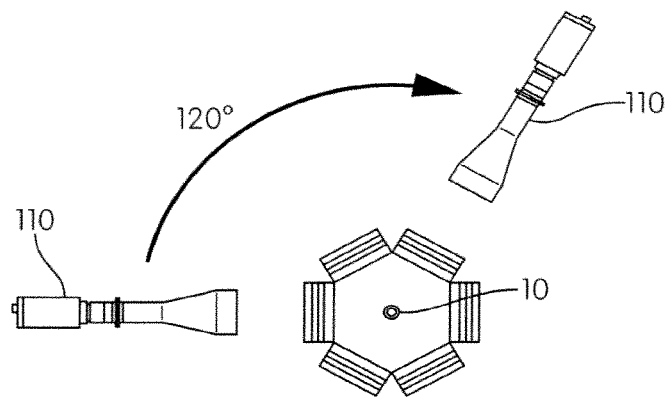
Figure 38C:
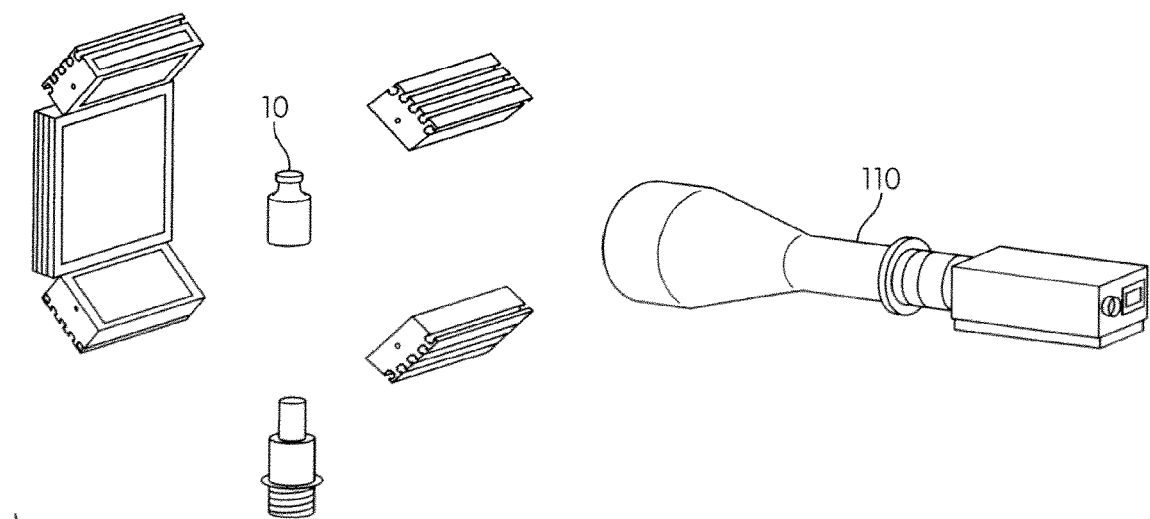

For example FIGS. 38A-38C illustrate a unit 100 featuring three imagers 110. As shown, the imagers 110 are located in a circle around the container 10 at 120 degree intervals, however in various embodiments, more or fewer sensors could be employed. The angles between adjacent imaging sensors do not need to be equal to each other, however, in some embodiments, an equal angle arrangement simplifies the image processing techniques described below.

In some embodiments, each imager 110 is substantially identical. The imagers 110 may be aligned so that they are all at the same physical height in relation to the container 10, with the container 10 centered in the field of view of each imager.

In some embodiments, even when care is taken to optimize this physical alignment, small errors in placement may occur. To account for this, the imagers 110 may be calibrated by imaging a known calibration fixture. Any sufficiently small lateral or vertical alignment deviations can then be accounted for by re-sampling and shifting the captured images accordingly. In some embodiments, the images may be processed to correct for variations in sensitivity or other performance characteristic differences between the different sensors used in the imagers 110.

Figure 39:
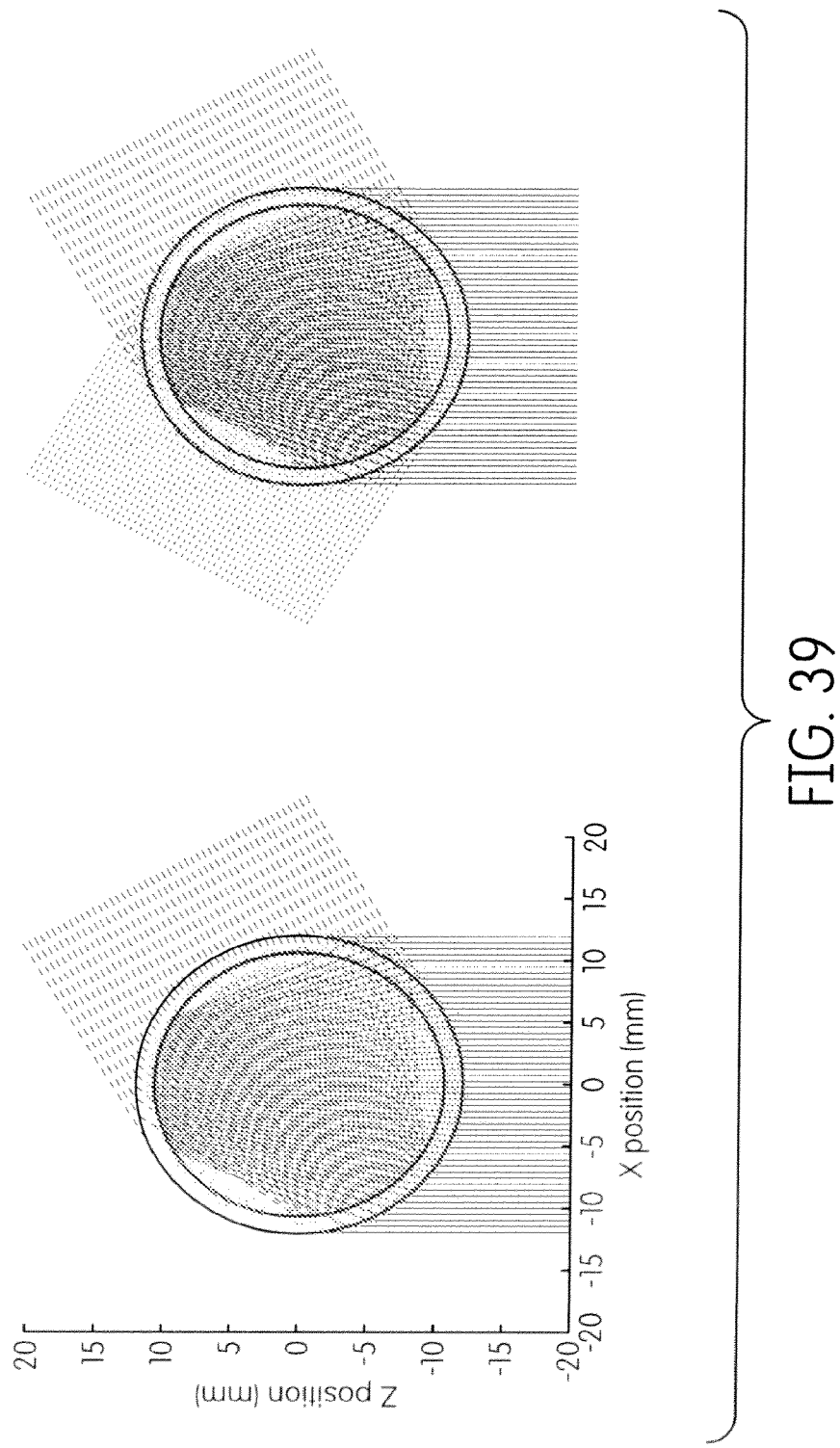
FIG. 39 illustrates the propagation of light rays through a container received by each of two imagers (left panel) and each of three imagers (right panel) of the particle tracking systems of FIGS. 38A-C.

FIG. 38C shows a single imaging arm for the unit 100. As described in detail above, by employing a telecentric imaging arrangement, one assures that only rays substantially parallel to the imaging axis reach the sensor surface of the imager 110. As shown in FIG. 39, using geometric ray optics techniques (or other suitable techniques), one can establish a model of the rays inside the container 10 that would propagate through the container wall and reach the sensor surface.

With the ray vectors known, one can take a point or region on from the two-dimensional image, and propagate that intensity back into the container 10. Taking one horizontal row from the two-dimensional at a time, one can map out a two dimensional horizontal grid within the container volume. The horizontal grids associated with each of the three imagers 110 may be superimposed to produce a single map. By repeating the process for additional horizontal sensor rows, a vertical stack of two-dimensional grids can be built up to form a three dimensional (3D) structure, e.g., corresponding to all or part volume of container 10.

Particle candidates may be identified within the resulting 3D structure using intensity thresholding in a manner similar to that described above. Thresholding can be done on the original two-dimensional images from the imagers 110, or it can be conducted on the horizontal maps within the 3D structure after superposition.

Using a thresholded 3D structure, one can identify candidate particles thereby obtaining a direct measurement of the 3D position of the particle within the fluid volume of the container 10. In typical applications, the 3D position measurement is accurate for most of the fluid volume, however, in some case, e.g., when imagers 110 include telecentric lenses, one may experience blind spots due to the container curvature and associated lensing effect (e.g., as shown in FIG. 39, right panel).

When three imaging arms at angles of 120 degrees are used, as shown, the blind spots correlate closely in pairs (see FIG. 39, right panel). Accurate 3D positioning within the three blind spot regions 3901 may be precluded. However, in those regions, the positional data can be established by examining the two dimensional data from the closest imaging arm.

In various embodiments, the blind spot issue can be mitigated or eliminated by increasing the number of sensor arms to ensure overlapping imaging.

Although one example of using multiple imagers 110 to determine 3D information about the contents of the container 10 has been described, it is to be understood that other techniques may be used. For example, in embodiments using two imagers can apply stereoscopic imaging techniques to determine 3D information.

In some embodiments, e.g. those featuring static or slow moving sample, 3D information could be obtained using a rotating imaging arm, in a manner similar to medical computed tomography machines. The rotating arm would acquire a time series of 2D images from various perspectives, which could be used to construct 3D information, e.g., using any suitable technique, such as those known from medical imaging. If the images are acquired at a speed that is fast relative to the dynamics of the sample, the 3D image may provide accurate 3D information for particle detection.

In some embodiments, the 3D information generated using the techniques described above may be suitable for detecting a candidate particle position, but not ideal for establishing other characteristics of the particle, e.g., the particle size or shape. Therefore, in some embodiments, a hybrid approach may be used. For example, in some embodiments, the 3D position of a particle is established based on the 3D information (e.g., the 3D structure generated as described above). Once three-dimensional positioning of the particles has been established, one can associate with these positions the size and shape measurements obtained from two dimensional images from some or all of the imagers 110.

In some embodiments, particle tracking can be conducted on the 3D positional data, e.g., using 3D tracking techniques similar to two dimensional techniques described above.

In some embodiments 3D tracking provides advantages, particularly when used in combination with two dimensional images obtained from each imager 110.

In 3D tracking, particle-particle occlusions (e.g., as shown in FIG. 5E) are reduced or eliminated. In some embodiments, possible occlusions may occur, e.g., for dense samples in the blind spots where true 3D positioning fails.

As in the two dimensional case described above, in some examples a predictive tracking technique can be used in the 3D context that take advantage information related to the fluid dynamics with the container 10.

In some embodiments, once 3D particle positions have been tracked, information about characteristics of the particles (e.g., size and shape) can be aggregated from the two dimension data from the multiple imagers 110 into multiple time-dependent data sets for each particle. In some embodiments, this may allow a more accurate measurement of individual particle characteristics (e.g., size and shape) than would be possible with a single imaging sensor. For example, in some embodiments, this technique allows clearer detection and size measurement of elongated particles, since the appearance of the particle is no longer dependent strictly on its orientation relative to a single imager 110.

In some embodiments, this approach can be used to mitigate the lensing effect caused by the curvature of the container 10. Using the 3D position of the particle, the measured particle size on the two dimensional images acquired by each of the imagers 110 can be adjusted by to correct for the lensing effect, e.g., by modifying the lateral (horizontal) component of the size measurement with a lensing-effect scaling factor. This scaling factor can be determined based on an optical model of the propagation of light through the container 10 to each of the imagers 110, as detailed above.

Spectral Detection

Figure 45:
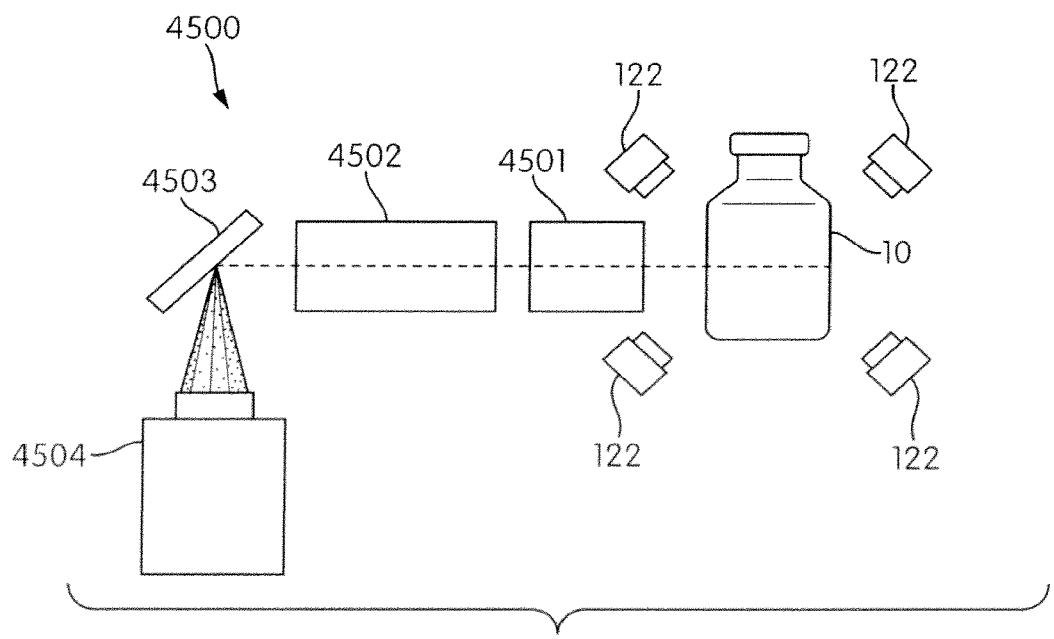
FIG. 45 shows a spectrometer for use with a visual inspection unit.

FIG. 45 shows a sensor 4500 (as shown, a grating spectrometer) that may be used to with a visual inspection unit 100 of the type described herein. For example, the sensor 4500 may form a fourth imaging arm used with the embodiment of the unit 100 shown in FIG. 38A.

The sensor 4500 can be used to detect a characteristic (e.g., a spectral characteristic) of one or more particles in the container 10. For example, as shown, the container 10 is illuminated with broadband light sources 122. The sensor 4500 receives light from the container 10 through distortion corrective optics 4501 (e.g., of any of the types described above), and a telecentric lens 4501. The light from the lens 4501 is directed onto a diffraction grating 4503, that separates the spectral components of the light, which are then imaged on an imaging sensor 4504. In some embodiments, the diffraction grating 4503 operates such that the position of the incident light along one dimension of the sensor 4504 (e.g., the vertical dimension) corresponds to the wavelength of the light. The other dimension on the imaging sensor 4504 corresponds to different spatial positions within the container 10. That is, the sensor 4500 provides spectral information for a sub-region of the container, e.g., in the configuration show a the sub-region is a horizontal "slice" of the container 10.

As particles pass through this central, horizontal plane, their spectroscopic signature can be recorded. At the same time, as described in detail above, the conventional imaging arms of the unit 100 may be used to track the position of the particle within the container (e.g., in three dimensions). This information can be used to determine when a given particle enters the detection sub-region covered by the sensor 4500. When the particle enters the sub-region, the sensor 4500 will sense a characteristic (e.g. a spectral signature) of the particle. The unit 100 can generate data related to this characteristic, and associate this data with data indicative of the identity of the particle in the tracking data.

In various embodiments, the characteristic data can be used for any suitable purpose, e.g., identifying the particle type. For example, spectral information about a given particle can be combined with size, shape, movement or other information about the particle in order to determine the type of the particle.

In some embodiments, the sensor 4500 and illuminating light sources 122 may be modified to detect particle fluorescence, or any other suitable characteristics. In general, any spectral characteristic of the particles may be detected, including a color, an absorption spectrum, an emission spectrum, or a transmission spectrum or a combination of any of these.

Although in the example described above, the sensor 4500 is included in a unit 100 featuring three image arms, in other embodiments any other suitable number of imaging arms may be used, e.g., one, two, four, five, or more. In some embodiments where a single imaging arm is used, the sensor 4500 may be aligned with the imaging arm, e.g., by using a beam splitter (not shown) to split a beam of light from the container 10, and direct components to the single imaging arm and the sensor 4500. In other embodiments, e.g., where multiple imaging arms are used, the sensor 4500 may be oriented at any suitable angle relative to the imagers.

In-Situ Measurements of Sample Properties

In some embodiments, the inspection unit 100 may include one or more detectors (not shown) that may be used to measure the refractive index of the fluid in the container 10. For example, in some embodiments, a narrow off-axis collimated laser beam may be directed through a fluid filled portion of the container 10 and detected to measure the displacement of the beam due to refraction through the container 10. If the material and geometry of the container 10 is known, this information may be used to determine the refractive index of the fluid. In various embodiments, any other suitable index of refraction detection technique may be used.

In some embodiments, the measured refractive index of the fluid may be used as an input parameter in any of the processing schemes described herein (e.g., processing used to compensate for lensing effects caused by the curvature of the container 10).

In some embodiments, the inspection unit 100 may also include one or more detectors (not shown) that may be used to measure information indicative the shape of the container 10. For example, in some embodiments, a narrow off-axis collimated laser beam may be directed through an air filled (e.g., upper) portion of the container 10 and detected to measure the displacement of the beam relative to a reference. The deflection may be used to precisely measure the thickness of the wall of the container (e.g., with an accuracy of 0.25 mm or less). In various embodiments, any other suitable technique for determining the shape of the container may be used.

In some embodiments, the detected geometric information may be used, e.g., as described above, in determining the refractive index of the fluid in the container 10. In some embodiments, the detected geometric information may be used as an input parameter for various processing techniques described herein (e.g., processing used to compensate for lensing effects caused by the curvature of the container 10), or any other suitable purpose.

Immersion Imaging

As discussed in detail herein, in various embodiments the refractive properties of the fluid in container 10 may cause unwanted image distortion effects. In some embodiments, these effects may be mitigated by filing some or all of the space between the container 10 and an imager 110 used to image the container with a medium that has an index of refraction that more closely matches the index of the fluid than air.

In some embodiments, refractive distortion may be further mitigated by matching the refractive index of the container 10 the fluid contained within the container.

In some embodiments, these immersion imaging techniques may reduce or eliminate the need for corrective optics and or processing used to reduce distortion (e.g., the lensing effect described in detail above).

Sample Temperature Control

In some embodiments, the inspection unit 100 may include one or more devices (not shown) for controlling the temperature of the sample within the container 10. For example, in some embodiments, the temperature control device may be used to vary the temperature of the container within the range of 0° C. to 40° C., 0° C. to 100° C., or other suitable ranges. In some embodiments, the temperature control device may maintain the temperature at a stable value, e.g. a value that varies by less than 5° C., 2.5° C., 1° C., 0.1° C., 0.01° C., or less.

Temperature control may be particularly advantageous in applications where temperature control is important for ensuring that the samples do not deteriorate during the detection process. In some embodiments, by varying the temperature of the sample in a controlled manner, temperature and time-dependent stability studies may be conducted for temperature sensitive products. For example, the platform could be used to measure the dissolution (or in some cases, formation) of protein aggregates as drug product is controllably increased in temperature from, e.g., 4° C. (refrigeration) to 20° C. (room temperature), or to 37° C. (human body temperature).

In various embodiments, temperature control may be accomplished using any suitable technique. In some embodiments, the environment within the inspection unit may be sealed and thermally isolated, and the temperature controlled using, e.g., an air conditioning unit. In some embodiments, a heating coil and a thermoelectric cooler (e.g., a Peltier cooler) may be integrated in a sample holder for the container 10. In embodiments where multiple containers are held in a tray, the temperature of the tray may be controlled by circulated a heating/cooling working fluid through the tray (e.g., by passing the working fluid through a heat exchanger). In general one or more temperature sensors and or thermostats may be used to provide closed loop temperature control.

Iterative Inspection Techniques

In some embodiments, the inspection unit 100 may re-run the inspection of a given sample with one or more modified operating parameters (e.g., spin speed) that may be chosen based on the outcome of an initial inspection run. This process may be repeated iteratively to better adjust the operating parameter to the particular sample under inspection For example, in some embodiments, the inspection can be re-run (e.g., with a modified spin speed) if the output of a particle detection and sizing operation returns results that are outside a range of expected results (indicating an error in the initial inspection).

Background Reference Mapping for Auto-Calibration

As described in detail above, in various embodiments it is desirable to characterize distortion effects (e.g., lensing effects) caused by refraction of light passing through the container 10 to an imager 110. In some embodiments, the inspection unit 100 itself may be used to map out the distortions caused by the container 10. This map can then be used during image processing to compensate for these effects.

For example, in some embodiments, one or more calibration indicia (e.g., a grid) may be placed behind the container 10 as a background for an imager 110. By detecting these indicia in the acquired image (e.g., using edge detection or other suitable feature detection techniques), and comparing their appearance to the known actual appearance, the refractive distortion may be detected and mapped.

In some embodiments, this approach may be used to correct for distortion caused by non-cylindrical containers, e.g., containers that are rotationally symmetric about an axis, but with varying circumferences about the axis (such as containers having shapes familiar from contemporary plastic soda bottles).

Vibration Auto Detection and Mitigation

As noted above, in some embodiments, vibrations can degrade the performance of the inspection unit 100. Vibrations cause otherwise static features (such as cosmetic defects on the container surface) to oscillate during video acquisition. This may reduce the performance of the static feature removal phase, by creating small but significant oscillating halos that survive the static feature removal and potentially cause spurious results in subsequent particle detection algorithms. In various embodiments, one or more of the following techniques may be used to reduce the effect of vibration.

In some embodiments, the oscillating halo features that form around removed static features can be mitigated by increasing the size of image region corresponding to the detected static features (e.g., by a thickness of one or several pixels) so that the areas of the image containing the thin oscillating halos are also deleted prior to the particle analysis phase. However, in some embodiments, this approach may be disadvantageous in that it serves to reduce the effective available sensor area.

In some embodiments, a screening algorithm to detect the presence of the oscillating features. For example, the features may be detected by processing the image to locate features that oscillate, but do not translate across the image.

In some embodiments, the features can be further identified based on their proximity to detected static features.

In some embodiments, characteristics of the vibration of the container may be detected from the captured images, e.g., using edge detection to detect movement of the container walls, so that the system can automatically detect and potentially warn users of unacceptably high levels of environmental vibrations.

In some embodiments, characteristics of the vibration of the container may be detected using physical sensors. For example, in some embodiments, a tool head holding and manipulating the container during inspection may include motion detection devices (e.g., high-precision accelerometers) which provide feedback from which the system can automatically provide warning to users regarding vibration levels above an established threshold.

EXAMPLES

The following provides exemplary performance characteristics for an embodiment of and automated visual inspection unit 100 of the type described herein.

Figure 40:
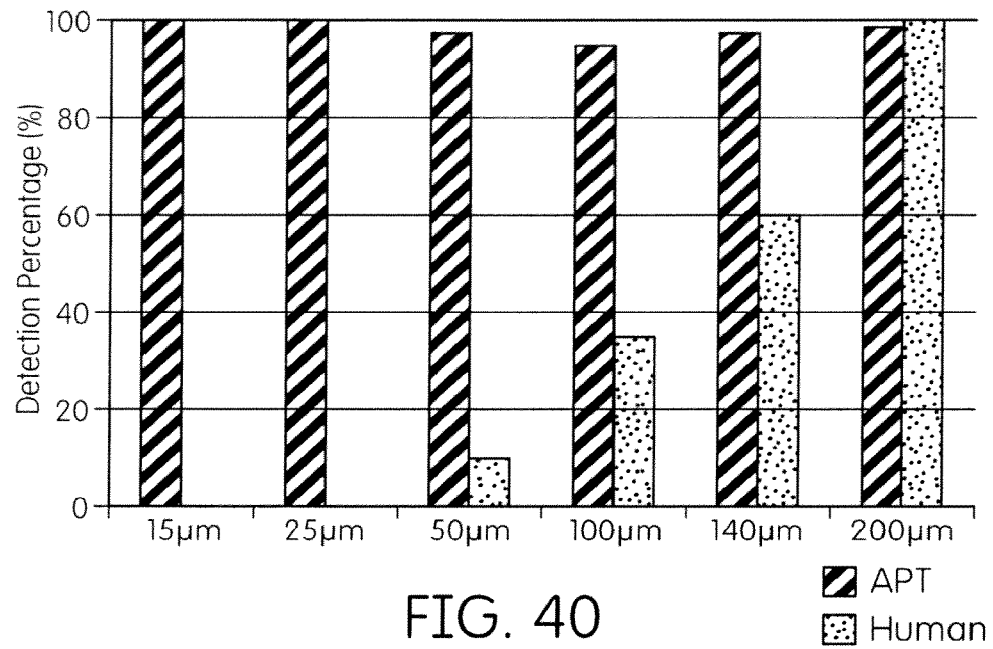
FIG. 40 shows particle detection results for an automated particle detection system (designated "APT") compared with human results by visual inspection.

Referring to FIG. 40, the unit 100 was presented with containers 10 each including only a single polymer sphere of a known size. Multiple detection runs (n=80) were performed on each container and the detection percentage measured (data bars labeled "APT" in the figure). As shown, the detection percentage for the system was above 90% for particle sizes ranging from 15-200 µm in diameter. Detection percentages for the same task performed visually by a trained human are presented for comparison (data bars labeled "human"). Note that human detection capability falls off rapidly for particle sized below 200 µm.

Figure 41:
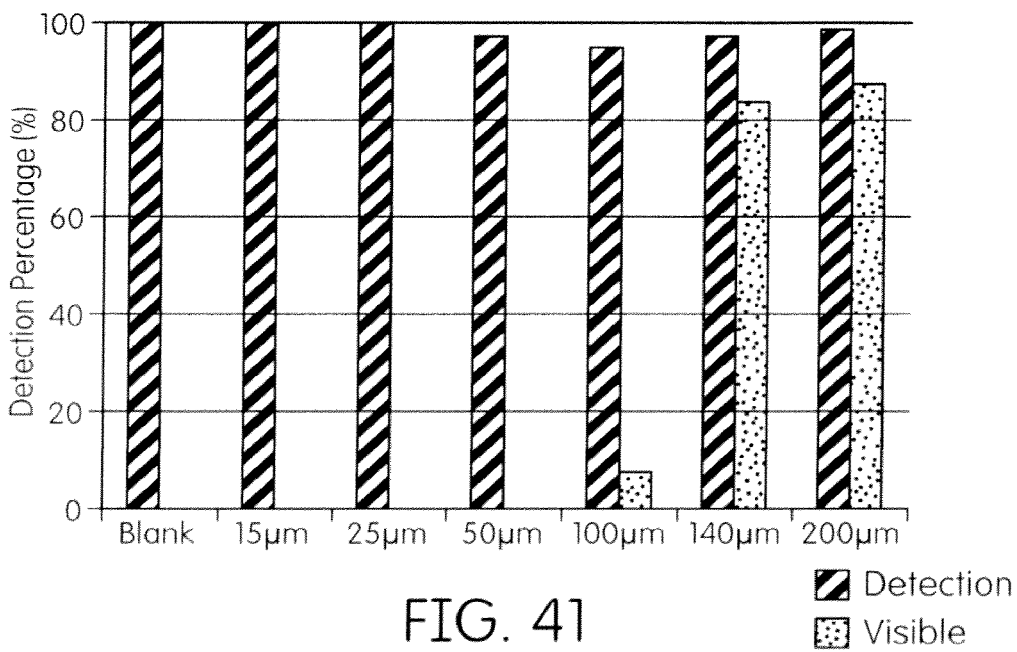
FIG. 41 shows particle detection and classification results for an automated particle detection system.

Referring to FIG. 41, in another test, the unit 100 was presented with containers holding particles above and below the visible cutoff of 125 µm in diameter. The unit 100 detected the particle and also classified the particle based on size as being above or below the visible cutoff of 125 As shown, the detection percentage for the system was above 90% for particle sizes ranging from 15-200 µm in diameter. The unit 100 also correctly categorized the detected particles with a very high degree of accuracy.

Figures 42, 43:
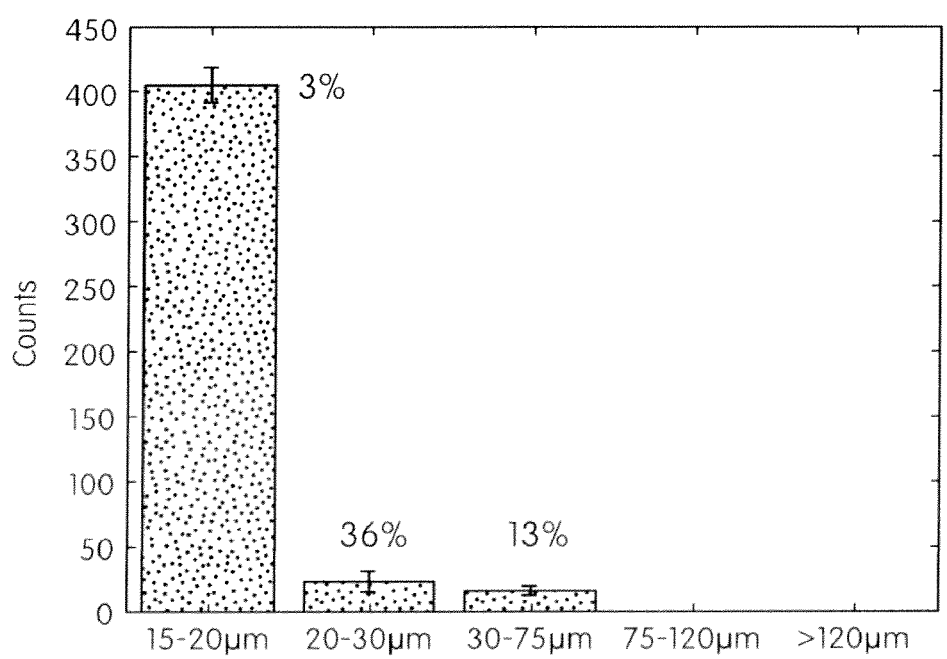
FIG. 42 shows a chart summarizing the linearity of particle count as a function of sample dilution for and automated particle detection system.
FIG. 43 shows the precision of automated particle detection system used to detect and count protein aggregate particles.

Referring to FIG. 42 dilution series were created for multiple size standards, each series made up of containers holding particles at a given concentration. The resulting containers were analyzed by the unit 100 to provide a particle count, and regression was used to determine R-square "R^2" values for linearity of count versus inverse dilution factor. As shown, the "R^2" value was above 0.95 for particle sizes ranging from 15-200 µm, indicating excellent linearity.

Referring to FIG. 43, a stressed sample containing protein particles was analyzed by the unit 100 to determine a particle count binned by particle size. The precision of the particle count for each bin taken over 10 runs is shown. The protein particles are of unknown size, which makes absolute size accuracy comparison impossible, however, as shown, the precision of the system for counting and sizing the proteins is high. The normalized error for the measurement was 3%, indicating excellent precision.

Figure 44:
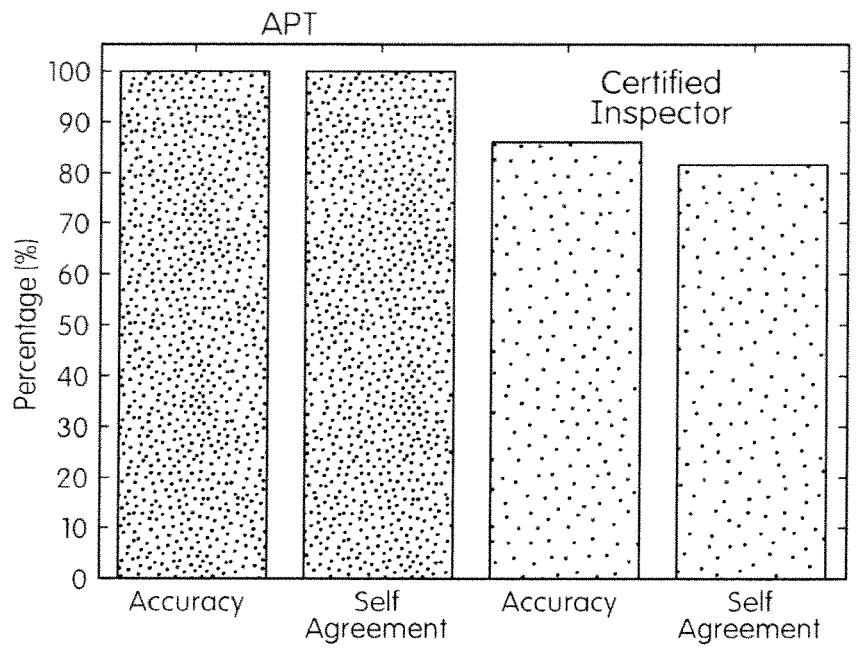
FIG. 44 shows protein aggregate particle detection results for an automated particle detection system (designated "APT") compared with human results by visual inspection.

Referring to FIG. 44, the unit 100 was also characterized at detecting blank vs. protein particle containing vials. The performance of the unit 100 was compared with that of a certified visual inspector observing the same set of vials. The unit 100 (labeled "APT" in the figure) detected all 40 protein vials and 80 blanks correctly in triplicate runs. The self agreement at classifying visible and subvisible particles was 100%. Humans scored only around 85% in both categories.

CONCLUSION

Those of ordinary skill in the art realize that processes involved in an automated system and method for nondestructive particle detection and identification (processing time-series data acquired through visual inspection) may be embodied in an article of manufacture that includes a computer-usable medium. For example, such a computer usable medium can include a readable memory device, such as a hard drive device, a CD-ROM, a DVD-ROM, a computer diskette or solid-state memory components (ROM, RAM), having computer readable program code segments stored thereon. The computer readable medium can also include a communications or transmission medium, such as a bus or a communications link, either optical, wired, or wireless, having program code segments carried thereon as digital or analog data signals.

A flow diagram is used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to subject matter containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As used herein, the term optical element may refer to one or more refractive, reflective, diffractive, holographic, polarizing, or filtering elements in any suitable combination. As used herein terms such as "light", "optical", or other related terms should be understood to refer not only to light visible to the human eye, but may also include, for example, light in the ultraviolet, visible, and infrared portions of the electromagnetic spectrum.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for nondestructive detection of an undissolved particle in a vessel that is at least partially filled with a fluid, the method comprising:
   (a) using at least one imager to image the particle;
   (b) processing the image to determine position data indicative of a position of the particle in the vessel;
   (c) detecting the particle based at least in part on the position data, wherein detecting the particle based at least in part on the position data comprises identifying the presence of the particle in a sub-region of the vessel;
   (d) using a sensor to determine a characteristic of the particle when the particle is located in the sub-region of the vessel,
   (e) generating particle characteristic data indicative of the determined characteristic; and
   (f) associating the particle characteristic data with data identifying the particle.

2. The method of claim 1, wherein:
   the at least one imager comprises at least two imagers positioned to image the particle from different perspectives to each acquire a respective one or more two dimensional images of the particle in the fluid;
   processing the image to determine position data comprises combining the two dimensional images from the at least two imagers to determine three dimensional data indicative of the position of the particle in the vessel; and
   detecting the particle comprises detecting the particle based at least in part on the three dimensional data.

3. The method of claim 2, wherein the characteristic of the particle comprises a spectral characteristic.

4. The method of claim 3, wherein the sensor comprises a spectrometer device positioned to sense one or more spectral characteristics of light incident from the sub-region of the vessel.

5. The method of claim 4, wherein the sub-region of the vessel comprises a substantially planar layer of fluid in the vessel.

6. The method of claim 5, wherein the sensor comprises a telecentric imager positioned to image the sub-region of the vessel onto the spectrometer device.

7. The method of claim 4, wherein the one or more spectral characteristics comprise a color, an absorption spectrum, or a transmission spectrum or a combination of any of these.

8. An apparatus for nondestructive detection of an undissolved particle in a vessel that is at least partially filled with a fluid, the apparatus comprising:
   (a) at least one imager positioned to image the particle;
   (b) at least one sensor configured to determine a characteristic of the particle when the particle is located in a sub-region of the vessel;
   (c) at least one processer operably coupled to each of the at least one imager and the sensor and configured to:
      process an image from the at least one imager to determine a position data indicative of the position of the particle in the vessel;
      detect the particle based at least in part on the position data and identify a presence of the particle in the sub-region of the vessel;
      use a signal from the sensor to determine a characteristic of the particle when the particle is located in the sub-region of the vessel;
      generate particle characteristic data indicative of the determined characteristic; and
      associate the particle characteristic data with data identifying the particle.

9. The apparatus of claim 8, wherein:
   the at least one imager comprises at least two imagers positioned to image the particle from different perspectives to each acquire a respective one or more two dimensional images of the particle in the fluid;
   the processor is configured to combine the two dimensional images from the at least two imagers to determine three dimensional data indicative of the position of the particle in the vessel; and the processor is configured to detect the particle based at least in part on the three dimensional data.

10. The apparatus of claim 9, wherein the characteristic of the particle comprises a spectral characteristic.

11. The apparatus of claim 10, wherein the sensor comprises a spectrometer device positioned to sense one or more spectral characteristics of light incident from the sub-region of the vessel.

12. The apparatus of claim 11, wherein the sub region comprises a substantially planar layer of fluid in the vessel.

13. The apparatus of claim 12, wherein the sensor comprises a telecentric imager positioned to image the sub-region of the vessel onto the spectrometer.

14. The apparatus of claim 11, wherein the one or more spectral characteristics comprise a color, an absorption spectrum, or a transmission spectrum or a combination of any of these.

* * * * *